US012735721B2

(12) United States Patent
Maguire et al.

(10) Patent No.: US 12,735,721 B2
(45) **Date of Patent: *Sep. 15, 2026**

(54) ENGINEERED ADENO-ASSOCIATED (AAV) VECTORS FOR TRANSGENE EXPRESSION

(71) Applicants: The General Hospital Corporation, Boston, MA (US); President and Fellows of Harvard College, Cambridge, MA (US)

(72) Inventors: Casey A. Maguire, Arlington, MA (US); Eloise Marie Hudry, Roxbury Crossing, MA (US); Killian S. Hanlon, Boston, MA (US)

(73) Assignees: The General Hospital Corporation, Boston, MA (US); President and Fellows of Harvard College, Cambridge, MA (US)

( * ) Notice: Subject to any disclaimer, the term of this patent is extended or adjusted under 35 U.S.C. 154(b) by 1071 days.

This patent is subject to a terminal disclaimer.

(21) Appl. No.: 17/442,894

(22) PCT Filed: Mar. 30, 2020

(86) PCT No.: PCT/US2020/025720

§ 371 (c)(1),
(2) Date: Sep. 24, 2021

(87) PCT Pub. No.: WO2020/198737

PCT Pub. Date: Oct. 1, 2020

(65) Prior Publication Data

US 2022/0195458 A1 Jun. 23, 2022

Related U.S. Application Data

(60) Provisional application No. 62/825,703, filed on Mar. 28, 2019.

(51) Int. Cl.

| | |
|---|---|
| ***C12N 15/86*** | (2006.01) |
| ***C07K 14/005*** | (2006.01) |
| ***C12N 15/10*** | (2006.01) |
| *C40B 40/02* | (2006.01) |

(52) U.S. Cl.

CPC ............ *C12N 15/86* (2013.01); *C07K 14/005* (2013.01); *C12N 15/1037* (2013.01); *C12N 2750/14122* (2013.01); *C12N 2750/14143* (2013.01); *C40B 40/02* (2013.01)

(58) Field of Classification Search

CPC ................ C12N 15/86; C12N 15/1037; C12N 2750/14122; C12N 2750/14143; C07K 14/005; C07K 7/06; C40B 40/02; A61K 48/00

See application file for complete search history.

(56) References Cited

U.S. PATENT DOCUMENTS

| | | | |
|---|---|---|---|
| 5,399,363 A | 3/1995 | Liversidge et al. | |
| 5,478,745 A | 12/1995 | Samulski et al. | |
| 5,543,158 A | 8/1996 | Gref et al. | |
| 5,552,157 A | 9/1996 | Yagi et al. | |
| 5,565,213 A | 10/1996 | Nakamori et al. | |
| 5,567,434 A | 10/1996 | Szoka, Jr. | |
| 5,641,515 A | 6/1997 | Ramtoola | |
| 5,738,868 A | 4/1998 | Shinkarenko | |
| 5,741,516 A | 4/1998 | Webb et al. | |
| 5,795,587 A | 8/1998 | Gao et al. | |
| 6,001,650 A | 12/1999 | Colosi | |
| 6,156,303 A | 12/2000 | Russell et al. | |
| 7,198,951 B2 | 4/2007 | Gao et al. | |
| 7,504,490 B1 * | 3/2009 | Weinstock ............. | C07K 14/38 435/69.3 |
| 9,102,949 B2 | 8/2015 | Gao et al. | |
| 9,585,971 B2 | 3/2017 | Deverman et al. | |
| 9,920,317 B2 | 3/2018 | Lee et al. | |
| 11,149,256 B2 | 10/2021 | Gradinaru et al. | |
| 2003/0138772 A1 | 7/2003 | Gao et al. | |
| 2003/0194721 A1 | 10/2003 | Mikita et al. | |
| 2004/0214272 A1 | 10/2004 | La Rosa et al. | |
| 2007/0020624 A1 | 1/2007 | Rubenfield et al. | |
| 2007/0243526 A1 | 10/2007 | Kay et al. | |
| 2008/0311627 A1 | 12/2008 | Tetzner et al. | |
| 2009/0270480 A1 | 10/2009 | Amegadzie et al. | |
| 2012/0164205 A1 | 6/2012 | Baum et al. | |
| 2014/0336245 A1 | 11/2014 | Mingozzi et al. | |
| 2017/0021038 A1 | 1/2017 | Pan et al. | |
| 2017/0166926 A1 | 6/2017 | Deverman et al. | |
| 2017/0183647 A1 | 6/2017 | Chavez et al. | |

(Continued)

FOREIGN PATENT DOCUMENTS

| | | |
|---|---|---|
| CN | 101883859 | 11/2010 |
| CN | 109207520 | 1/2019 |

(Continued)

OTHER PUBLICATIONS

Office Action in Japanese Appln. No. 2021-557657, dated Mar. 5, 2024, 14 pages (with English translation).
GenBank Accession No. KAA0147029.1, "hypothetical protein FNF29_07656 [Cafeteria roenbergensis]," dated Sep. 9, 2019, 2 pages.
International Search Report and Written Opinion in International Appln. No. PCT/US2022/026608, mailed on Oct. 12, 2022, 13 pages.
Abelson et al., Methods in Enzymology, 2004, Academic Press, Eds., 971 pages.
Ahmad et al., "Mutations of the protocadherin gene PCDH15 cause Usher syndrome type IF," Am J Hum Genet., Jul. 2001, 69(1):25-34.

(Continued)

*Primary Examiner* — Gregory S Emch
*Assistant Examiner* — Estella M. Gustilo
(74) *Attorney, Agent, or Firm* — Fish & Richardson P.C.

(57) ABSTRACT

Engineered AAV vectors for transgene expression, e.g., in the CNS, PNS, inner ear, heart, or retina, and methods of use thereof. Also provided are methods for discovering new engineered AAV vectors that mediate transgene expression in desired cell types.

2 Claims, 39 Drawing Sheets

Specification includes a Sequence Listing.

(56) References Cited

U.S. PATENT DOCUMENTS

| | | | |
|---|---|---|---|
| 2017/0240885 | A1 | 8/2017 | Deverman et al. |
| 2018/0187213 | A1 | 7/2018 | High et al. |
| 2018/0282382 | A1 | 10/2018 | Alagramam |
| 2021/0079406 | A1 | 3/2021 | Maguire et al. |
| 2022/0119475 | A1 | 4/2022 | Corey et al. |

FOREIGN PATENT DOCUMENTS

| | | | | |
|---|---|---|---|---|
| JP | 2008-263851 | | 11/2008 | |
| RU | 2611202 | | 2/2017 | |
| RU | 2018128780 | | 12/2018 | |
| WO | WO 1998/000041 | | 1/1998 | |
| WO | WO 1998/010088 | | 3/1998 | |
| WO | WO 2003/097685 | | 11/2003 | |
| WO | WO 2004/112727 | A2 | 12/2004 | |
| WO | WO 2006/119432 | | 11/2006 | |
| WO | WO 2011/119484 | A1 | 9/2011 | |
| WO | WO 2015/013148 | | 1/2015 | |
| WO | WO 2015/038958 | | 3/2015 | |
| WO | WO 2015/130840 | | 9/2015 | |
| WO | WO 2016/134375 | A1 | 8/2016 | |
| WO | WO 2017/100791 | | 6/2017 | |
| WO | WO 2017/136536 | | 8/2017 | |
| WO | WO 2018/022608 | | 2/2018 | |
| WO | WO-2018022608 | A2 * | 2/2018 | ............ A61K 48/00 |
| WO | WO 2018/189244 | | 10/2018 | |
| WO | WO 2019/028306 | | 2/2019 | |
| WO | WO 2019/046069 | | 3/2019 | |
| WO | WO-2019169132 | A1 * | 9/2019 | ........... C07K 14/005 |
| WO | WO 2019/200016 | | 10/2019 | |
| WO | WO 2020/014471 | | 1/2020 | |
| WO | WO 2020/028751 | A2 | 2/2020 | |
| WO | WO 2020/077295 | | 4/2020 | |
| WO | WO 2020/097372 | | 5/2020 | |
| WO | WO 2020/160337 | A1 | 8/2020 | |
| WO | WO 2020/198737 | | 10/2020 | |
| WO | WO 2020/210655 | A1 | 10/2020 | |
| WO | WO 2021/067448 | | 4/2021 | |
| WO | WO 2022/232327 | | 11/2022 | |

OTHER PUBLICATIONS

Ahmad et al., "PCDH15 is expressed in the neurosensory epithelium of the eye and ear and mutant alleles are responsible for both USHIF and DFNB23," Hum Mol Genet., Dec. 2003, 12(24):3215-23.
Ahmad et al., "Restoration of connexin26 protein level in the cochlea completely rescues hearing in a mouse model of human connexin30-linked deafness," Proc Natl Acad Sci U S A, Jan. 2007, 104(4):1337-41.
Akil et al., "Restoration of hearing in the VGLUT3 knockout mouse using virally mediated gene therapy," Neuron, Jul. 2012, 75(2):283-93.
Alagramam et al., "Mutations in protocadherin 15 and cadherin 23 affect tip links and mechanotransduction in mammalian sensory hair cells," PLoS One, Apr. 2011, 6(4):e19183, 16 pages.
Al-Moyed et al., "A dual-AAV approach restores fast exocytosis and partially rescues auditory function in deaf otoferlin knock-out mice, " EMBO Mol Med., Jan. 2019, 11(1):e9396, 13 pages.
Angueyra et al., "Leveraging Zebrafish to Study Retinal Degeneration," Front Cell Dev Biol., Sep. 2018, 6:110, 19 pages.
Araya-Secchi et al., "An elastic element in the protocadherin-15 tip link of the inner ear," Nat Commun., Nov. 2016, 7:13458, 14 pages.
Assad et al., "An active motor model for adaptation by vertebrate hair cells," J Neurosci., Sep. 1992, 12(9):3291-309.
Assad et al., "Tip-link integrity and mechanical transduction in vertebrate hair cells," Neuron, Dec. 1991, 7(6):985-94.
Azaiez et al., "Genomic Landscape and Mutational Signatures of Deafness-Associated Genes," Am J Hum Genet., Oct. 2018, 103(4):484-497.
Azaiez et al., "GJB2: the spectrum of deafness-causing allele variants and their phenotype," Hum Mutat., Oct. 2004, 24(4):305-11.
Ben-Yosef et al., "A mutation of PCDH15 among Ashkenazi Jews with the type 1 Usher syndrome," N Engl J Med., Apr. 2003, 348(17):1664-70.
Boshart et al., "A very strong enhancer is located upstream of an immediate early gene of human cytomegalovirus," Cell, Jun. 1985, 41(2):521-30.
Boulay et al., "Hearing is normal without connexin30," J Neurosci., Jan. 2013, 33(2):430-4.
Brownstein et al., "The R245X mutation of PCDH15 in Ashkenazi Jewish children diagnosed with nonsyndromic hearing loss foreshadows retinitis pigmentosa," Pediatr Res., Jun. 2004, 55(6): 995-1000.
Buenrostro et al., "Transposition of native chromatin for fast and sensitive epigenomic profiling of open chromatin, DNA-binding proteins and nucleosome position," Nat Methods, Dec. 2013, 10(12):1213-8.
Chamberlain et al., "Progress toward Gene Therapy for Duchenne Muscular Dystrophy," Mol Ther., 2017, 25:1125-31.
Chan et al., "Engineered AAVs for efficient noninvasive gene delivery to the central and peripheral nervous systems," HHS Public Access Author Manuscript, published online Dec. 26, 2017; published in final edited form as: Nat Neurosci., Aug. 2017, 20(8):1172-1179.
Chang et al., "Functional studies reveal new mechanisms for deafness caused by connexin mutations," Otol Neurotol., Feb. 2009, 30(2):237-40.
Chang et al., "Gap junction mediated intercellular metabolite transfer in the cochlea is compromised in connexin30 null mice," PloS one, 2008, 3(12):e4088, 10 pages.
Chang et al., "Timed conditional null of connexin26 in mice reveals temporary requirements of connexin26 in key cochlear developmental events before the onset of hearing," Neurobiol Dis., Jan. 2015, 73:418-27.
Chen et al., "Characterization of a knock-in mouse model of the homozygous p. V37I variant in Gjb2," Sci Rep., Sep. 2016, 6:33279, 7 pages.
Chen et al., "Developmental abnormalities in supporting cell phalangeal processes and cytoskeleton in the Gjb2 knockdown mouse model," Dis Model Mech., Feb. 2018, 11(2):dmm033019, 11 pages.
Chen et al., "Down regulated connexin26 at different postnatal stage displayed different types of cellular degeneration and formation of organ of Corti," Biochem Biophys Res Commun., Feb. 2014, 445(1):71-7.
Cheung et al., "$Ca^{2+}$changes the force sensitivity of the hair-cell transduction channel," Biophys J., Jan. 2006, 90(1):124-39.
Chow et al., "Inducible Cre Recombinase Activity in Mouse Cerebellar Granule Cell Precursors and Inner Ear Hair Cells," Dev Dyn., Nov. 2006, 235(11):2991-8.
Christensen et al., "TRP channels in mechanosensation: Direct or indirect activation?," Nat Rev Neurosci., Jul. 2007, 8(7):510-21.
Chu et al., "SV40 DNA transfection of cells in suspension: analysis of efficiency of transcription and translation of T-antigen," Gene, Mar. 1981, 13(2):197-202.
Cohen-Salmon et al., "Targeted ablation of connexin26 in the inner ear epithelial gap junction network causes hearing impairment and cell death," Curr Biol., Jul. 2002, 12(13):1106-11.
Corey et al., "Kinetics of the receptor current in bullfrog saccular hair cells," J Neurosci., May 1983, 3(5):962-76.
Corey et al., "TRPA1 is a candidate for the mechanosensitive transduction channel of vertebrate hair cells," Nature, Dec. 2004, 432(7018):723-30.
Creyghton et al., "Histone H3K27ac separates active from poised enhancers and predicts developmental state," Proc Natl Acad Sci U S A, Dec. 2010, 107(50):21931-6.
Crispino et al., "BAAV mediated GJB2 gene transfer restores gap junction coupling in cochlear organotypic cultures from deaf Cx26Sox10Cre mice," PloS one, 2011, 6(8):e23279, 11 pages.
Crispino et al., "In vivo genetic manipulation of inner ear connexin expression by bovine adeno-associated viral vectors," Sci Rep., Aug. 2017, 7(1):6567, 13 pages.

(56) References Cited

OTHER PUBLICATIONS

Dai et al., "Rhesus Cochlear and Vestibular Functions Are Preserved After Inner Ear Injection of Saline Volume Sufficient for Gene Therapy Delivery," J Assoc Res Otolaryngol., Aug. 2017, 18(4):601-617.
Darcy et al., "Abstract 691: Dual adeno-associated viral Anc80 vector efficiently transduces inner ear cells in non-human primates," Abstract, Presented at the 43rd Annual MidWinter Meeting, San Jose, CA, Jan. 25-29, 2020, 43:447-48, 3 pages.
De Felipe et al., "Tricistronic and tetracistronic retroviral vectors for gene transfer," Hum Gene Ther., Sep. 2000, 11(13):1921-31.
De Felipe et al., "Use of the 2A sequence from foot-and-mouth disease virus in the generation of retroviral vectors for gene therapy," Gene Ther., Feb. 1999, 6(2):198-208.
Degen et al., "Connexin32 can restore hearing in connexin26 deficient mice," Eur J Cell Biol., Oct. 2011, 90(10):817-24.
del Castillo et al., "A novel deletion involving the connexin-30 gene, del(GJB6-d13s1854), found in trans with mutations in the GJB2 gene (connexin-26) in subjects with DFNB1 non-syndromic hearing impairment," J Med Genet., Jul. 2005, 42(7):588-94.
del Castillo et al., "DFNB1 Non-syndromic Hearing Impairment: Diversity of Mutations and Associated Phenotypes," Front Mol Neurosci., Dec. 2017, 10:428.
Delmaghani et al., "Inner ear gene therapies take off: current promises and future challenges," J Clin Med., Jul. 2020, 9(7):2309.
Derby et al., "Gene transfer into the mammalian inner ear using HSV-1 and vaccinia virus vectors," Hear Res., Aug. 1999, 134(1-2):1-8.
Dinculescu et al., "AAV-Mediated Clarin-1 Expression in the Mouse Retina: Implications for USH3A Gene Therapy," PLOS One, Feb. 2016, 11(2):e0148874.
Dinh et al., "Diverse deafness mechanisms of connexin mutations revealed by studies using in vitro approaches and mouse models," Brain Res., Jun. 2009, 1277:52-69.
Doane et al., "Regulatory elements in molecular networks," Wiley Interdiscip Rev Syst Biol Med., May 2017, 9(3):10.1002/wsbm.1374, 13 pages.
Doucette et al., "Profound, prelingual nonsyndromic deafness maps to chromosome 10q21 and is caused by a novel missense mutation in the Usher syndrome type IF gene PCDH15," Eur J Hum Genet., May 2009, 17(5):554-64.
Dulon et al., "Clarin-1 gene transfer rescues auditory synaptopathy in model of Usher syndrome," J Clin Invest., Aug. 2018, 128(8):3382-3401.
Dyka et al., "Dual adeno-associated virus vectors result in efficient in vitro and in vivo expression of an oversized gene, MYO7A," Hum Gene Ther Methods, Apr. 2014, 25(2):166-77.
Ellis et al., "A survey of ex vivo/in vitro transduction efficiency of mammalian primary cells and cell lines with Nine natural adeno-associated virus (AAV1-9) and one engineered adeno-associated virus serotype," Virol J., Mar. 2013, 10:74.
Extended European Search Report for Application No. EP 19785415.1, mailed Dec. 15, 2021, 11 pages.
Feigenspan et al., "Expression of connexin36 in cone pedicles and OFF-cone bipolar cells of the mouse retina," J Neurosci., Mar. 2004, 24(13):3325-34.
Fetoni et al., "Cx26 partial loss causes accelerated presbycusis by redox imbalance and dysregulation of Nfr2 pathway," Redox Biol., Oct. 2018, 19:301-317.
Fields et al., "Usher syndrome type III: revised genomic structure of the USH3 gene and identification of novel mutations," Am J Hum Genet., Sep. 2002, 71(3):607-17.
Fisher et al., "Transduction with recombinant adeno-associated virus for gene therapy is limited by leading-strand synthesis," J Virol., Jan. 1996, 70(1):520-32.
Forge et al., "Gap junctions and connexin expression in the inner ear," Novartis Found Symp., 1999, 219:134-50.
Forge et al., "Gap junctions in the inner ear: comparison of distribution patterns in different vertebrates and assessment of connexin composition in mammals," J Comp Neurol., Dec. 2003, 467(2):207-31.
Furler et al., "Recombinant AAV vectors containing the foot and mouth disease virus 2A sequence confer efficient bicistronic gene expression in cultured cells and rat substantia nigra neurons," Gene Ther., Jun. 2001, 8(11):864-73.
Garcia et al., "Localization of myosin-Iβ near both ends of tip links in frog saccular hair cells," J Neurosci., Nov. 1998, 18(21):8637-47.
Gaudelli et al., "Programmable base editing of A•T to G•C in genomic DNA without DNA cleavage," Nature, Nov. 2017, 551(7681):464-471.
Ge et al., "Structure of mouse protocadherin 15 of the stereocilia tip link in complex with LHFPL5," eLife, Aug. 2018, 7:e38770, 24 pages.
GenBank Accession No. AAM88774.1., "clarin-1 [*Homo sapiens*]," dated Aug. 5, 2002, 1 page.
Genbank Accession No. NM_004004.6., "*Homo sapiens* gap junction protein beta 2 (GJB2), mRNA," dated Dec. 20, 2021, 4 pages.
Genbank Accession No. NP_001182723.1, "clarin-1 isoform d [*Homo sapiens*]," dated Oct. 11, 2020, 3 pages.
Genbank Accession No. NP_001243748.1, clarin-1 isoform e [*Homo sapiens*], dated Dec. 13, 2020, 3 pages.
Genbank Accession No. NP_443721.1, clarin-1 isoform c [*Homo sapiens*], dated Oct. 10, 2020, 3 pages.
Genbank Accession No. NP_700433.1, clarin-1 isoform 1 [Mus musculus], dated Oct. 7, 2020, 3 pages.
Genbank Accession No. NP_700434.1, "clarin-1 isoform 2 [Mus musculus]," dated Oct. 9, 2020, 4 pages.
Genbank Accession No. NP_700435.1, "clarin-1 isoform 3 [Mus musculus]," dated Oct. 10, 2020, 3 pages.
Genbank Accession No. NP_777367.1, "clarin-1 isoform a [Homo sapiens]," dated Dec. 14, 2020, 3 pages.
Geng et al., "Modeling and Preventing Progressive Hearing Loss in Usher Syndrome III," Sci Rep., Oct. 2017, 7(1):13480, 15 pages.
Gossen et al., "Tight control of gene expression in mammalian cells by tetracycline-responsive promoters," Proc Natl Acad Sci U S A, Jun. 1992, 89(12):5547-51.
Gossen et al., "Transcriptional activation by tetracyclines in mammalian cells," Science, Jun. 1995, 268(5218):1766-9.
Graham et al., "A new technique for the assay of infectivity of human adenovirus 5 DNA," Virology, Apr. 1973, 52(2):456-67.
Gregorevic et al., "rAAV6-microdystrophin preserves muscle function and extends lifespan in severely dystrophic mice," Nat Med., Jul. 2006, 12(7):787-9.
Grimm et al., "In vitro and in vivo gene therapy vector evolution via multispecies interbreeding and retargeting of adeno-associated viruses," J Virol., Jun. 2008, 82(12):5887-911.
György et al., "Allele-specific gene editing prevents deafness in a model of dominant progressive hearing loss," Nat Med., Jul. 2019, 25(7):1123-1130.
György et al., "An AAV9 capsid variant efficiently transduces inner ear hair cells in mice and non-human primates and rescues hearing in a mouse model of human deafness," Mol Ther Methods Clin Dev., Nov. 2018, 13:1-13.
György et al., "Rescue of Hearing by Gene Delivery to Inner-Ear Hair Cells Using Exosome-Associated AAV," Mol Ther., Feb. 2017, 25(2):379-391.
Halpin et al., "Self-processing 2A-polyproteins—a system for co-ordinate expression of multiple proteins in transgenic plants," Plant J., Feb. 1999, 17(4):453-9.
Hanlon et al., "151: AAV-S: A Novel AAV Vector Selected in Brain Transduces the Cochlea with High Efficiency," Abstract, Presented at Proceedings of the 2020 American Society of Gene and Cell Therapy Annual Meeting, Virtual, May 12-15, 2020; Molecular Therapy, Apr. 2020, 28(4S1):76-77, 2 pages.
Hanlon et al., "AAV-S: A novel AAV vector selected in brain transduces the inner ear with high efficiency," Poster, Presented at Proceedings of the ASGCT, Harvard Medical School, Boston, MA, Apr. 28, 2020, 1 page.
Harvey et al., "Inducible control of gene expression: prospects for gene therapy," Curr Opin Chem Biol., Aug. 1998, 2(4):512-8.

(56) References Cited

OTHER PUBLICATIONS

Hasson et al., "Unconventional myosins in inner-ear sensory epithelia," J Cell Biol., Jun. 1997, 137(6):1287-307.
Hirsch et al., "Delivering Transgenic DNA Exceeding the Carrying Capacity of AAV Vectors," Methods Mol Biol., 2016, 1382:21-39.
Holt et al., "A chemical-genetic strategy demonstrates myosin 1c mediates sensory adaptation in hair cells," Cell, Feb. 2002, 108(3):371-81.
Holt et al., "Functional expression of exogenous proteins in mammalian sensory hair cells infected with adenoviral vectors," J Neurophysiol., Apr. 1999, 81(4):1881-8.
Hrvatin et al., "Single-cell analysis of experience-dependent transcriptomic states in the mouse visual cortex," Nat Neurosci., Jan. 2018, 21(1):120-129.
Huang et al., "Role of the hepatitis B virus posttranscriptional regulatory element in export of intronless transcripts, " Mol Cell Biol., 1995, 15(7):3864-3869.
Iizuka et al., "Perinatal Gjb2 gene transfer rescues hearing in a mouse model of hereditary deafness," Hum Mol Genet., Jul. 2015, 24(13):3651-61.
Indzhykulian et al., "Molecular remodeling of tip links underlies mechanosensory regeneration in auditory hair cells," PLoS Biol., 2013, 11(6):e1001583, 15 pages.
International Preliminary Report on Patentability for Application No. PCT/US2019/026852, mailed Oct. 22, 2020, 8 pages.
International Preliminary Report on Patentability for Application No. PCT/US2021/050205, mailed Mar. 23, 2023, 10 pages.
International Search Report and Written Opinion for Application No. PCT/US2019/026852, mailed Jul. 10, 2019, 15 pages.
International Search Report and Written Opinion for Application No. PCT/US2021/050205, mailed Dec. 20, 2021, 16 pages.
Iossa et al., "GJB2 Gene Mutations in Syndromic Skin Diseases with Sensorineural Hearing Loss," Curr Genomics, Nov. 2011, 12(7):475-785.
Isgrig et al., "AAV2.7m8 is a powerful viral vector for inner ear gene therapy," Nat Commun., Jan. 2019, 10(1):427, 8 pages.
Ivanchenko et al., "4: Preclinical testing of AAV9-PHP.B for transgene expression in the non-human primate cochlea," Abstract, Presented at Proceedings of the 2020 American Society of Gene and Cell Therapy Annual Meeting, Virtual, May 12-15, 2020; Molecular Therapy, Apr. 2020, 28(4S1):2, 1 page.
Ivanchenko et al., "AAV-S: A versatile capsid variant for transduction of mouse and primate inner ear," Mol Ther Methods Clin Dev., Mar. 2021, 21:382-398.
Ivanchenko et al., "Preclinical testing of AAV9-PHP.B for transgene expression in the non-human primate cochlea," Hear Res., Sep. 2020, 394:107930, 11 pages.
Johnson et al., "Connexin-Mediated Signaling in Nonsensory Cells Is Crucial for the Development of Sensory Inner Hair Cells in the Mouse Cochlea," J Neurosci., Jan. 2017, 37(2):258-268.
Jovičić et al., "Comprehensive Expression Analyses of Neural Cell-Type-Specific miRNAs Identify New Determinants of the Specification and Maintenance of Neuronal Phenotypes," J Neurosci., Mar. 2013, 33(12):5127-37.
Kamiya et al., "Assembly of the cochlear gap junction macromolecular complex requires connexin 26," J Clin Invest., Apr. 2014, 124(4):1598-607.
Kazmierczak et al., "Cadherin 23 and protocadherin 15 interact to form tip-link filaments in sensory hair cells," Nature, Sep. 2007, 449(7158):87-91.
Kelsell et al., "Connexin 26 mutations in hereditary non-syndromic sensorineural deafness," Nature, May 1997, 387(6628):80-3.
Kenna et al., "Audiologic phenotype and progression in GJB2 (Connexin 26) hearing loss," Arch Otolaryngol Head Neck Surg., Jan. 2010, 136(1):81-7.
Keppeler et al., "Ultrafast optogenetic stimulation of the auditory pathway by targeting-optimized Chronos," EMBO J, Dec. 2018, 37(24):e99649, 15 pages.
Kiang et al., "Upstream genomic sequence of the human connexin26 gene," Gene, Oct. 1997, 199(1-2):165-71.
Kikuchi et al., "Gap junction systems in the mammalian cochlea," Brain Res Brain Res Rev., Apr. 2000, 32(1):163-6.
Kikuchi et al., "Gap junctions in the rat cochlea: immunohistochemical and ultrastructural analysis," Anat Embryol (Berl)., Feb. 1995, 191(2):101-18.
Klump et al., "Retroviral vector-mediated expression of HoxB4 in hematopoietic cells using a novel coexpression strategy," Gene Ther., May 2001, 8(10):811-7.
Kodippili et al., "Dual AAV Gene Therapy for Duchenne Muscular Dystrophy with a 7-kb Mini-Dystrophin Gene in the Canine Model," Hum Gene Ther., Mar. 2018, 29(3):299-311.
Koehler et al., "Generation of inner ear organoids containing functional hair cells from human pluripotent stem cells," Nat Biotechnol., Jun. 2017, 35(6):583-589.
Kohrman et al., "Gene therapy for deafness," Gene Ther., Dec. 2013, 20(12):1119-23.
Kwan et al., "TRPA1 contributes to cold, mechanical, and chemical nociception but is not essential for hair-cell transduction," Neuron, Apr. 2006, 50(2):277-89.
Landegger et al., "A synthetic AAV vector enables safe and efficient gene transfer to the mammalian inner ear," Nat Biotechnol., Mar. 2017, 35(3):280-284.
Lang et al., "Effects of chronic furosemide treatment and age on cell division in the adult gerbil inner ear," J Assoc Res Otolaryngol., Jun. 2003, 4(2):164-75.
Lee et al., "Efficient viral transduction in mouse inner ear hair cells with utricle injection and AAV9-PHP.B," Hear Res., Sep. 2020, 394:107882, 11 pages.
Lee et al., "Mice with conditional deletion of Cx26 exhibit no vestibular phenotype despite secondary loss of Cx30 in the vestibular end organs," Hearing Res., Oct. 2015, 328:102-12.
Levy et al., "Cytosine and adenine base editing of the brain, liver, retina, heart and skeletal muscle of mice via adeno-associated viruses," Nat Biomed Eng., Jan. 2020, 4(1):97-110.
Li et al., "Characterization of slow-cycling cells in the mouse cochlear lateral wall," PloS one, Jun. 2017, 12(6):e0179293.
Li et al., "MicroRNAs in hair cell development and deafness," Curr Opin Otolaryngol Head Neck Surg., Oct. 2010, 18(5):459-65.
Li et al., "Notch inhibition induces mitotically generated hair cells in mammalian cochleae via activating the Wnt pathway," Proc Natl Acad Sci U S A, Jan. 2015, 112(1):166-71.
Lin et al., "Hearing loss and incident dementia," Arch Neurol., Feb. 2011, 68(2):214-20.
Lin et al., "Hearing loss prevalence in the United States," Arch Intern Med., Nov. 2011, 171(20):1851-2.
Lukashkina et al., "Amplification mode differs along the length of the mouse cochlea as revealed by connexin 26 deletion from specific gap junctions," Sci Rep., Jul. 2017, 7(1):5185, 11 pages.
Lustig et al., "Cochlear Gene Therapy," Cold Spring Harb Perspect Med., Sep. 2019, 9(9):a033191, 15 pages.
Ma et al., "Abstract 404: Connexin 26 in mature ears influences survival of hair cells and neurons," Abstract, Presented at Proceedings of the 43rd Annual MidWinter Meeting, San Jose, CA, Jan. 25-29, 2020, 43:258-9, 3 pages.
Magari et al., "Pharmacologic control of a humanized gene therapy system implanted into nude mice," J Clin Invest., Dec. 1997, 100(11):2865-72.
Maguire et al., "Efficacy, Safety, and Durability of Voretigene Neparvovec-rzyl in RPE65 Mutation-Associated Inherited Retinal Dystrophy: Results of Phase 1 and 3 Trials," Ophthalmology, Sep. 2019, 126(9):1273-1285.
Mahendrasingam et al., "Subcellular distribution and relative expression of fibrocyte markers in the CD/1 mouse cochlea assessed by semiquantitative immunogold electron microscopy," J Histochem Cytochem., Nov. 2011, 59(11):984-1000.
Mammano et al., "Inner Ear Connexin Channels: Roles in Development and Maintenance of Cochlear Function," Cold Spring Harb Perspect Med., Jul. 2019, 9(7):a033233, 26 pages.
Mason et al., "Universal infant hearing screening by automated auditory brainstem response measurement," Pediatrics, Feb. 1998, 101(2):221-8.

(56) References Cited

OTHER PUBLICATIONS

Matsuzaki et al., "Intravenous administration of the adeno-associated virus-PHP.B capsid fails to upregulate transduction efficiency in the marmoset brain," Neurosci Lett., Feb. 2018, 665:182-188.
Mattion et al., "Foot-and-mouth disease virus 2A protease mediates cleavage in attenuated Sabin 3 poliovirus vectors engineered for delivery of foreign antigens," J Virol., Nov. 1996, 70(11):8124-7.
McCarthy, "Self-complementary AAV vectors; advances and applications," Mol Ther., Oct. 2008, 16(10):1648-56.
McLean et al., "GREAT improves functional interpretation of cis-regulatory regions," Nat Biotechnol., May 2010, 28(5):495-501.
Mei et al., "A deafness mechanism of digenic Cx26 (GJB2) and Cx30 (GJB6) mutations: Reduction of endocochlear potential by impairment of heterogeneous gap junctional function in the cochlear lateral wall," Neurobiol Dis., Dec. 2017, 108:195-203.
Mutai et al., "Mitotic activity and specification of fibrocyte subtypes in the developing rat cochlear lateral wall," Neuroscience, Nov. 2009, 163(4):1255-63.
Narui et al., "Tuning Inner-Ear Tip-Link Affinity Through Alternatively Spliced Variants of Protocadherin-15," Biochemistry, Mar. 2018, 57(11):1702-1710.
Nickel et al., "Gap junctions and connexins in the inner ear: their roles in homeostasis and deafness," Curr Opin Otolaryngol Head Neck Surg., Oct. 2008, 16(5):452-7.
Niwa et al., "In vitro polyadenylation is stimulated by the presence of an upstream intron," Genes Dev., Sep. 1990, 4(9):1552-9.
No et al., "Ecdysone-inducible gene expression in mammalian cells and transgenic mice," Proc Natl Acad Sci U S A, Apr. 1996, 93(8):3346-3351.
Office Action in Chinese Appln. No. 202080038934.8, dated Aug. 26, 2023, 11 pages (with English translation).
Office Action in Russian Appln. No. 2021131423, dated Aug. 8, 2023, 11 pages (with English translation).
Office Action in Singapore Appln. No. 11202110165X, dated Aug. 16, 2023, 12 pages.
Olson et al., "Post-translational tools expand the scope of synthetic biology," Curr Opin Chem Biol., Aug. 2012, 16(3-4):300-6.
Pan et al., "Gene therapy restores auditory and vestibular function in a mouse model of Usher syndrome type lc," Nat Biotechnol., Mar. 2017, 35(3):264-272.
Pepermans et al., "The CD2 isoform of protocadherin-15 is an essential component of the tip-link complex in mature auditory hair cells," EMBO Mol Med., Jul. 2014, 6(7):984-92.
Powers et al., "A Partial Calcium-Free Linker Confers Flexibility to Inner-Ear Protocadherin-15," Structure, Mar. 2017, 25(3):482-495.
Rada-Iglesias et al., "A unique chromatin signature uncovers early developmental enhancers in humans," Nature, Feb. 2011, 470(7333):279-83.
Rees et al., "Base editing: precision chemistry on the genome and transcriptome of living cells," Nat Rev Genet., Dec. 2018, 19(12):770-788.
Rodriguez-Paris et al., "Comparative functional characterization of novel non-syndromic GJB2 gene variant p.Gly45Arg and lethal syndromic variant p.Gly45Glu," PeerJ, Oct. 2016, 4:e2494, 18 pages.
Ross, "Comments on the article "Persistent confusion of total entropy and chemical system entropy in chemical thermodynamics" [(1996) Proc. Natl. Acad. Sci. USA 93, 7452-7453]," Proc. Natl Acad Sci USA, Dec. 1996, 93(25):14314.
Ryan et al., "Foot-and-mouth disease virus 2A oligopeptide mediated cleavage of an artificial polyprotein," EMBO J., Feb. 1994, 13(4):928-33.
Sacheli et al., "Gene transfer in inner ear cells: a challenging race," Gene Ther., Mar. 2013, 20(3):237-47.
Scheffer et al., "Gene expression profiling identifies Hes6 as a transcriptional target of ATOH1 in cochlear hair cells, " FEBS Lett., Oct. 2007, 581(24):4651-6.
Scheffer et al., "The α1 subunit of nicotinic acetylcholine receptors in the inner ear: transcriptional regulation by ATOH1 and co-expression with the γ subunit in hair cells," J Neurochem., Dec. 2007, 103(6):2651-64.
Scheffer et al., "XIRP2, an actin-binding protein essential for inner ear hair-cell stereocilia," Cell Rep., Mar. 2015, 10(11):1811-8.
Senís et al., "CRISPR/Cas9-mediated genome engineering: an adeno-associated viral (AAV) vector toolbox," Biotechnol J., Nov. 2014, 9(11):1402-12.
Shepherd et al., "The extent of adaptation in bullfrog saccular hair cells," J Neurosci., Oct. 1994, 14(10):6217-29.
Shu et al., "Identification of Adeno-Associated Viral Vectors That Target Neonatal and Adult Mammalian Inner Ear Cell Subtypes," Hum Gene Ther., Sep. 2016, 27(9):687-99.
Solc et al., "Molecular cloning of myosins from the bullfrog saccular macula: A candidate for the adaptation motor," Auditory Neurosci., 1994, 1:63-75.
Sotomayor et al., "In search of the hair-cell gating spring: Elastic properties of ankyrin and cadherin repeats," Structure, Apr. 2005, 13(4):669-82.
Sotomayor et al., "Structural determinants of cadherin-23 function in hearing and deafness," Neuron, Apr. 2010, 66(1):85-100.
Sotomayor et al., "Structure of a force-conveying cadherin bond essential for inner-ear mechanotransduction," Nature, Dec. 2012, 492(7427):128-32.
Srinivas et al., "Human diseases associated with connexin mutations," Biochim Biophys Acta Biomembr., Jan. 2018, 1860(1):192-201.
Sun et al., "Connexin30 null and conditional connexin26 null mice display distinct pattern and time course of cellular degeneration in the cochlea," J Comp Neurol., Oct. 2009, 516(6):569-79.
Suzuki et al., "Cochlear gene therapy with ancestral AAV in adult mice: complete transduction of inner hair cells without cochlear dysfunction," Sci Rep., Apr. 2017, 7:45524, 11 pages.
Takada et al., "Connexin 26 null mice exhibit spiral ganglion degeneration that can be blocked by BDNF gene therapy," Hearing Res., Mar. 2014, 309:124-35.
Tao et al., "Delivery of adeno-associated virus vectors in adult mammalian inner-ear cell subtypes without auditory dysfunction," Hum Gene Ther., Apr. 2018, 29(4):492-506.
Trapani et al., "Effective delivery of large genes to the retina by dual AAV vectors," EMBO Mol Med., Feb. 2014, 6(2):194-211.
Trapani et al., "Seeing the Light after 25 Years of Retinal Gene Therapy," Trends Mol Med., Aug. 2018, 24(8):669-681.
Trapani, "Dual AAV Vectors for Stargardt Disease," Methods Mol Biol., 2018, 1715:153-175.
Truong et al., "Development of an intein-mediated split-Cas9 system for gene therapy," Nucleic Acids Res., Jul. 2015, 43(13):6450-8.
Tu et al., "Mapping and characterization of the basal promoter of the human connexin26 gene," Biochim Biophys Acta., Nov. 1998, 1443(1-2):169-81.
Västinsalo et al., "Alternative splice variants of the USH3A gene Clarin 1 (CLRN1)," Eur J Hum Genet., Jan. 2011, 19(1):30-5.
Vogl et al., "Tryptophan-rich basic protein (WRB) mediates insertion of the tail-anchored protein otoferlin and is required for hair cell exocytosis and hearing," EMBO J., Dec. 2016, 35(23):2536-2552.
Wan et al., "Inner ear supporting cells: Rethinking the silent majority," Semin Cell Dev Biol., May 2013, 24(5):448-59.
Wang et al., "A Rationally Engineered Capsid Variant of AAV9 for Systemic CNS-Directed and Peripheral Tissue-Detargeted Gene Delivery in Neonates," Mol Ther Methods Clin Dev., Mar. 2018, 9:234-246.
Wang et al., "Ligand-inducible and liver-specific target gene expression in transgenic mice," Nat Biotechnol., Mar. 1997, 15(3):239-43.
Wang et al., "Positive and negative regulation of gene expression in eukaryotic cells with an inducible transcriptional regulator," Gene Ther., May 1997, 4(5):432-41.
Wang et al., "Targeted connexin26 ablation arrests postnatal development of the organ of Corti," Biochem Biophys Res Commun., Jul. 2009, 385(1):33-7.

(56) References Cited

OTHER PUBLICATIONS

Wassmer et al., "Exosome-associated AAV2 vector mediates robust gene delivery into the murine retina upon intravitreal injection," Sci Rep., Mar. 2017, 7:45329, 10 pages.
Watanabe et al., "Expression of the Sox10 gene during mouse inner ear development," Brain Res Mol Brain Res., Dec. 2000, 84(1-2):141-5.
Wilch et al., "A novel DFNB1 deletion allele supports the existence of a distant cis-regulatory region that controls GJB2 and GJB6 expression," Clin Genet., Sep. 2010, 78(3):267-74.
Wingard et al., "Cellular and Deafness Mechanisms Underlying Connexin Mutation-Induced Hearing Loss—A Common Hereditary Deafness," Front Cell Neurosci., May 2015, 9:202, 13 pages.
Wise et al., "The effect of deafness duration on neurotrophin gene therapy for spiral ganglion neuron protection," Hearing Res., Aug. 2011, 278(1-2):69-76.
Wright et al., "Identification of factors that contribute to recombinant AAV2 particle aggregation and methods to prevent its occurrence during vector purification and formulation," Mol Ther., Jul. 2005, 12(1):171-8.
Wu et al., "Hair-cell mechanotransduction persists in TRP channel knockout mice," PloS One, May 2016, 11(5):e0155577, 22 pages.
Xia et al., "Expression of connexin 26 and Na,K-ATPase in the developing mouse cochlear lateral wall: functional implications," Brain Res., Oct. 1999, 846(1):106-11.
Yang et al., "Gfi1-Cre knock-in mouse line: A tool for inner ear hair cell-specific gene deletion," Genesis, Jun. 2010, 48(6):400-6.
Yeh et al., "Abstract PS 172: In vivo base editing rescues hearing in a mouse model of recessive deafness," Abstract, Presented at Proceedings of the 43rd Annual MidWinter Meeting, San Jose, CA, Jan. 25-29, 2020, 43:96-7; 3 pages.
Yeh et al., "In vivo base editing of post-mitotic sensory cells," Nature Commun., Jun. 2018, 9(1):2184, 10 pages.
Yu et al., "Supplementary Figure 2 to: Virally expressed connexin26 restores gap junction function in the cochlea of conditional Gjb2 knockout mice," Gene Ther., Nov. 2013, 1 page.
Yu et al., "Virally expressed connexin26 restores gap junction function in the cochlea of conditional Gjb2 knockout mice," Gene Ther., Jan. 2014, 21(1):71-80.
Zallocchi et al., "Localization and expression of clarin-1, the C1rn1 gene product, in auditory hair cells and photoreceptors," Hear Res., Sep. 2009, 255(1-2):109-20.
Zelante et al., "Connexin26 mutations associated with the most common form of non-syndromic neurosensory autosomal recessive deafness (DFNB1) in Mediterraneans," Hum Mol Genet., Sep. 1997, 6(9):1605-9.
Zhu et al., "Active cochlear amplification is dependent on supporting cell gap junctions," Nature Commun., 2013, 4:1786, 8 pages.
Partial European Search Report in European Appln. No. 20779113.8, dated Nov. 23, 2022, 12 pages.
Extended European Search Report in European Appln. No. 20779113.8, dated Apr. 18, 2023, 13 pages.
Akil et al., "Dual AAV-mediated gene therapy restores hearing in a DFNB9 mouse model," Proc. Natl. Acad. Sci. U S A, Mar. 2019, 116(10):4496-4501.
Al-Zaidy et al., "VXS-101 (Onasemnogene Abeparvovec) for SMA 1 : Comparative Study with a Prospective Natural History Cohort," J. Neuromuscul. Dis., 2019, 6(3):307-317.
Aurnhammer et al., "Universal real-time PCR for the detection and quantification of adeno-associated virus serotype 2-derived inverted terminal repeat sequences," Hum Gene Ther Methods, Feb. 2012, 23(1):18-28.
Berry and Asokan, "Cellular transduction mechanisms of adeno-associated viral vectors," Curr Opin Virol, Dec. 2016, 21:54-60.
Caron et al., "Potent and sustained huntingtin lowering via AAV5 encoding miRNA preserves striatal volume and cognitive function in a humanized mouse model of Huntington disease," Nucleic Acids Res., Jan. 2020, 48(1):36-54.
Cehajic-Kapetanovic et al., "Initial results from a first-in-human gene therapy trial on X-linked retinitis pigmentosa caused by mutations in RPGR," Nat. Med., Mar. 2020, 26(3):354-359, 18 pages.
Chen et al., "Molecular signatures of disease brain endothelia provide new sites for CNS-directed enzyme therapy," Nat Med, Oct. 2009, 15(10):1215-1218.
Christine et al., "Magnetic resonance imaging-guided phase 1 trial of putaminal AADC gene therapy for Parkinson's disease," Ann. Neural., May 2019, 85(5):704-714.
Dashkoff et al., "Tailored transgene expression to specific cell types in the central nervous system after peripheral injection with AAV9," Mol Ther Methods Clin Dev, 2016. 3:16081, 9 pages.
D'Costa et al., "Practical utilization of recombinant AAV vector reference standards: focus on vector genomes titration by free ITR qPCR," Mol Ther Methods Clin Dev, 2016. 5:16019, 9 pages.
Deverman et al., "Cre-dependent selection yields AAV variants for widespread gene transfer to the adult brain," Nat Biotechnol, Feb. 2016, 34(2):204-9, 8 pages.
Duan, "Systemic AAV Micro-dystrophin Gene Therapy for Duchenne Muscular Dystrophy" Mol. Ther., Oct. 2018, 26(10):2337-2356.
Eichler et al., "Hematopoietic stem-cell gene therapy for cerebral adrenoleukodystrophy," N. Engl. J. Med., Oct. 2017, 377(17):1630-1638, 9 pages.
Gong et al., "Adenoassociated virus serotype 9-mediated gene therapy for X-linked adrenoleukodystrophy," Mol. Ther., May 2015, 23(5):824-834.
Gray and Samulski, "Vector design and considerations for CNS applications," Gene Vector Design and Application to Treat Nervous System Disorders, 2011, 9 pages.
Gray et al., "Directed evolution of a novel adeno-associated virus (AAV) vector that crosses the seizure-compromised blood-brain barrier (BBB)," Mol Ther, Mar. 2010, 18(3):570-8.
Griciuc et al., "Alzheimer's disease risk gene CD33 inhibits microglial uptake of amyloid beta," Neuron, May 2013, 78(4):631-43.
György et al., "Gene Transfer with AAV9-PHP.B Rescues Hearing in a Mouse Model of Usher Syndrome 3A and Transduces Hair Cells in a Non-human Primate," Mol Ther Methods Clin Dev, Jun. 2019, 13:1-13.
Hanlon et al., "Selection of an Efficient AAV Vector for Robust CNS Transgene Expression," Molecular Therapy: Methods and Clinical Development, Dec. 2019, 15:320-332.
Hinderer et al., "Severe Toxicity in Nonhuman Primates and Piglets Following High-Dose Intravenous Administration of an Adeno-Associated Virus Vector Expressing Human SMN," Hum Gene Ther, Mar. 2018, 29(3):285-298.
Hordeaux et al., "The GPI-Linked Protein LY6A Drives AAV-PHP.B Transport across the Blood-Brain Barrier," Mol Ther, May 2019, 27(5):912-921.
Hordeaux et al., "The Neurotropic Properties of AAV-PHP.B Are Limited to C57BL/6J Mice," Mol Ther, Mar. 2018, 26(3):664-668.
Hudry et al., "Exosome-associated AAV vector as a robust and convenient neuroscience tool," Gene Ther, 2016, 23(4):380-92.
Hughes et al., "AAV9 intracerebroventricular gene therapy improves lifespan, locomotor function and pathology in a mouse model of Niemann-Pick type C1 disease," Hum. Mol. Genet., Sep. 2018, 27(17):3079-3098.
International Preliminary Report on Patentability in International Appln. No. PCT/US2020/025720, dated Oct. 7, 2021, 7 pages.
International Search Report and Written Opinion in International Appln. No. PCT/US2020/025720, dated Jul. 27, 2020, 10 pages.
Invitation to Pay Additional Fees and, Where Applicable, Protest Fee in International Appln. No. PCT/US2022/026608, mailed on Aug. 15, 2022, 2 pages.
Isgrig et al., "Gene Therapy Restores Balance and Auditory Functions in a Mouse Model of Usher Syndrome," Mol. Ther., Mar. 2017, 25(3):780-791.
Keskin et al., "AAV5-miHTT Lowers Huntingtin mRNA and Protein without Off-Target Effects in Patient- Derived Neuronal Cultures and Astrocytes," Mol. Ther. Methods Clin. Dev., Dec. 2019, 15:275-284.

(56) References Cited

OTHER PUBLICATIONS

Koerber et al., "Construction of diverse adeno-associated viral libraries for directed evolution of enhanced gene delivery vehicles," Nat Protoc, Jul. 2006, 1(2):701-6.
Körbelin et al., "Pulmonary Targeting of Adeno-associated Viral Vectors by Next-generation Sequencing-guided Screening of Random Capsid Displayed Peptide Libraries," Mol Ther, Jun. 2016, 24(6):1050-1061.
Leone et al., "Long-term follow- up after gene therapy for canavan disease," Sci. Transl. Med., 2012, 4(165):165ra163, 14 pages.
Li and Samulski, "Engineering adeno-associated virus vectors for gene therapy," Nature Reviews Genetics, Apr. 2020, 21(4):255-272, 18 pages.
Lopes and Williams, "Gene therapy for the retinal degeneration of usher syndrome caused by mutations in MYO7A," Cold Spring Harb. Perspect. Med., Jun. 2015, 5(6):a017319, 10 pages.
Maguire et al., "Efficacy, Safety, and Durability of Voretigene Neparvovec-rzyl in RPE65 Mutation-Associated Inherited Retinal Dystrophy: Results of Phase 1 and 3 Trials," Ophthalmology, 2019, 126(9):1273-1285.
Maguire et al., Microvesicle-associated AAV vector as a novel gene delivery system. Mol Ther, 2012, 20(5):960-71.
Manno et al., "Successful transduction of liver in hemophilia by AAV-Factor IX and limitations imposed by the host immune response," Nat Med, 2006, 12(3):342-7.
Matsuzaki et al., "Neurotropic Properties of AAV-PHP.B Are Shared among Diverse Inbred Strains of Mice, " Mol Tuer, 2019, 27(4):700-704.
Mendell et al., "Single-Dose Gene-Replacement Therapy for Spinal Muscular Atrophy," N Engl J Med, Nov. 2017, 377(18):1713-1722.
Millington-Ward et al., "Suppression and Replacement Gene Therapy for Autosomal Dominant Disease in a Murine Model of Dominant Retinitis Pigmentosa," Mol. Ther., Apr. 2011, 19(4):642-649.
Mookherjee et al., "Long-term rescue of cone photoreceptor degeneration in retinitis pigmentosa 2 (RP2)-knockout mice by gene replacement therapy," Hum. Mol. Genet., Nov. 2015, 24(22):6446-58.
Nathwani, "Gene therapy for hemophilia," Hematol. Am Soc Hematol Educ Program, Dec. 2019, 2019(1):1-8.
Nist-Lund et al., "Improved TMC1 gene therapy restores hearing and balance in mice with genetic inner ear disorders," Nat. Commun., 2019, 10(1):236, 14 pages.
Nonnenmacher et al., "High capsid-genome correlation facilitates creation of AAV libraries for directed evolution," Mol Ther, Apr. 2015, 23(4):675-82.
Park et al., "Generation of transgenic marmosets expressing genetically encoded calcium indicators," Sci Rep, Oct. 2016, 6:34931, 12 pages.
Paulk et al., "Bioengineered AAV Capsids with Combined High Human Liver Transduction In Vivo and Unique Humoral Seroreactivity," Mol Ther, Jan. 2018, 26(1):289-303.
Paulk et al., "Bioengineered Viral Platform for Intramuscular Passive Vaccine Delivery to Human Skeletal Muscle," Mol Ther Methods Clin Dev, Jul. 2018, 10:144-155.
Pulicherla et al., "Engineering liver-detargeted AAV9 vectors for cardiac and musculoskeletal gene transfer," Mol Ther, Jun. 2011, 19(6):1070-1078.
Remes et al., "AAV-mediated TIMP-1 overexpression in aortic tissue reduces the severity of allograft vasculopathy in mice," J. Hear. Lung Transplant, Apr. 2020, 39(4):389-398, 10 pages.
Sallach et al., "Tropism-modified AAV vectors overcome barriers to successful cutaneous therapy," Mol Ther, May 2014, 22(5):929-39.
Sasaki et al., "Generation of transgenic non-human primates with germline transmission," Nature, May 2009, 459(7246):523-7.
Tan et al., "AAV-ie enables safe and efficient gene transfer to inner ear cells," Nat. Commun., Aug. 2019, 10(1):3733, 10 pages.
Tse et al., "Structure-guided evolution of antigenically distinct adeno-associated virus variants for immune evasion," Proc Natl Acad Sci U S A, May 2017, 114(24):E4812-E4821.
Wan et al., "Efficacy and Safety of rAAV2-ND4 Treatment for Leber's Hereditary Optic Neuropathy," Sci. Rep., Feb. 2016, 6:21587, 10 pages.
Watters et al., "Identification and dynamic regulation of tight junction protein expression in human neural stem cells," Stem Cells Dev, Jun. 2015, 24(12):1377-89.
Xu et al., "A combination of mutations enhances the neurotropism of AAV-2," Virology, 2005, 341:203-214.
Yang et al., "Long-term outcomes of gene therapy for the treatment of Leber's hereditary optic neuropathy," EBioMedicine, Aug. 2016, 10:258-268.
Yu et al., "Nrl knockdown by AAV-delivered CRISPR/Cas9 prevents retinal degeneration in mice," Nat. Commun., Mar. 2017, 8:14716, 15 pages.
Zhang et al., "Cochlear Gene Therapy for Sensorineural Hearing Loss: Current Status and Major Remaining Hurdles for Translational Success," Front. Mol. Neurosci., Jun. 2018, 11:221, 15 pages.
Office Action in Japanese Appln. No. 2021-557657, dated Sep. 24, 2024, 6 pages (with English translation).
Office Action in Chinese Appln. No. 202080038934.8, dated Sep. 7, 2024, 9 pages (with English translation).
Office Action in Russian Appln. No. 2021131423, mailed on Oct. 24, 2024, 6 pages (with English translation).
International Preliminary Report on Patentability in International Appln. No. PCT/US2022/026608, mailed Nov. 9, 2023, 8 pages.
Körbelin et al., "A brain microvasculature endothelial cell-specific viral vector with the potential to treat neurovascular and neurological diseases," EMBO Mol Med., Jun. 2016, 8(6):609-25.
Lang et al., "Standard screening methods underreport AAV-mediated transduction and gene editing," Nat Commun., Jul. 2019, 10(1):3415, 10 pages.
Prabhakar et al., "AAV9 transduction mediated by systemic delivery of vector via retro-orbital injection in newborn, neonatal and juvenile mice," Exp Anim., Nov. 2021, 70(4):450-458.
Ravindra Kumar et al., "Multiplexed Cre-dependent selection yields systemic AAVs for targeting distinct brain cell types," Nat Methods, May 2020, 17(5):541-550.
Xie et al., "MicroRNA-regulated, systemically delivered rAAV9: a step closer to CNS-restricted transgene expression," Mol Ther., Mar. 2011, 19(3):526-35.
Office Action in Russian Appln. No. 2021131423, dated Dec. 21, 2023, 12 pages (with English translation).
Office Action in Chinese Appln. No. 202080038934.8, dated Jun. 27, 2024, 11 pages (with English translation).
Office Action in Australian Appln. No. 2020248116, mailed on Dec. 13, 2024, 6 pages.
Office Action in Singaporean Appln. No. 11202110165X, mailed on Feb. 11, 2025, 3 pages.
Notice of Allowance in Japanese Appln. No. 2021-557657, mailed on Feb. 18, 2025, 6 pages (with English translation).
Notice of Allowance in Russian Appln. No. 2021131423, mailed on Mar. 3, 2025, 15 pages (with English translation).
Office Action in Korean Appln. No. 10-2021-7034532, mailed on Feb. 7, 2025, 12 pages (with English translation).
Naso et al., "Adeno-associated virus (AAV) as a vector for gene therapy," BioDrugs, Aug. 2017, 31(4):317-34.
Partial European Search Report in European Appln. No. 22796682.7, mailed on Apr. 30, 2025, 13 pages.
GenBank Accession No. CDJ33539, "hypothetical protein EMH_0016460 [Eimeria mitis], " Nov. 5, 2013, 1 page.
Office Action in Canadian Appln. No. 3135292, mailed on Aug. 19, 2025, 8 pages.
Extended European Search Report in European Appln. No. 22796682.7, mailed on Jul. 21, 2025, 11 pages.
Notice of Allowance in Korean Appln. No. 10-2021-7034532, mailed on Dec. 3, 2025, 7 pages (with English translation).
Office Action in Australian Appln. No. 2020248116, mailed on Sep. 29, 2025, 4 pages.
Office Action in Israeli Patent Appln. No. 286725, mailed Dec. 16, 2025, 4 pages.

(56) References Cited

OTHER PUBLICATIONS

Office Action in Mexican Patent Appln. No. MX/a/2021/011701, mailed Dec. 2, 2025, 17 pages (with English translation).

* cited by examiner ii. Cell isolation and tdTomato-positive cell sorting
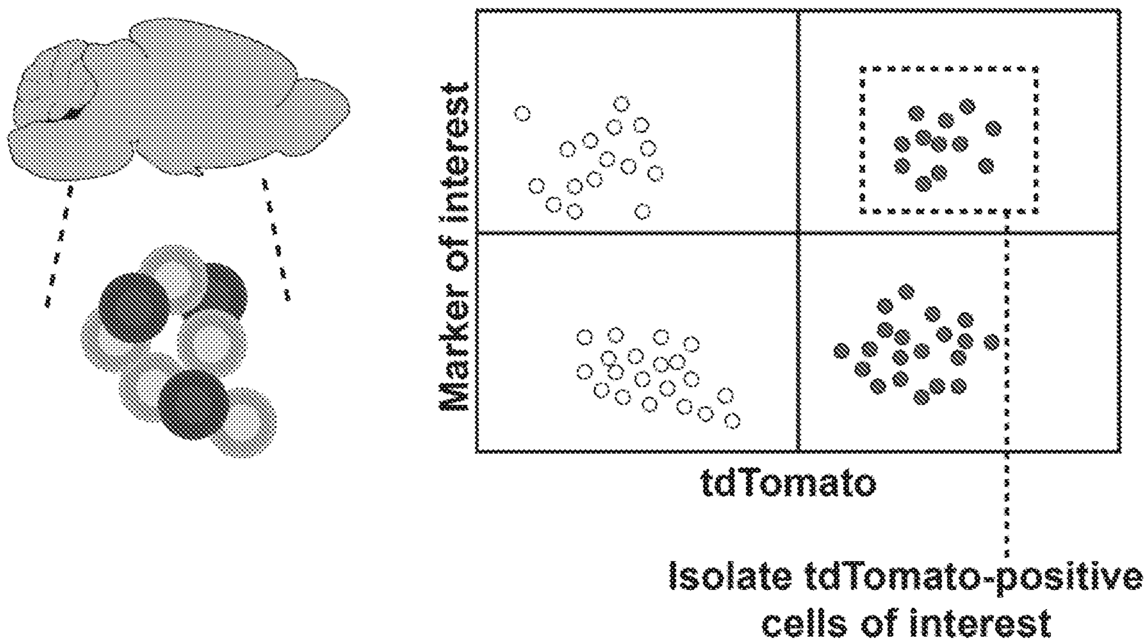
iii. Transduction-comptetent vectors
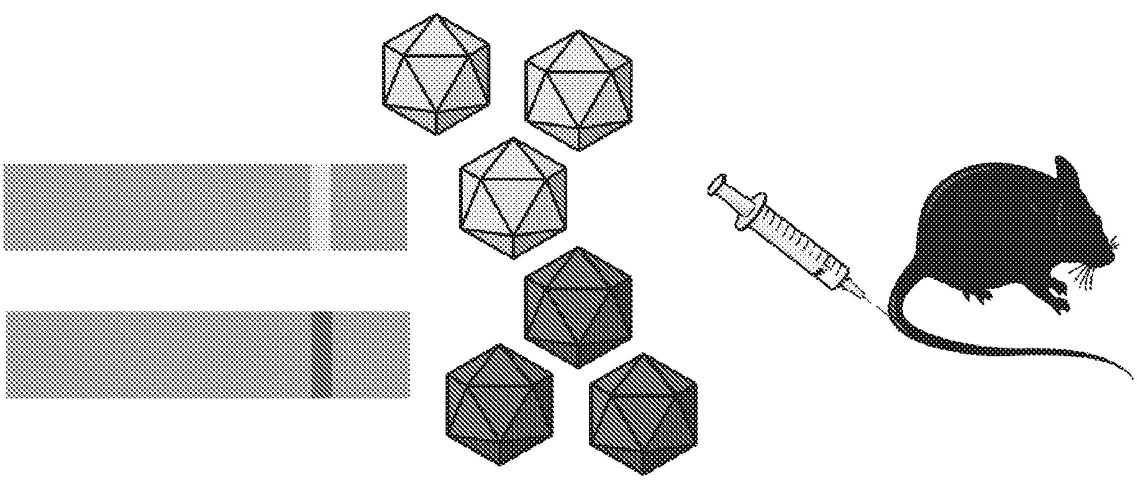
FIG. 1B, continued

| Nucleotide Sequence | SEQ ID NO: | Peptide Sequence | SEQ ID NO: | % of pool |
|---|---|---|---|---|
| CAGCCTCGTCTTACTGAGCTT | 17. | QPRLTEL | 18. | 0.05572947 |
| AGTCATTTTAGTAATTCTATG | 19. | SHFSNSM | 20. | 0.02365472 |
| CCGCCTTCTACGGGGAATCCT | 21. | PPSTGNP | 22. | 0.02328549 |
| AATAGTCTTGGGGTGATGGAT | 23. | NSLGVMD | 24. | 0.02276376 |
| CCTCCTATGGCTACGCCTCAG | 25. | PPMATPQ | 26. | 0.02126276 |
| CCGCATACTCGGGCTGAGCCT | 27. | PHTRAEP | 28. | 0.01834104 |
| GTGAATCAGACTAATTATTCT | 29. | VNQTNYS | 30. | 0.01784338 |
| CATGCGCCGAGGCTGGTTCAG | 31. | HAPRLVQ | 32. | 0.01539524 |
| TGGAGTAAGGAGTCGAATCAT | 33. | WSKESNH | 34. | 0.01529892 |
| ACTACTGCTGGTCCGACTGAG | 35. | TTAGPTE | 36. | 0.01419123 |
| TCGTGGCCGCAGTCGCCTTCG | 37. | SWPQSPS | 38. | 0.0139424 |
| ACTTGTGCTGTTCCGGATCGG | 39. | TCAVPDR | 40. | 0.01326816 |
| CCTCGTGCGGAGCCTCGGACG | 41. | PRAEPRT | 42. | 0.01314776 |
| CCTACTGCGGGTGTGTATCTG | 43. | PTAGVYL | 44. | 0.01308354 |
| CAGTTGAGTAATACGACGTTG | 45. | QLSNTTL | 46. | 0.01285077 |
| CGGATGGATATGGCTGTGAGG | 47. | RMDMAVR | 48. | 0.01261799 |
| CGGCCGCCGCCTGCGACTCCT | 49. | RPPPATP | 50. | 0.01257786 |
| CAGTATCTGTTTCATATTTTT | 51. | QYLFHIF | 52. | 0.01226482 |
| GGTGCTGGGACTCTTACTTCT | 53. | GAGTLTS | 54. | 0.01223271 |
| CCTCTTTCGCGTGTTGCTTTG | 55. | PLSRVAL | 56. | 0.0119277 |
| ACTACTGCTAAGACGACTGGG | 57. | TTAKTTG | 58. | 0.01187954 |
| TCGCTGCCGGCTACTCATGTG | 59. | SLPATHV | 60. | 0.01170295 |
| AGTGAGAAGGTGATTCGGAGT | 61. | SEKVIRS | 62. | 0.01136583 |
| AAGTCGACTATGCGGAAGCCG | 63. | KSTMRKP | 64. | 0.01134977 |
| GTGTCGAAGCAGAATACGACT | 65. | VSKQNTT | 66. | 0.01106081 |
| GCTGATATGACGGGGCCTACT | 67. | ADMTGPT | 68. | 0.01080396 |
| CCTACTCGTGCGACTCCTATT | 69. | PTRATPI | 70. | 0.01057921 |
| TCTTGGCCTGGGCTGTTGCTG | 71. | SWPGLLL | 72. | 0.01055513 |
| TGGAGGCTGGAGCAGTTGAAG | 73. | WRLEQLK | 74. | 0.01037051 |
| CTTCCGAGTTCTCCGGTTTTT | 75. | LPSSPVF | 76. | 0.31919829 |
| CCTCAGCGGCATCAGAATGAT | 77. | PQRHQND | 78. | 0.00414981 |
| TCGATTCCGTTTCGGTATCCG | 79. | SIPFRYP | 80. | 0.03205067 |
| CCTGATGGTCCGCAGGCTCTG | 81. | PDGPQAL | 82. | 0.00370834 |
| TCGACTACGTGGAAGTCTGAT | 83. | STTWKSD | 84. | 0.05475021 |
| TTGCAGAAGATGGCTGTTCCG | 85. | LQKMAVP | 86. | 0.00273711 |
| N/A | | Others | | 0.13220799 |

*FIG. 2A*

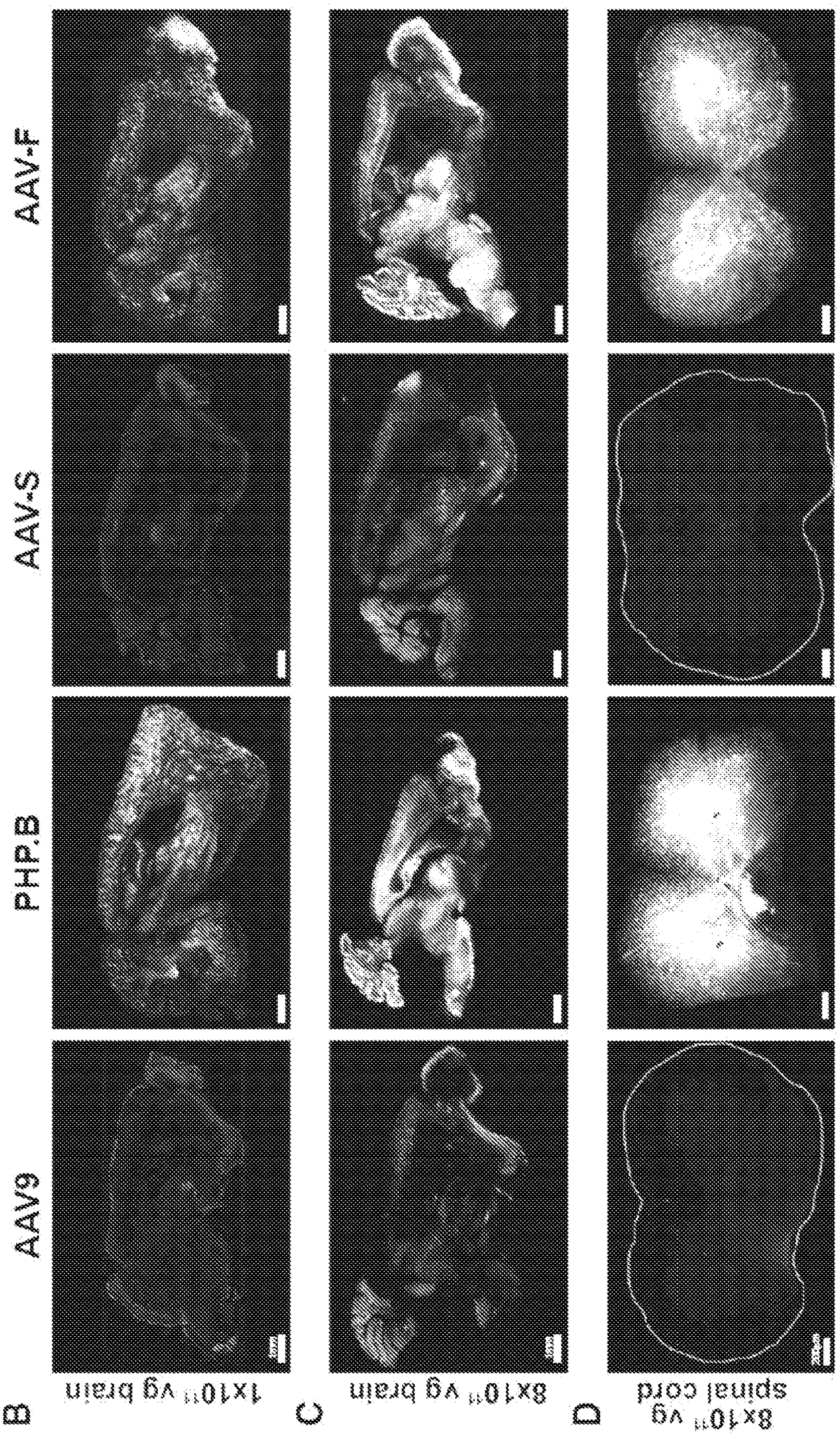
FIGs. 3B-D

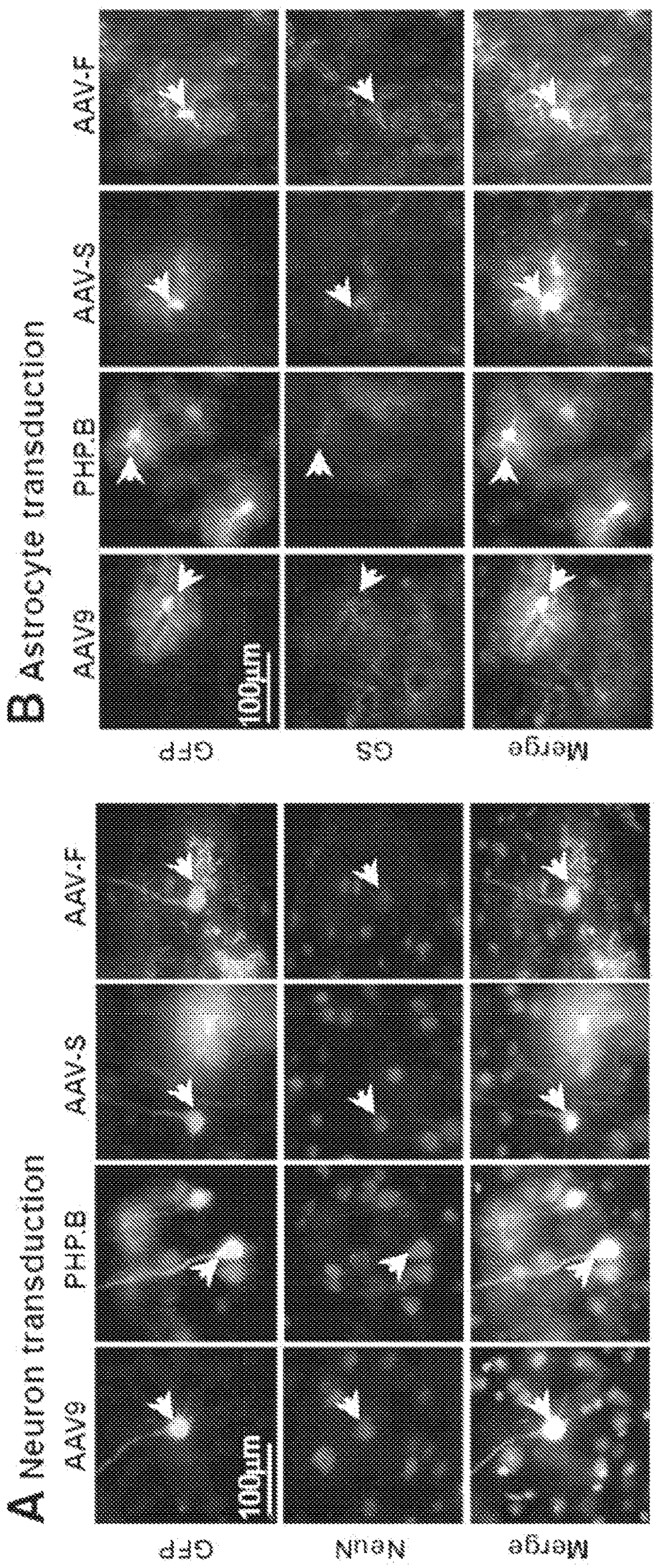
FIGs. 4A-B

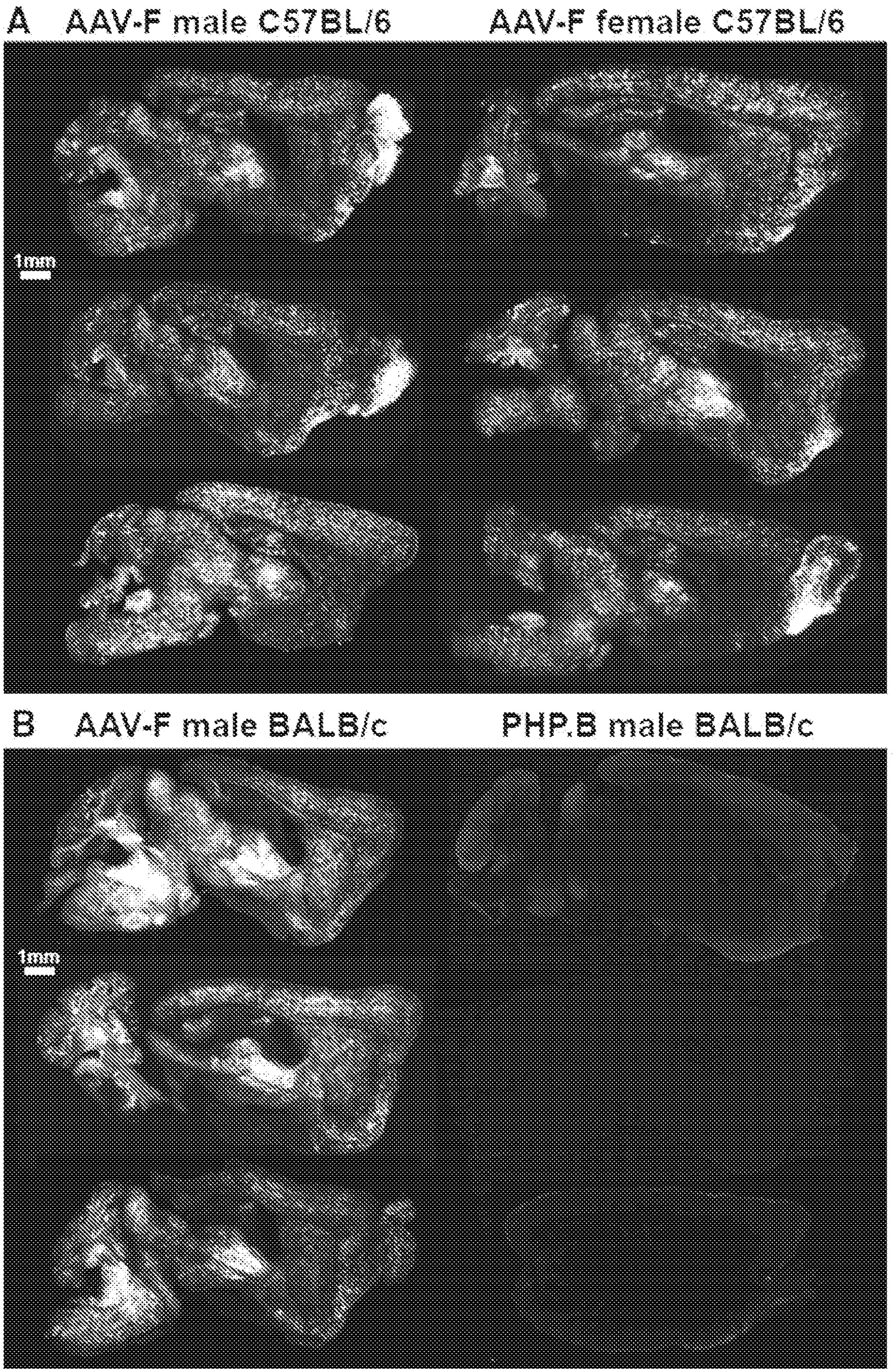
*FIGs. 5A-B*

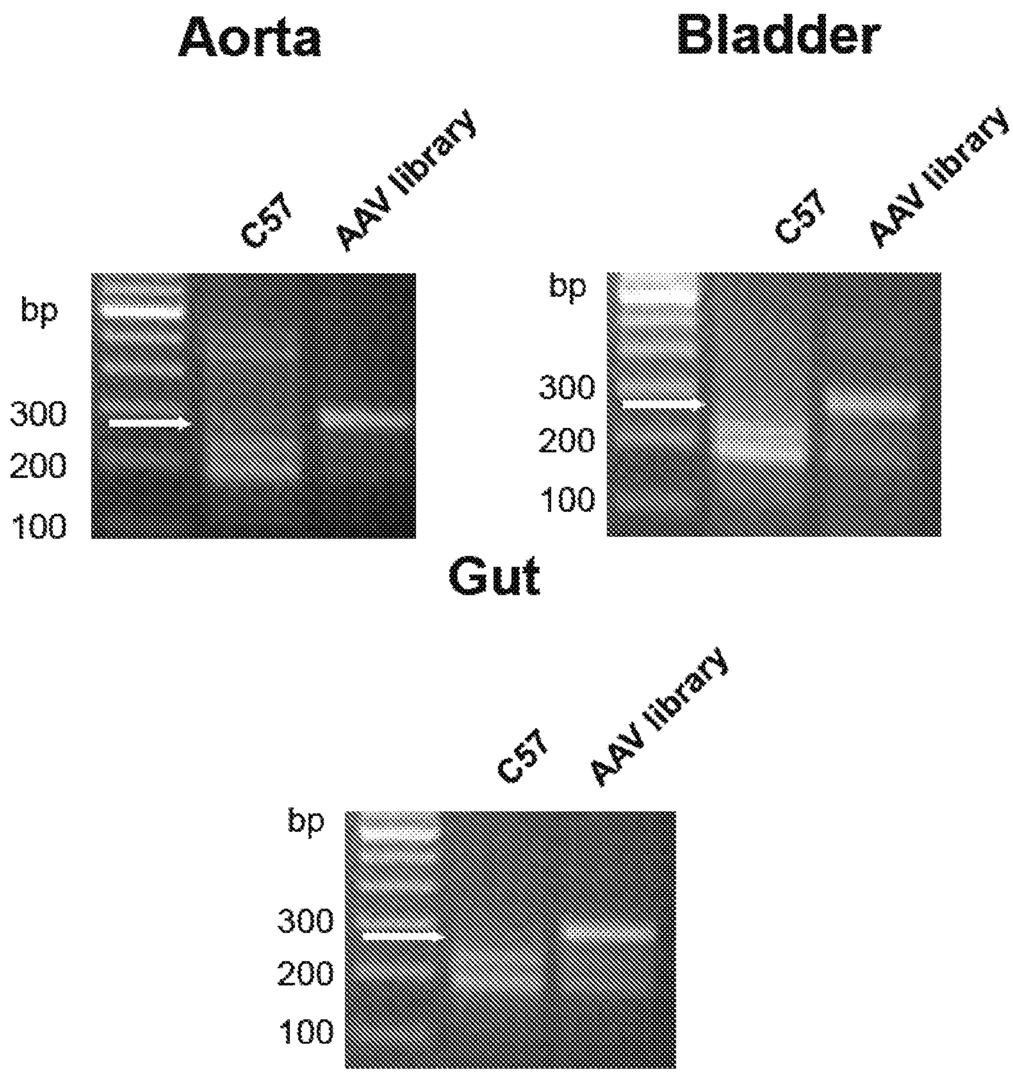
*FIG. 7B, Continued*

| DNA sequence | SEQ ID NO: | Peptide sequence | SEQ ID NO: | Frequency |
|---|---|---|---|---|
| ACGGGGTGTAAGTGTTCGCAG | 87. | TGCKCSQ | 88. | 0.05897 |
| CATCTGCCTGTTATGAATGAG | 89. | HLPVMNE | 90. | 0.055593 |
| GTTTCGTTGAATTATACTGCT | 91. | VSLNYTA | 92. | 0.052346 |
| CCTCCTCCTCCTCCGCCTGTG | 93. | PPPPPPV | 94. | 0.0498 |
| AGTTCTACTGCTAGTCGTCGT | 95. | SSTASRR | 96. | 0.048579 |
| CTGCTTGTGACGTGTCCGGAT | 97. | LLVTCPD | 98. | 0.039487 |
| TCGTTGCTGCGTTATGCTCCG | 99. | SLLRYAP | 100. | 0.039149 |
| CAGCCGCTGCGTCCGAATCTG | 101. | QPLRPNL | 102. | 0.037876 |
| GCTTTGGATACTCATCATTGG | 103. | ALDTHHW | 104. | 0.036811 |
| CGGCCTACTCGTCTTTCTCCG | 105. | RPTRLSP | 106. | 0.036811 |
| GATGCTTGGTCGGCTTCTATT | 107. | DAWSASI | 108. | 0.036213 |
| TATAAGTGTTGGCCGAGGAGT | 109. | YKCWPRS | 110. | 0.03585 |
| AAGTATCTGACTAATCTTTCT | 111. | KYLTNLS | 112. | 0.034941 |
| TCGCGGCCTCCGCCGTCTCTG | 113. | SRPPPSL | 114. | 0.030083 |
| TAGGCGCCGATTCTTTAGTTG | 115. | | | 0.029433 |
| ATGCCTCCTTCTCCTCCGGGT | 116. | MPPSPPG | 117. | 0.029069 |
| CCGTTTCCTCAGATGCTTTTT | 118. | PFPQMLF | 119. | 0.028108 |
| CCTCAGGCGTCTCATGTTAAT | 120. | PQASHVN | 121. | 0.027199 |
| GAGTATTGTTCTTAGATTCCT | 122. | EYCS | 123. | 0.026887 |
| TCGTAGAATTTGCGGGTGTTG | 124. | S | 125. | 0.025588 |
| TATTATCATTCGCTGTCGTCG | 126. | YYHSLSS | 127. | 0.024809 |
| AAGCATTCTCAGCGGCGGAAT | 128. | KHSQRRN | 129. | 0.024004 |
| TAGACTAATGTGTGGATTAAT | 130. | | | 0.023484 |
| ACTAAGACGCCTGAGCATTAG | 131. | TKTPEH | 132. | 0.019977 |
| GGGCCGGAGGGGCCGCGTCTG | 133. | GPEGPRL | 134. | 0.019536 |
| TGTACTTCTAATCTGCATGGG | 135. | CTSNLHG | 136. | 0.018263 |
| GTTATTACTCATCTGACTGAT | 137. | VITHLTD | 138. | 0.018133 |
| GATTCTAATCATTTTGGTCCG | 139. | DSNHFGP | 140. | 0.017899 |
| CCGAGTCAGCAGACTTAGATG | 141. | PSQQT | 142. | 0.014652 |
| TTTGTTGCTGATTGGGAGCCT | 143. | FVADWEP | 144. | 0.014262 |
| CTGATGCAGACTAATATTACG | 145. | LMQTNIT | 146. | 0.011742 |
| CTGGTGGTTCCTAATCGTGAT | 147. | LVVPNRD | 148. | 0.011586 |
| N/A | 149. | Others | 150. | 0.022861 |

*FIG. 7C*

| Total events | tdTomato+ sort count | % of tdTomato+ cells |
|---|---|---|
| 8,850,410 | 3,834 | 0.0433 |

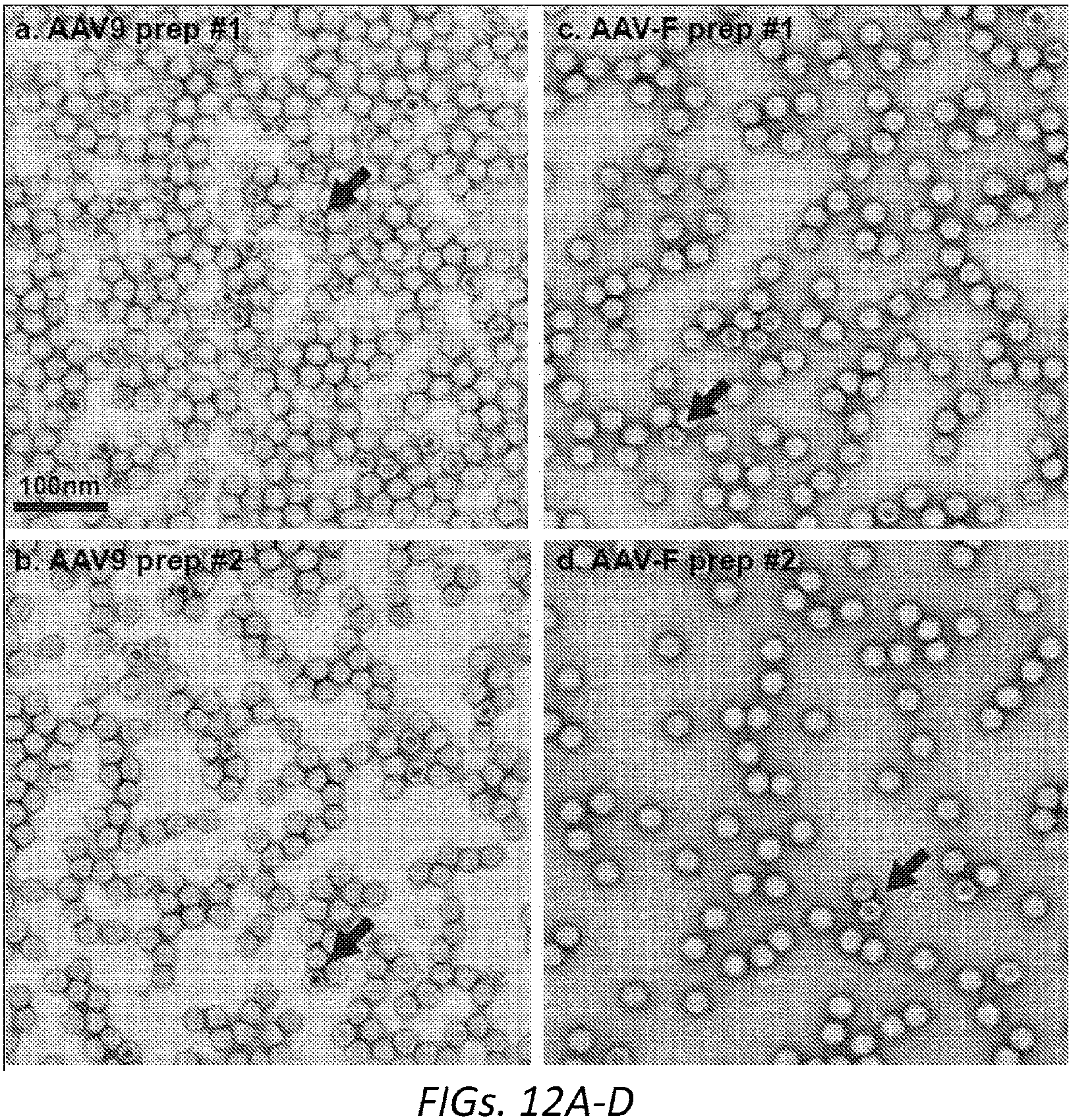
*FIGs. 12A-D*

Brain transduction after intrathecal injection

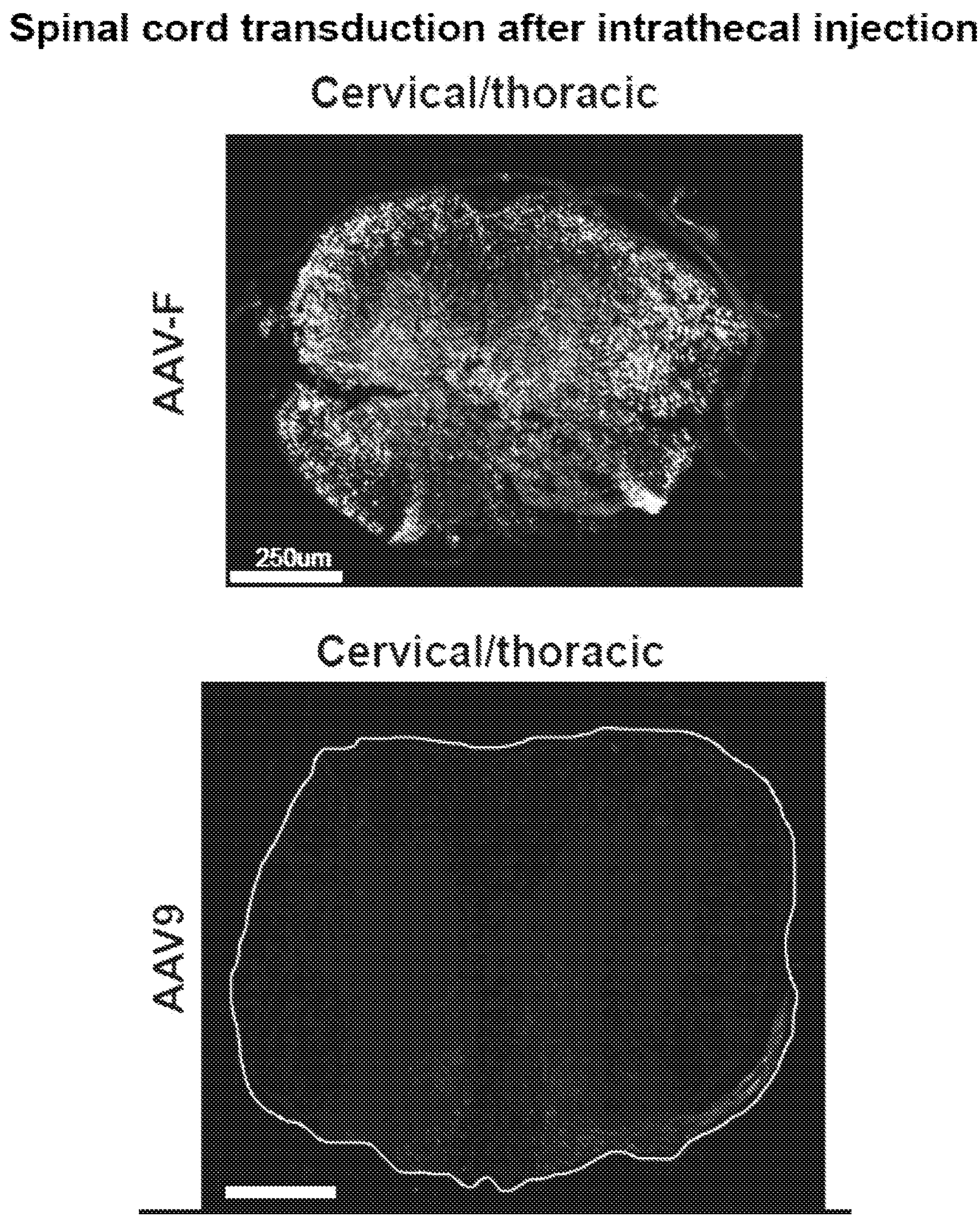
*FIG. 14A, continued*

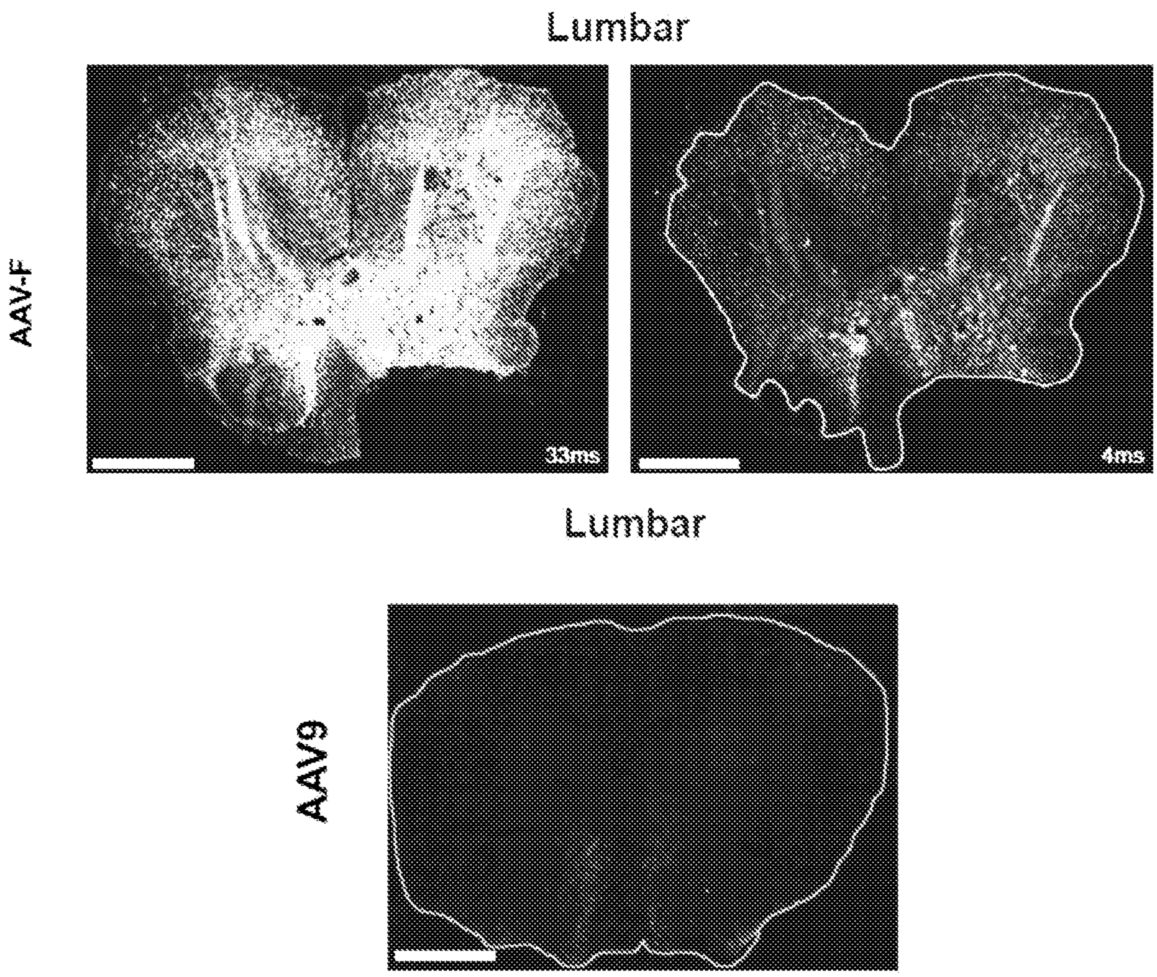
*FIG. 14A, continued*

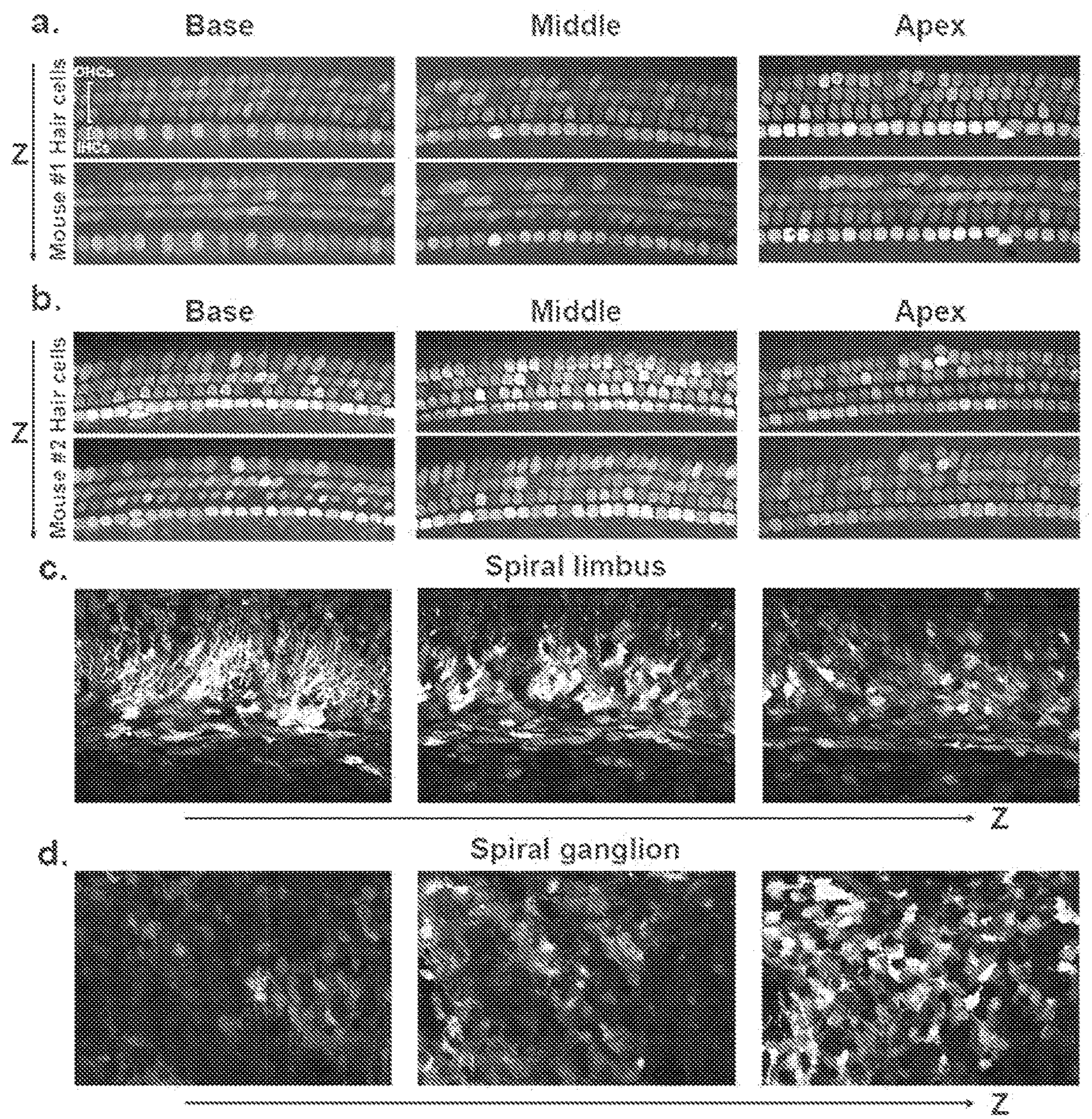
FIGs. 15A-D iii. Dissociate cochlea
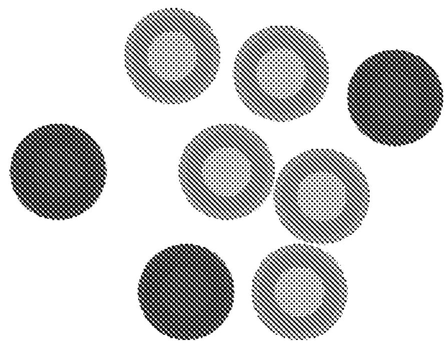
iv. Flow sort tdTomato+ fibrocytes
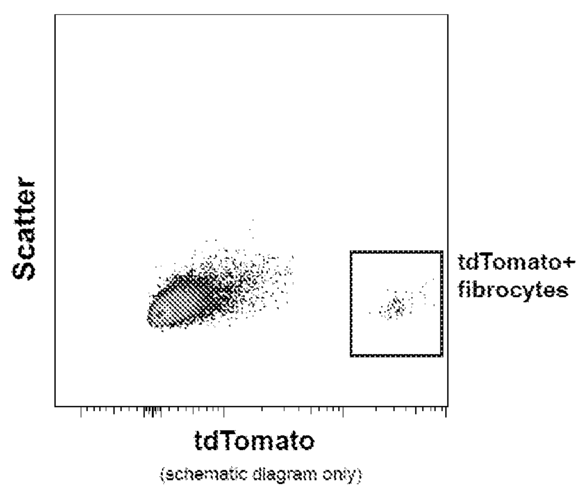
v. NGS candidate peptides
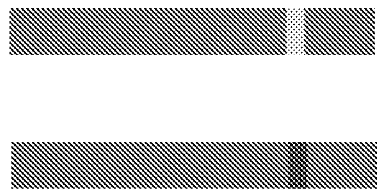
*FIG. 16A, continued*

ENGINEERED ADENO-ASSOCIATED (AAV) VECTORS FOR TRANSGENE EXPRESSION

CLAIM OF PRIORITY

This application is a national stage application under 35 USC § 371 of International Application No. PCT/US2020/025720, filed on Mar. 30, 2020, which claims the benefit of U.S. Provisional Application Ser. No. 62/825,703, filed on Mar. 28, 2019. The entire contents of the foregoing are incorporated herein by reference.

FEDERALLY SPONSORED RESEARCH OR DEVELOPMENT

This invention was made with Government support under Grant Nos. AG047336 and DC017117 awarded by the National Institutes of Health. The Government has certain rights in the invention.

SEQUENCE LISTING

This application contains a Sequence Listing that has been submitted electronically as an ASCII text file name 29539_0390US1_Sequence_Listing. The ASCII text file, created on Sep. 23, 2021, is 57.2 kilobytes in size. The material in the ASCII text file is hereby incorporated by reference in its entirety.

TECHNICAL FIELD

Described herein are engineered AAV vectors for transgene expression, e.g., in the CNS, PNS, inner ear, heart, or retina, and methods of use thereof. Also provided are methods for discovering new engineered AAV vectors that mediate transgene expression in desired cell types.

BACKGROUND

While AAV9 vectors have shown remarkable potential for delivery to the CNS after systemic delivery, resulting in clinical success in pediatric patients with spinal muscular atrophy[1], systemic injection of high doses of AAV vectors can lead to induction of a T-cell response that can eliminate transduced cells[2]. In monkeys, there is one report in which high systemic doses of an AAV9-like vector resulted in toxicity and death of the animal which was attributed to systemic inflammation[3]. A recent phase I clinical trial using high dose AAV9 to treat muscular dystrophy was placed on hold by the FDA due to an immune reaction after vector infusion in one patient. The reason high doses are required is due to the relatively low efficiency of AAV on a per-vector genome copy basis to provide adequate transgene expression in a substantial number of target cells. Thus, developing new AAV capsids which allow more efficient transduction at lower doses should result in better therapeutic efficacy while lowering safety issues, such as immunotoxicity.

SUMMARY

Described herein are methods that use an adeno-associated virus (AAV) vector genome with a two-part expression cassette to identify novel virus clones. The first is a Cre-recombinase cassette under a promoter of interest. The second part is an AAV promoter to drive expression of an engineered capsid gene, cloned "in cis" to the first section of the viral genome. Virus vectors are selected for transgene expression (highly sensitive Cre expression) using cells that express a reporter gene (e.g., green fluorescent protein) with an upstream loxP/stop site, thus preventing reporter expression until AAV vector-delivered Cre removes the stop site. Reporter gene positive cells can be isolated and recovered AAV capsid sequences will have a higher likelihood of mediating efficient transgene expression. Also described herein are engineered viral sequences that drive efficient expression in the central nervous system (CNS) and peripheral nervous system (PNS), heart, liver, and inner ear.

Thus, provided herein are AAV capsid proteins comprising an amino acid sequence that comprises at least four contiguous amino acids from the sequence STTLYSP (SEQ ID NO: 1) or FVVGQSY (SEQ ID NO:2). In some embodiments, the AAV capsid proteins comprise an amino acid sequence that comprises at least five contiguous amino acids from the sequence STTLYSP (SEQ ID NO:1) or FVVGQSY (SEQ ID NO:2). In some embodiments, the AAV capsid proteins comprise an amino acid sequence that comprises at least six contiguous amino acids from the sequence STTLYSP (SEQ ID NO: 1) or FVVGQSY (SEQ ID NO:2). Alternatively, the AAV capsid proteins comprise an amino acid sequence that comprises at least four, five, or six contiguous amino acids from the sequences shown in FIG. 2A or 7C (SEQ ID NOs:17-150).

In some embodiments, the AAV is AAV9.

In some embodiments, the AAV capsid proteins comprises AAV9 VP1.

In some embodiments, the sequence is inserted into the capsid at a position corresponding to amino acids 588 and 589 of SEQ ID NO:6, at the VP1/VP2 interface (amino acid 138) or any site between 583-590.

Also provided herein are nucleic acids encoding an AAV capsid protein as described herein.

Additionally, provided herein are AAVs comprising the capsid proteins described herein, and preferably not comprising a wild type VP1, VP2, or VP3 capsid protein. In some embodiments, the AAVs further comprising a transgene, preferably a therapeutic transgene.

Further provided are methods of delivering a transgene to a cell, e.g., a cell in vivo or ex vivo/in vitro. The methods include contacting the cell with an AAV as described herein. In some embodiments, the cell is a neuron (optionally a dorsal root ganglion neuron or spiral ganglion neuron), astrocyte, cardiomyocyte, or myocyte, astrocyte, glial cell, inner hair cell, outer hair cell, supporting cell, fibrocyte of the inner ear, photoreceptors, interneurons, retinal ganglion, or retinal pigment epithelium.

In some embodiments, the cell is in a living subject, e.g., a mammalian subject, preferably a human. In some embodiments, the cell is in a tissue selected from the brain, spinal cord, dorsal root ganglion, heart, inner ear, eye, or muscle, and a combination thereof. In some embodiments, the subject has Alzheimer's Disease; Parkinson's Disease; X-linked Adrenoleukodystrophy; Canavan's; Niemann Pick; Spinal muscular atrophy; Huntington's Disease; Connexin-26; Usher Type 3A; Usher Type 2D; Hair cell-related hearing loss; Hair cell-related hearing loss (DFNB7/11); Inner hair cell-related hearing loss (DFNB9); Usher Type 1F; Usher Type 1B; Retinitis pigmentosa (RP; non-syndromic); Leber congenital amaurosis; Leber Hereditary Optic Neuropathy; Usher Syndrome (RP; syndromic with deafness); Duchenne Muscular Dystrophy; Allograft vasculopathy; or Hemophilia A and B. The methods and compositions described herein can be used to treat these conditions, by administration of a therapeutically effective amount of an AAV carrying a therapeutic transgene, sufficient to ameliorate, reduce risk of, or delay onset of one or more symptoms of the condition.

In some embodiments, the cell is in the brain of the subject, and the AAV is administered by parenteral delivery; intracerebral; or intrathecal delivery.

In some embodiments, the intrathecal delivery is via lumbar injection, cisternal *magna* injection, or intraparenchymal injection.

In some embodiments, the AAV is delivered by parenteral delivery, preferably via intravenous, intraarterial, subcutaneous, intraperitoneal, or intramuscular delivery.

In some embodiments, the cell is in the eye of the subject, and the AAV is administered by subretinal or intravireal injection.

In some embodiments, the cell is in the inner ear of the subject, and the AAV is administered to the cochlea through application over or through the round window membrane, through a surgically drilled cochleostomy adjacent to the round window, a fenestra in the bony oval window, or a semicircular canal.

Also provided herein are library construct AAVs comprising:

(i) a sequence encoding a Cre recombinase driven by a promoter;

(ii) a sequence encoding an AAV9 capsid protein with a peptide as described herein, e.g., a heptamer peptide, inserted between the sequences encoding amino acids (aa) 588-589 of the capsid, driven by a promoter, downstream of the Cre cassette. In some embodiments, the peptide comprises a random peptide sequence or a pre-selected peptide sequence.

Further provided are libraries comprising a plurality of the library constructs as described herein. In some embodiments, wherein the peptide sequences are random, the library comprises library constructs having sequences encoding all possible variants of the heptamer.

Additionally provided herein are methods for identifying an engineered capsid that mediates transgene expression in a pre-selected cell type. The methods include: (a) administering the library, as described herein, to a non-human model animal, preferably a mammal, wherein the cells of the model animal express a loxP-flanked STOP cassette upstream of a reporter sequence; (b) isolating cells of the pre-selected cell type; (c) selecting cells in which the reporter sequence is expressed; (d) isolating at least part of the library construct, preferably a part comprising the heptamer, from the selected cells in which the reporter sequence is expressed from step (c); and (e) determining identity of the heptamers in the library constructs isolated in step (d), wherein the heptamers that are isolated can mediate transgene expression in the pre-selected cell type.

In some embodiments, the reporter sequence encodes a fluorescent reporter protein.

In some embodiments, the model animal is transgenic for the loxP-flanked STOP cassette upstream of a reporter sequence, or wherein the loxP-flanked STOP cassette upstream of a reporter sequence can be expressed from a second construct.

In some embodiments, determining identity of the heptamers in the library constructs comprises using DNA sequencing analysis.

In some embodiments, the methods also include before and/or after step (e): using PCR to amplify sequences comprising the heptamer sequences, optionally comprising full capsid sequences, from the library constructs isolated in step (d); cloning the amplified sequences back to a second set of library vectors; repackaging the second set of library vectors; and performing steps (a)-(d) or (a)-(e) on the second set of library vectors.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and Figures, and from the claims.

DESCRIPTION OF DRAWINGS

FIGS. 2A-B. Identification of AAV-S and AAV-F after two rounds of in vivo selection for brain transduction after systemic injection. Donut charts indicate the frequency of particular peptide inserts determined by next-generation sequencing. a. Table of Round 2 vector sequences after production but before injection (SEQ ID NOS:17-86). b. Donut chart of peptide frequency appearing in iTransduce isolation after Round 2 injection (SEQ ID NOs. 1-3). "Others" indicates sequence variants appearing as less than 1% of the total pool (in (a), variants isolated after Round 2 screen are also highlighted, appearing at less than 1%). * indicates a stop codon.

FIGS. 3A-F. AAV-F efficiently transduces the brain of mice after systemic injection. a. Single-stranded AAV-GFP expression cassette used to compare capsids' transduction potential. ITR, inverted terminal repeats; CBA, hybrid CMV enhancer/chicken beta actin promoter; WPRE, woodchuck hepatitis virus post transcriptional regulatory element; pA, poly A signals (both SV40 and bovine growth hormone derived). b. Representative low magnification images of whole brain sagittal sections from C57BL/6 mice (males) transduced with $1\times10^{11}$ vg (low dose) of AAV9, AAV9-PHP.B, AAV-S, or AAV-F. c. Representative images of sagittal section of brains after injection of $8\times10^{11}$ vg (high dose) of each vector in C57BL/6 males. d. Example sections of spinal cords transduced by each of the four vectors administered intravenously at the higher dose ($8\times10^{11}$ vg/mouse). e. Quantitation of native GFP expression from each vector by the percentage of sections covered by fluorescence at low (left panel) and high (right panel) doses. f. Multiregional comparison of transduction in the brain at the higher dose. *, $p<0.001$; **, $p<0.0001$ after one-way ANOVA with Tukey's multiple comparison test (n=3 each group).

FIGS. 4A-E. AAV vector comparison of neuron and astrocyte transduction and biodistribution. High magnification images of AAV9, AAV-PHP.B, AAV-S and AAV-F transduced cells (GFP positive) after co-immunostaining with markers for a. neurons (NeuN) and b. astrocytes (glutamine synthetase, GS), Merged cells also include nuclear staining by DAPI. c. Stereological evaluation of the percentage of transduced cortical astrocytes and neurons after i.v. delivery of $1\times10^{11}$ vg of each vector. $P<0.0001$ one-way ANOVA. (*) and () represent the significant differences between each vector group after Tukey's multiple comparisons test (n=3 mice/group). d. Biodistribution of vectors in the brain and liver as measured by qPCR of vector genomes, normalized by GAPDH genomic DNA levels (input DNA). e. Transduction of AAV9, AAV9-PHP.B, AAV-S, and AAV-F in peripheral organs following intravenous administration at $8\times10^{11}$ vg in C57BL/6 males. Retinal images: RPE, retinal pigment epithelium; ONL; outer nuclear layer; OPL, outer plexiform layer; INL, inner nuclear layer; IPL, inner plexiform layer; GCL, ganglion cell layer. **$p<0.0001$ (n=3 mice/group, one-way ANOVA with Tukey's multiple comparisons test).

FIGS. 5A-C. AAV-F mediates high transduction efficiency in male and female C57BL/6 mice and also in BALB/c mice. a. Representative images of GFP signal across sagittal brain sections in male and female mice (n=3) transduced by AAV-F at $1\times10^{11}$ vg/mouse. b. Sagittal brain sections of male BALB/c mice injected with AAV-F (left) or AAV9-PHP.B (right) at $1\times10^{11}$ vg/mouse. DAPI was provided as a counterstain along-side GFP to visualize PHP.B-treated brain sections. c. Quantitation of endogenous GFP expression from each vector by the percentage of sections covered by fluorescence. **, $p<0.01$. Unpaired t-test (n=3 mice/group).

FIGS. 7A-C. iTransduce library functionally elicits Cre recombination and PCR amplification of 7-mer peptide-encoding inserts in cap gene can be rescued from tissue. a. Examples of tdTomato DAB staining in tissues after transduction with the unselected iTransduce library in an Ai9 floxed/STOP tdTomato transgenic mouse (right panels). PBS was as injected as control (left panels). Red arrows indicate examples of transduced cells. b. Examples of PCRs rescuing the insert-containing region of the Cap gene from various tissues, including brain, compared to wild-type and transgenic untransduced mice. c. Table illustrating the spectrum of variants seen after the first round of selection, with the most frequent variants highlighted (SEQ ID NOs:87-

150). "Others" indicates grouped sequence variants, each of which appears as less than 1% of the total pool. * indicates a stop codon.

Figure 8A:
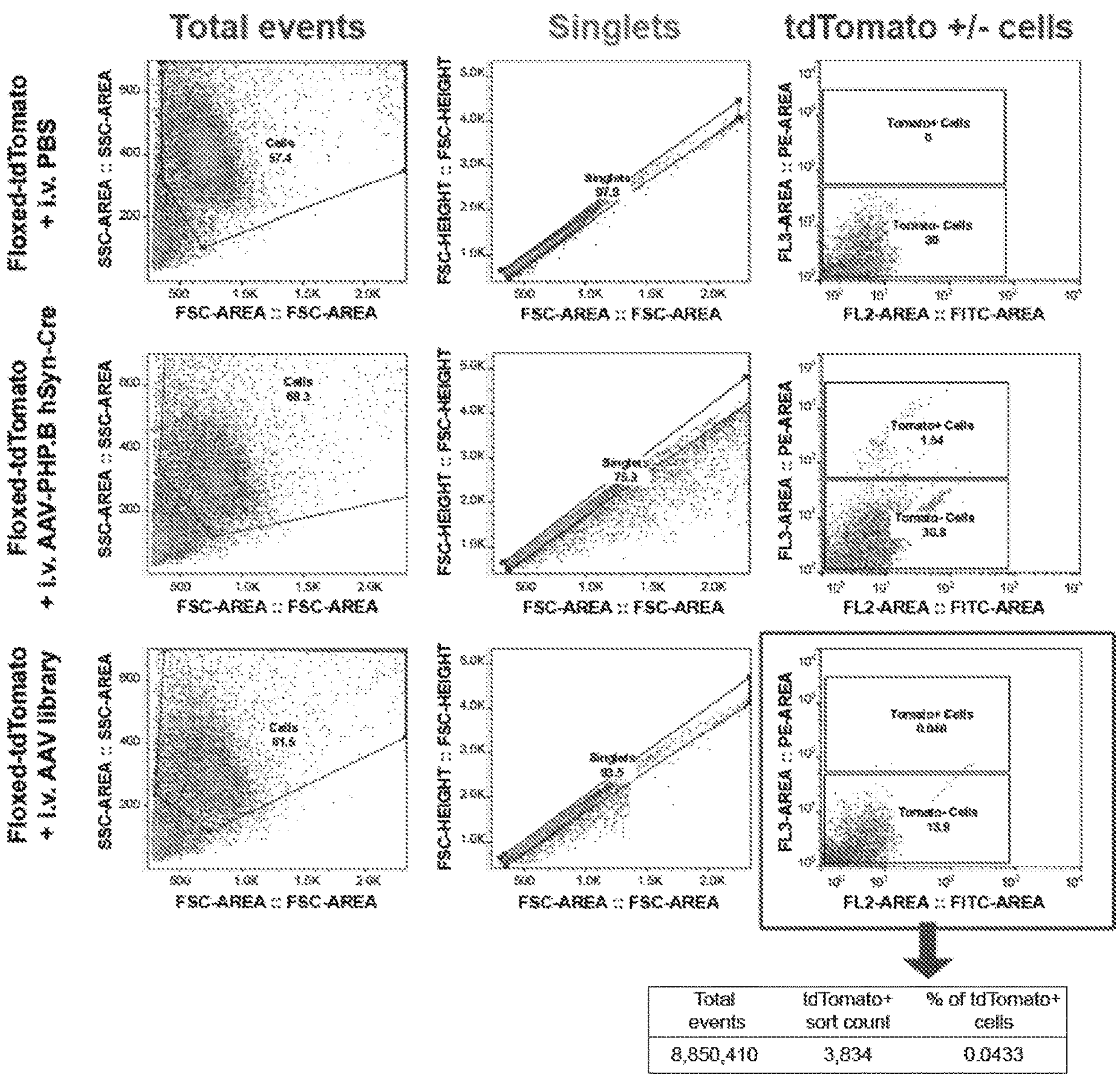
Figure 8B:
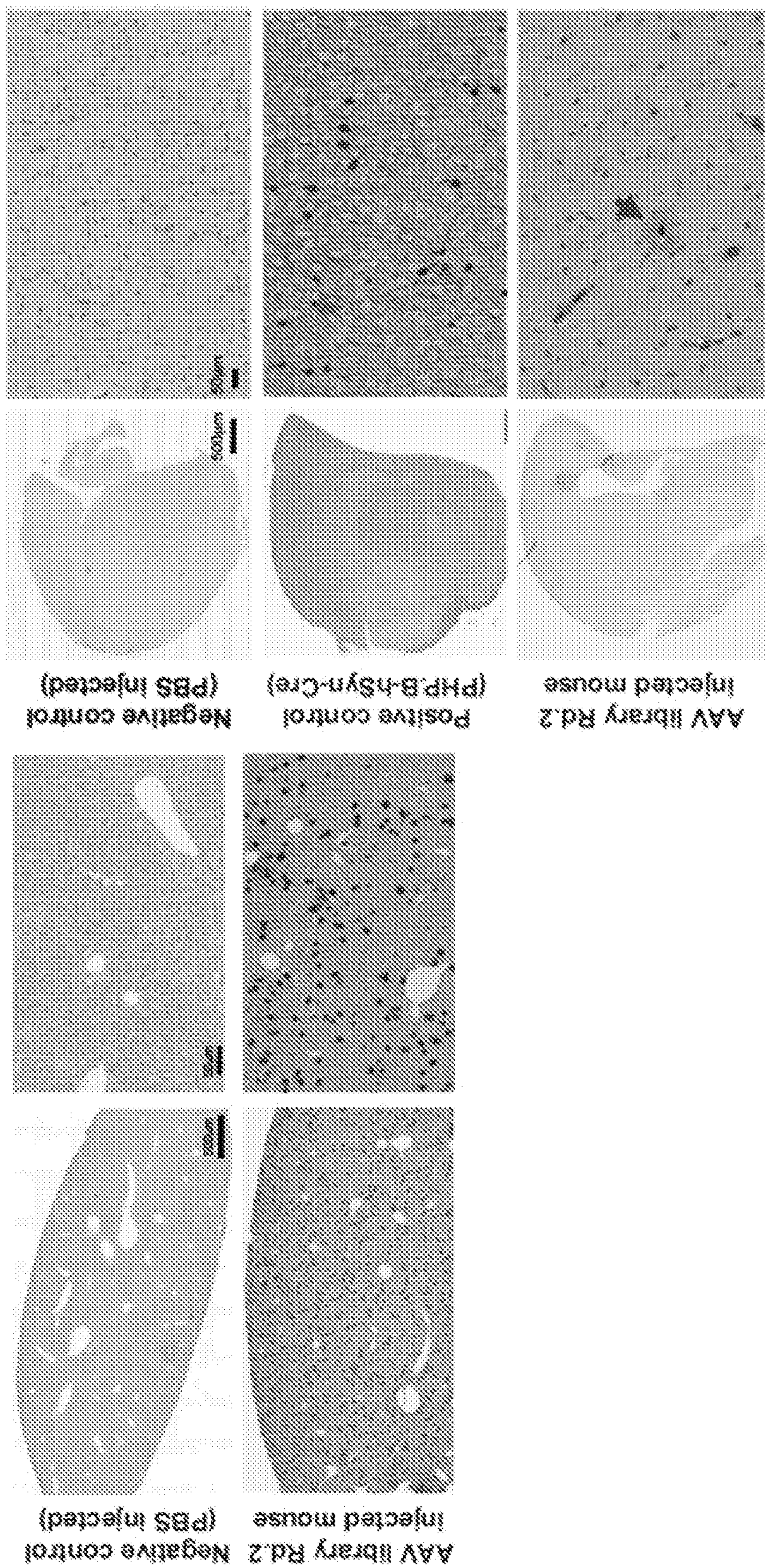

FIGS. 8A-B. Cre-based selection in Round 2 reveals transduction-competent AAVs. a. Flow cytometry analysis of tdTomato-positive cells. Following dissociation of mouse brains, the cell suspension was analyzed and sorted for tdTomato positive cells, with gating drawn based on forward and side scatter (FSC, SSC) to exclude non-viable cells (Total events), to capture only single cells (Singlets), and finally for tdTomato expression (tdTomato+/−cells). To sort tdTomato-positive cells from the AAV library-transduced brains, gating was established based upon a negative control (PBS-injected Ai9) and a positive control (Ai9 mice transduced with AAV9-PHP.B carrying a hSyn-Cre neuron-specific cassette). b. Cre-dependent recombination events are detected after DAB immunostaining for tdTomato in the liver and brain after injection of the Round 2 library (compared to PBS or AAV9-PHP.B hSyn-Cre injections). Arrow indicates a positive cell (astrocyte) in the brain of the AAV library injected mouse.

Figure 9A:
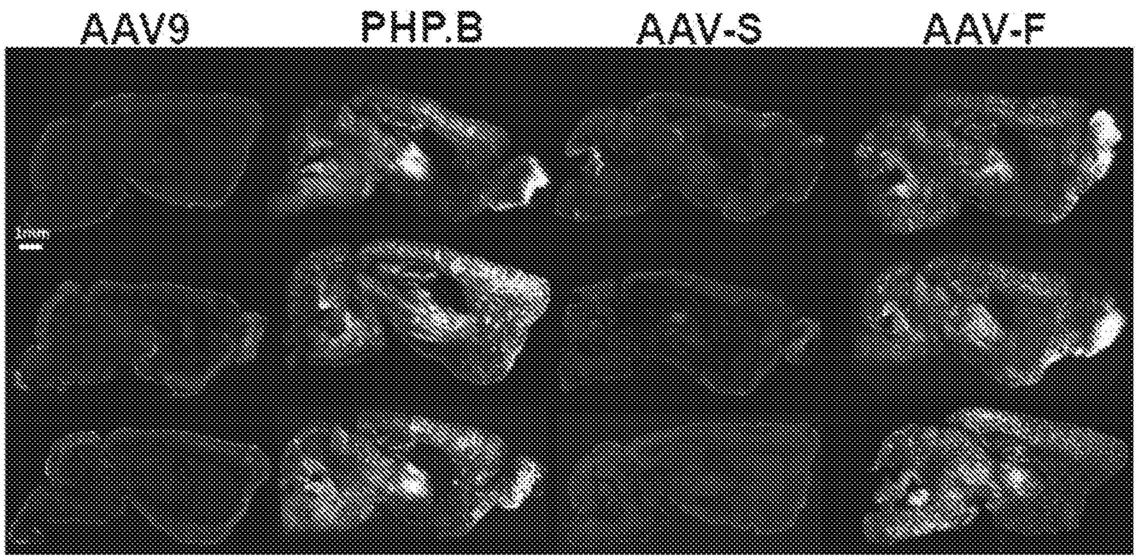
Figure 9B:
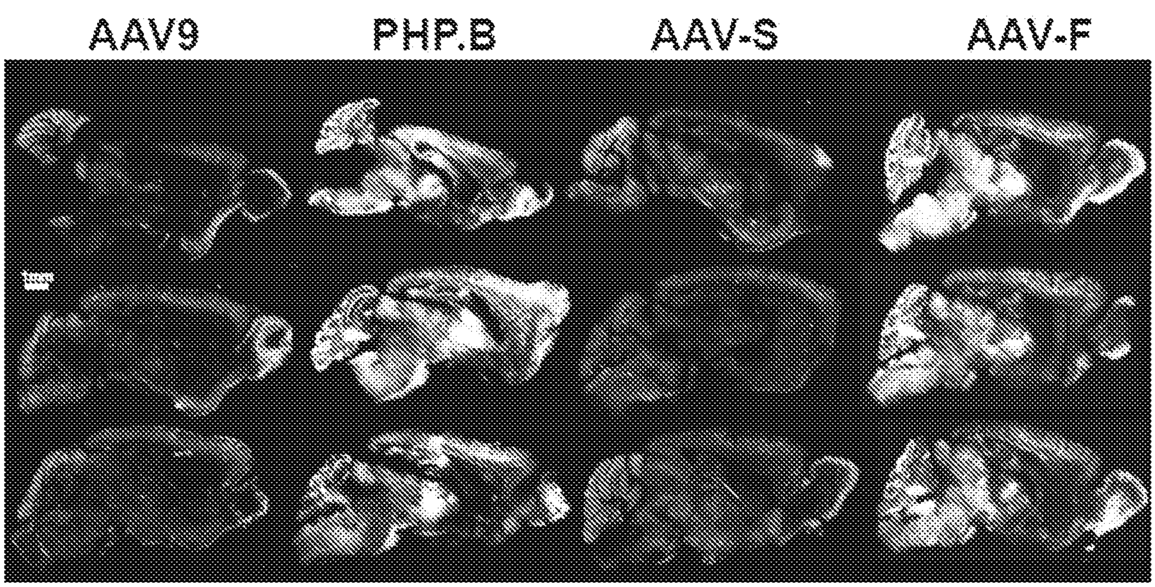

FIGS. 9A-B. Transduction of the brain by AAV-F and AAV-S after intravenous delivery of a low ($1\times10^{11}$ vg) or high doses of vector ($8\times10^{11}$ vg). Transduction profile in the brain after transduction by AAV9, AAV9-PHP.B, AAV-S and AAV-F in n=3 mice, demonstrating endogenous (unstained) GFP fluorescence in sagittal sections. Mice were administered with either $1\times10^{11}$ vg (a) or $8\times10^{11}$ vg (b). Each section in each group is taken from an individual mouse.

Figure 10A:
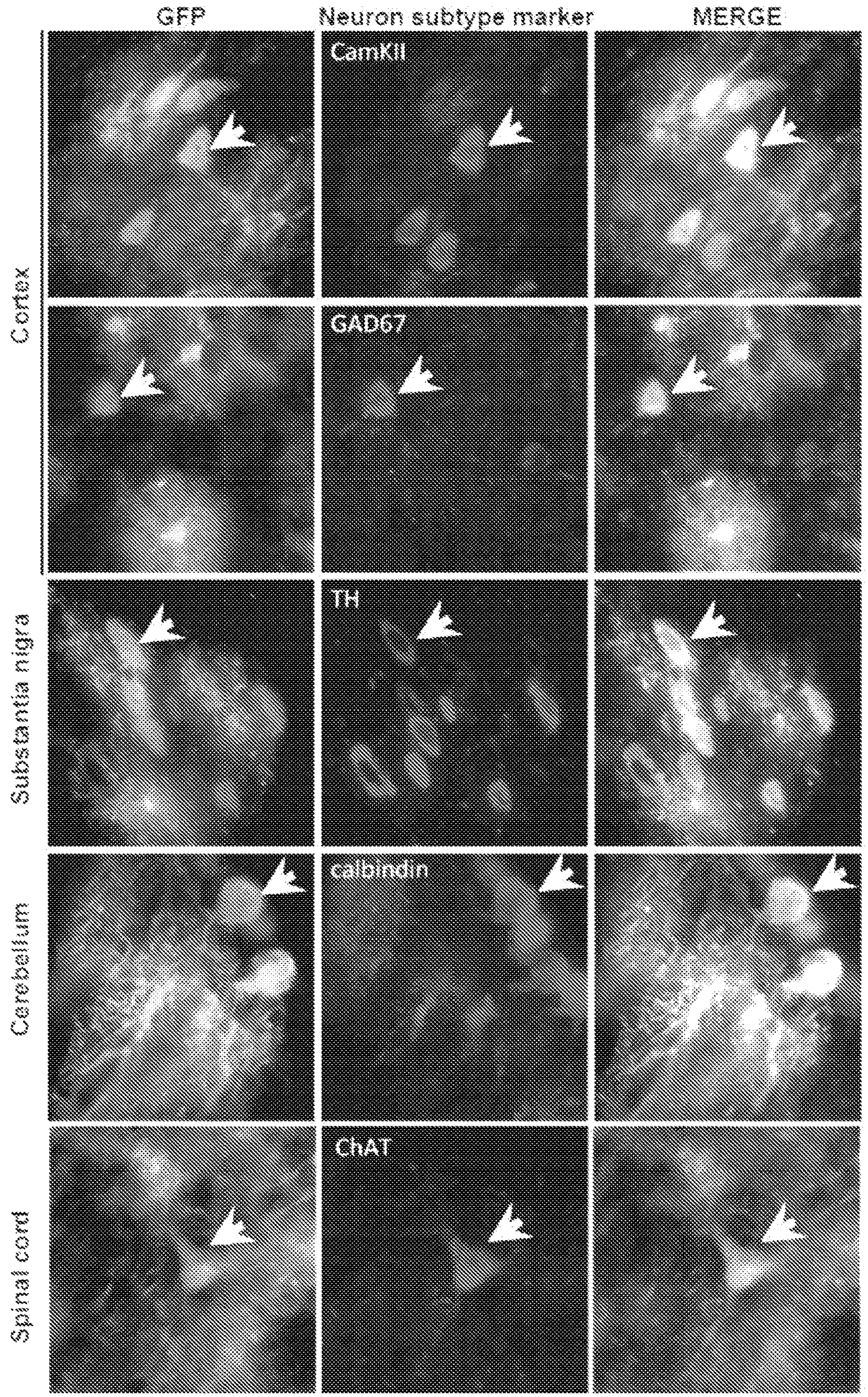
Figure 10B:
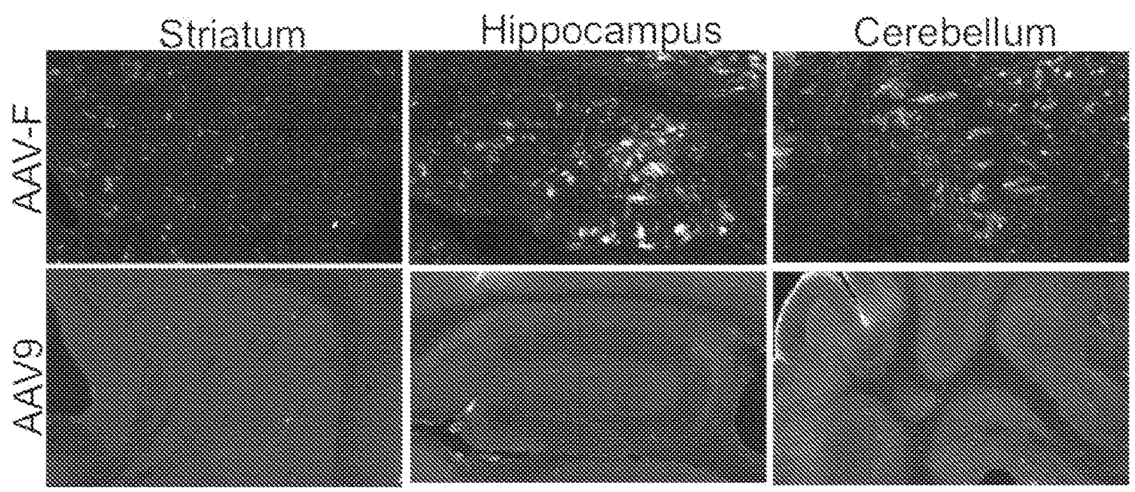

FIGS. 10A-B. (a) AAV-F transduces multiple subtypes of neurons in the mouse brain. GFP expression driven by AAV-F was detected in a broad range of neuronal subtypes across different regions of the brain and CNS. CamKII, excitatory neurons. GAD67, inhibitory neurons. Tyrosine hydroxolase (TH), Purkinje neurons. Choline acetyltransferase (ChAT), motor neurons (white arrows represent examples of transduced neurons for each subtype). (b) AAV-F mediates efficient transduction while AAV9 does not at $1\times10^{11}$ vg/mouse. Representative 10× images from mice from FIG. 3*b* show GFP expression in striatum, hippocampus, and cerebellum from mice injected with AAV-F and AAV9.

Figure 11:
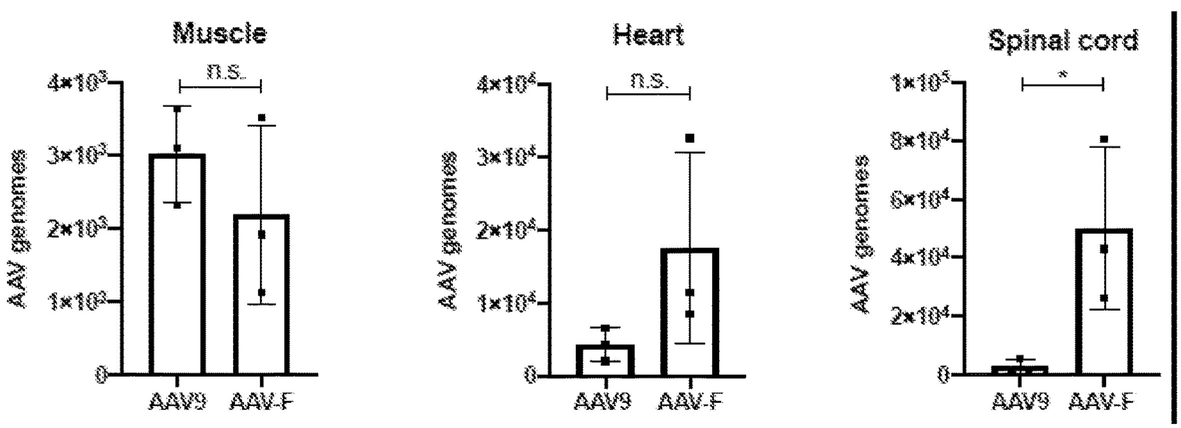
Figure 12E:
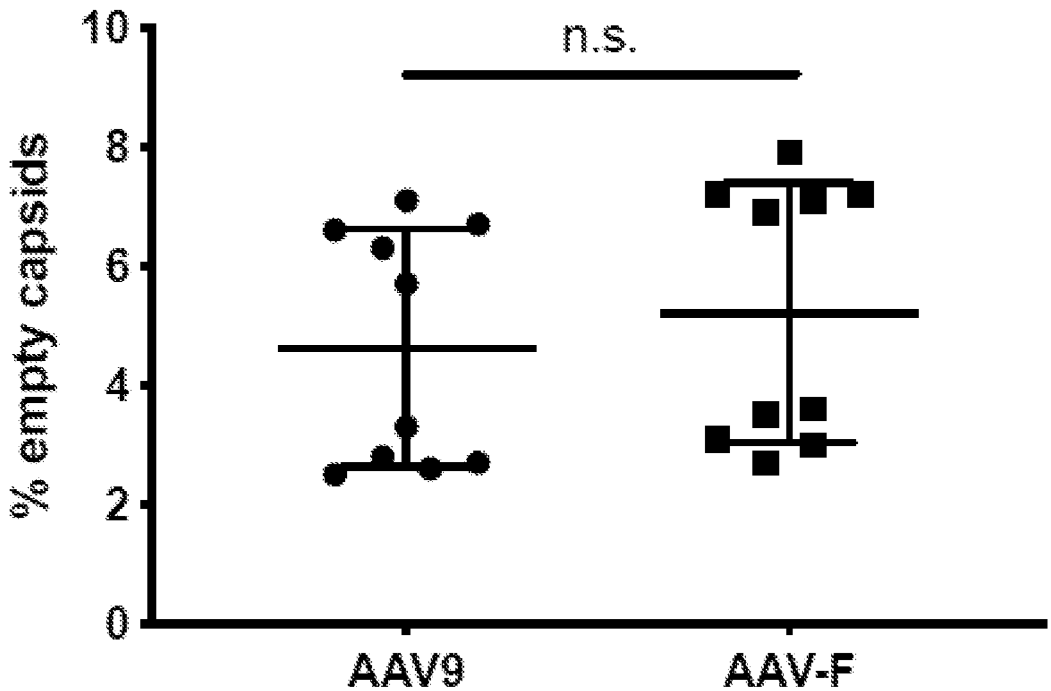

FIG. 11. Biodistribution of AAV-F after systemic delivery. AAV-F biodistribution as compared to AAV9 is shown in skeletal muscle, heart, and spinal cord tissue. Biodistribution was measured by qPCR of vector genomes, and samples were normalized against GAPDH genomic DNA for equal input. n.s, not significant. *, $p<0.05$ (n=3 mice/group, each mouse sample run in triplicate, two-tailed t-test).

FIGS. 12A-E. Quantification of empty capsids by transmission electron microscopy (TEM). a-d. Representative image segments of electron micrographs of AAV9 and AAV-F preps. Two preps each of AAV9 (a,b) and AAV-F (c,d) were quantified, by counting full vs. empty capsids across five images for each prep (examples of empty capsids are indicated by arrows). e. Quantification of empty capsid percentages for AAV9 and AAV-F preps. n.s: not significant ($p=0.54$, unpaired t-test).

Figure 13:
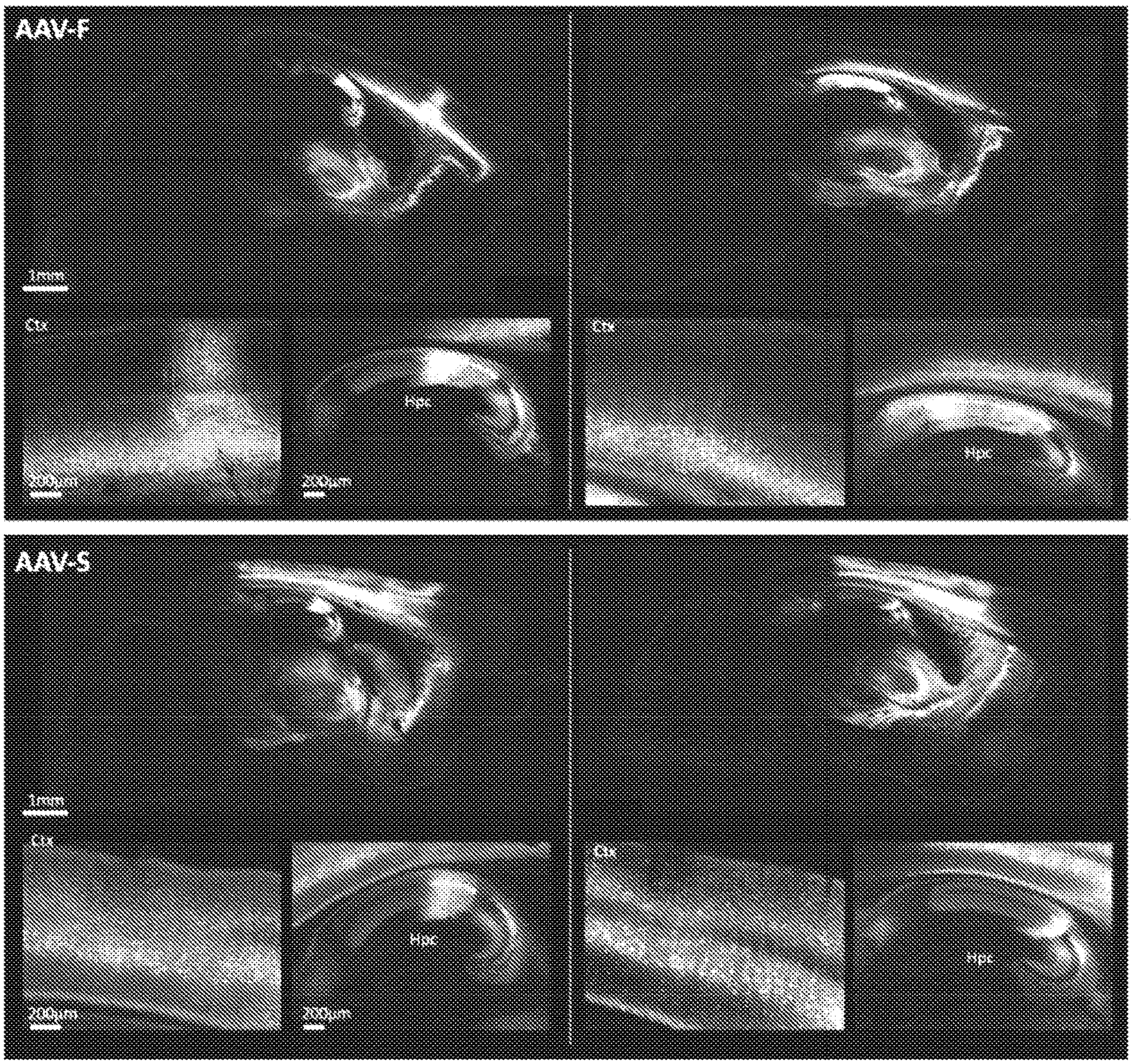
Figure 14A:
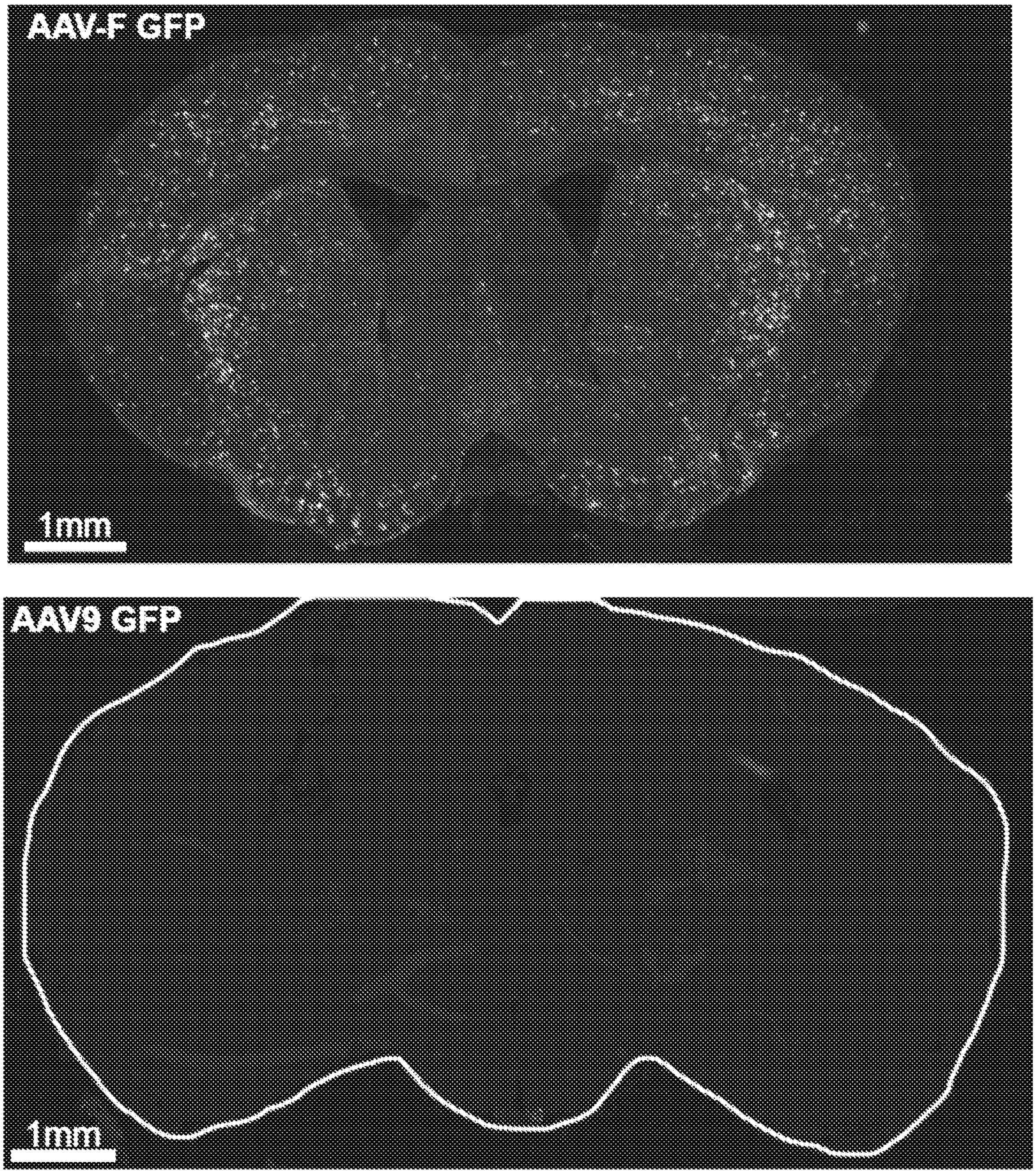
Figure 14B:
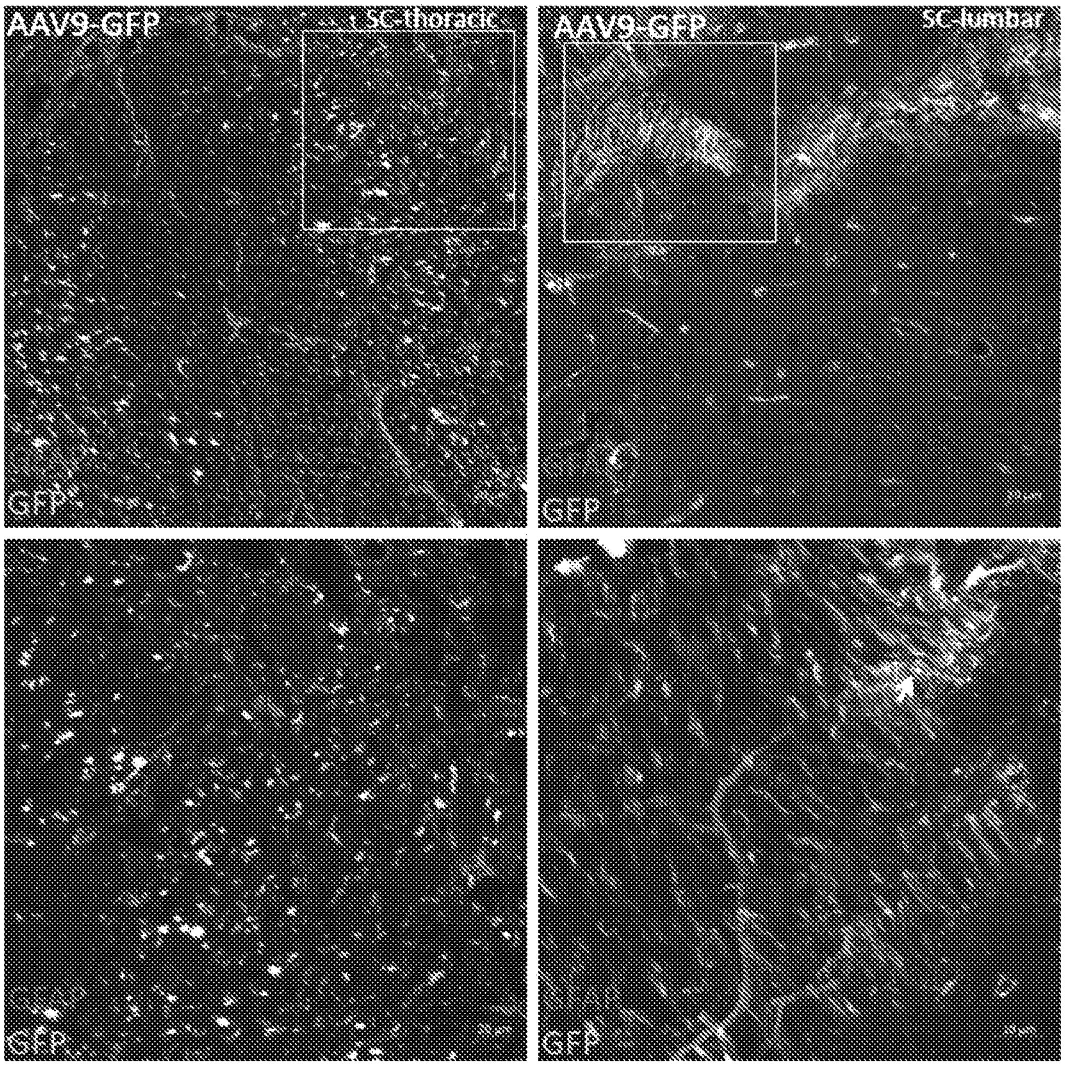
Figure 14C:
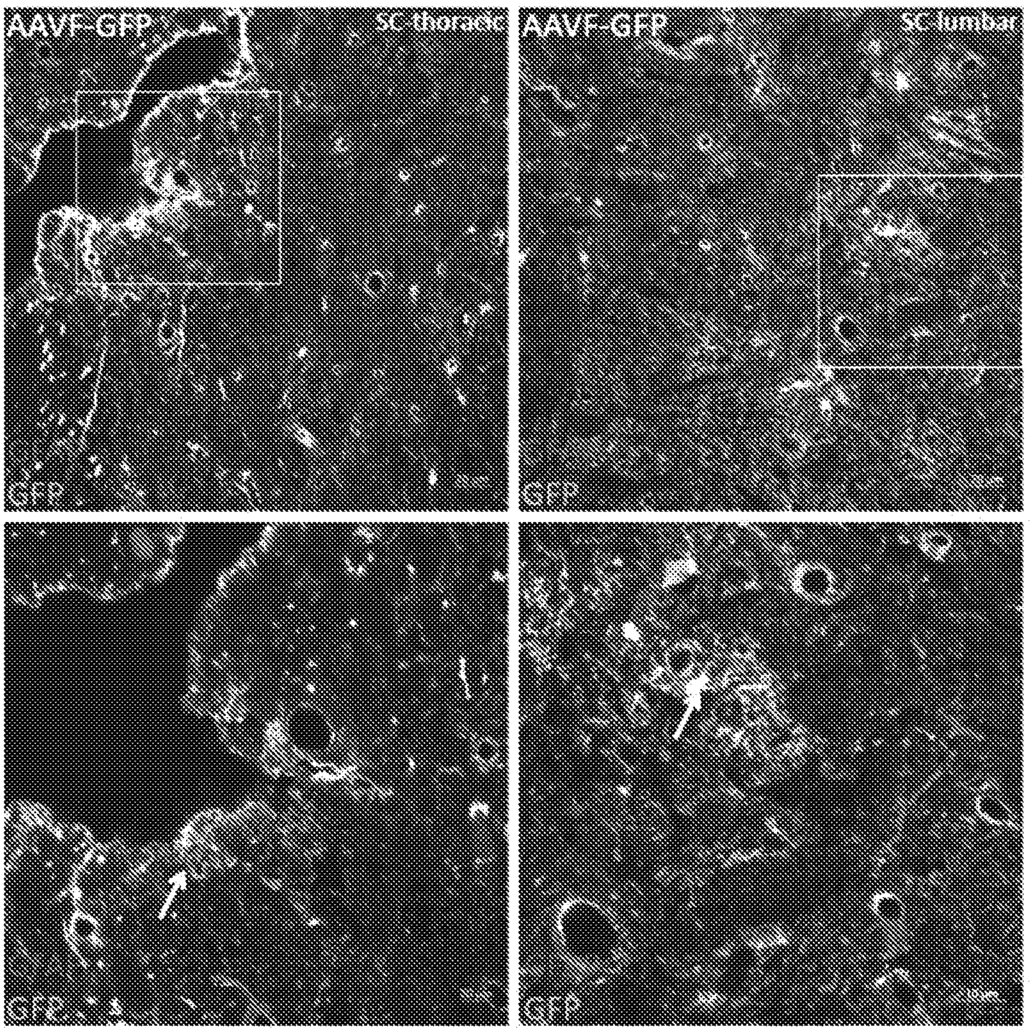
Figure 14D:
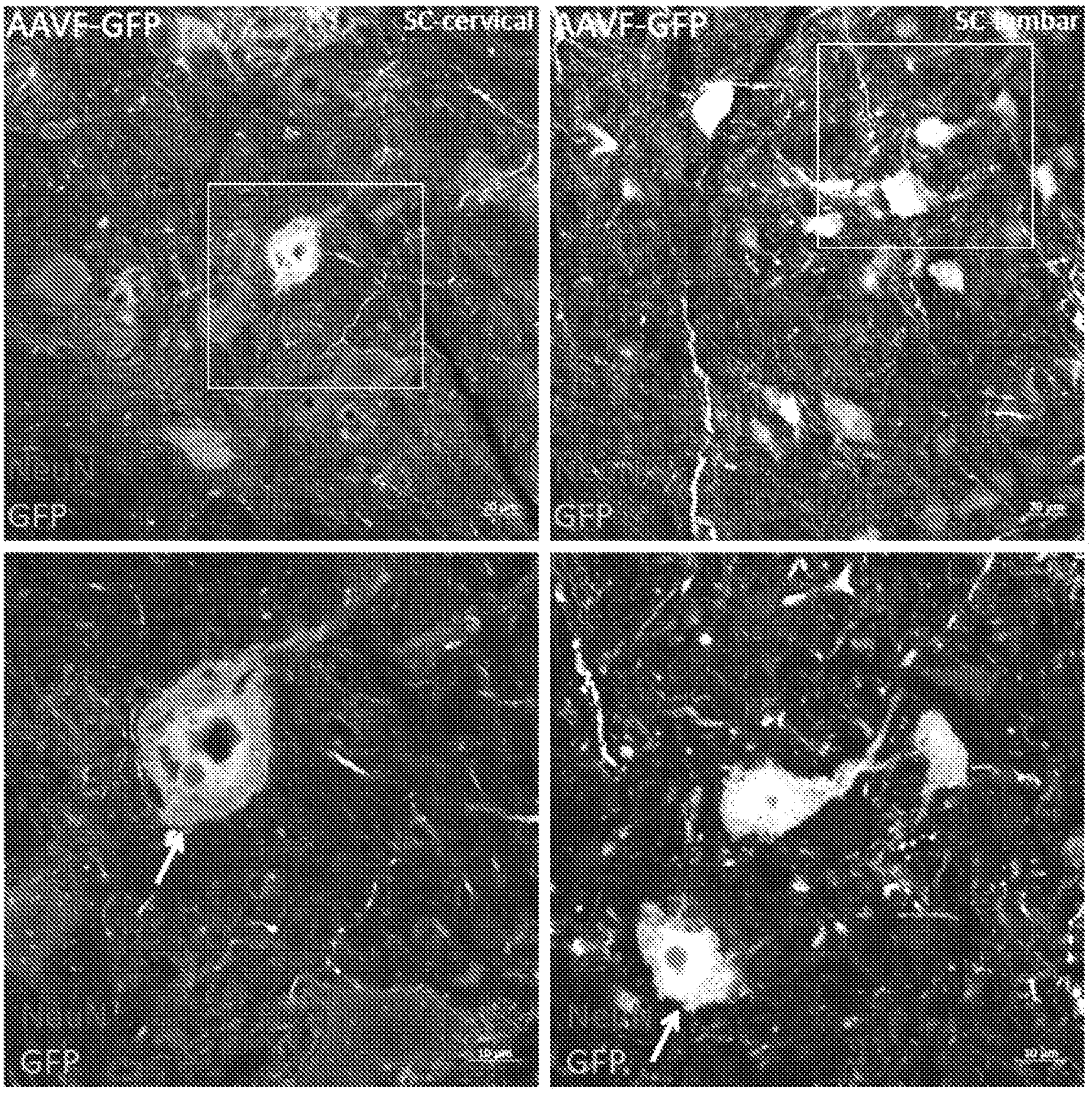
Figure 14E:
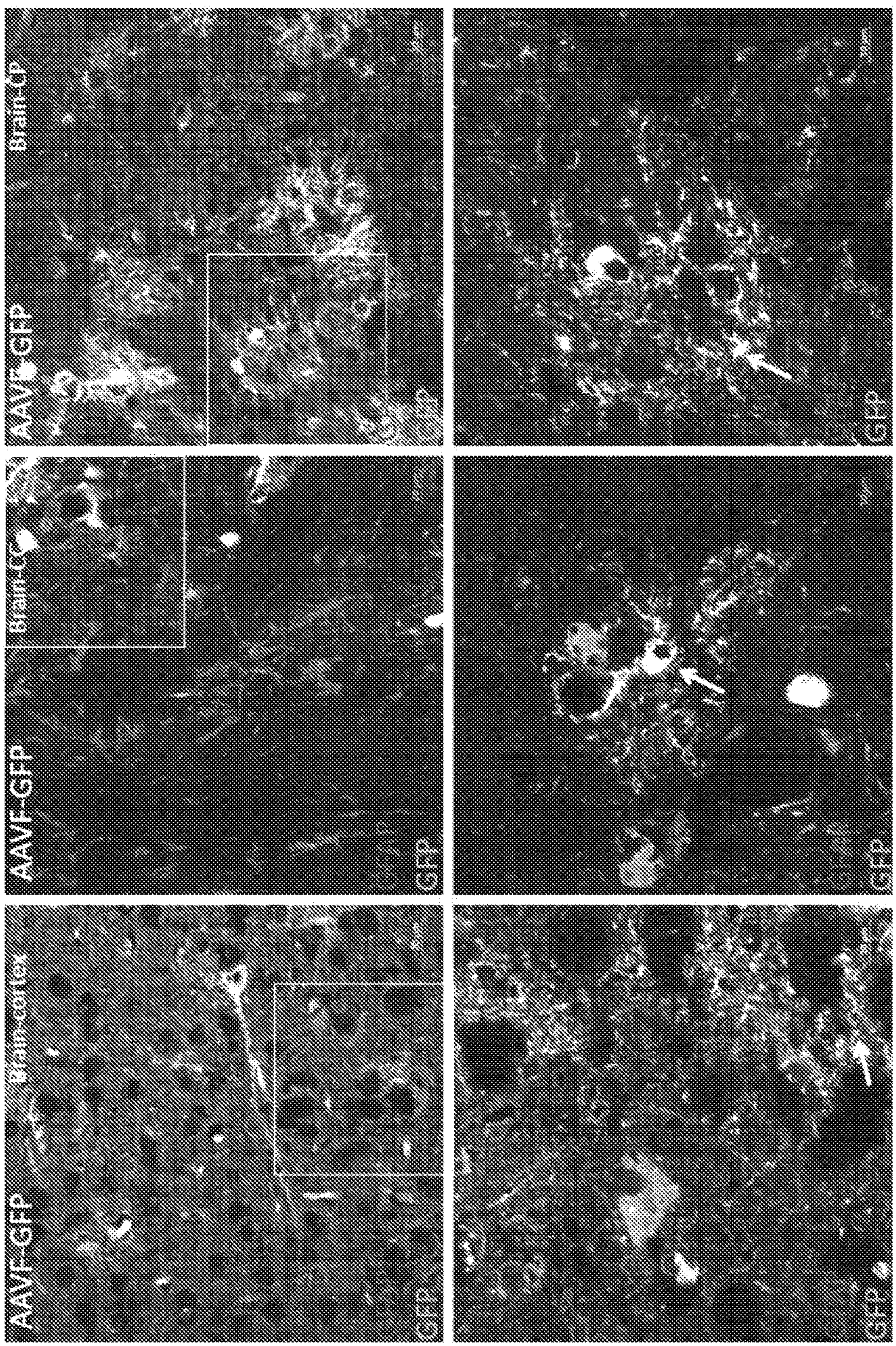
Figure 14F:
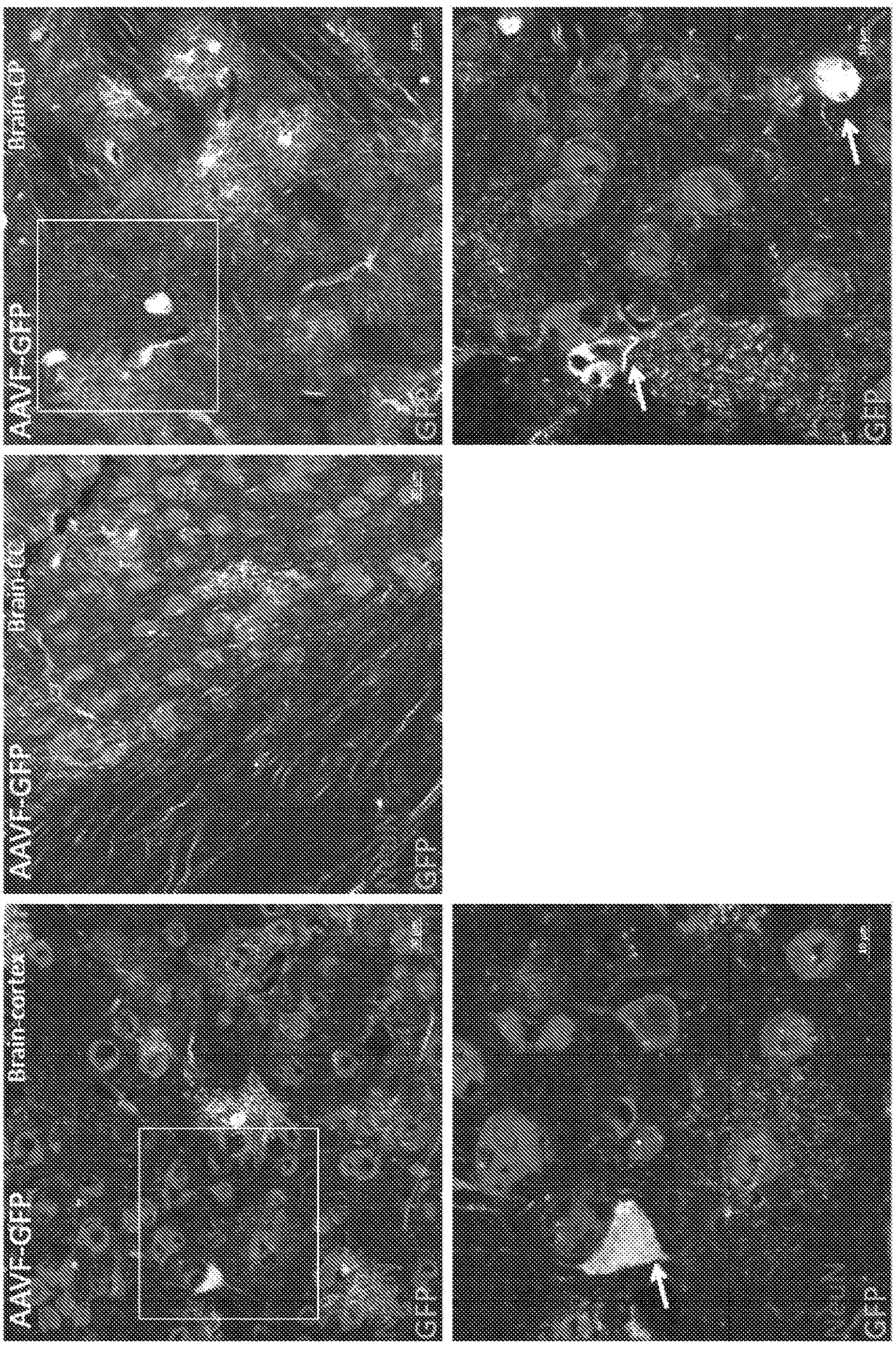

FIG. 13. Sustained neural transduction after direct intracranial injection of AAV-F and AAV-S. Representative images of GFP fluorescence signal (and DAPI) across mouse brain sagittal sections after direct intracortical and intrahippocampal injections of AAV-F (upper panels) or AAV-S (lower panels) ($1.65\times10^{10}$ and $5.6\times10^{10}$ gc/injection site for AAV-F and AAV-S, respectively). Scale bar: 1000 m for the low-magnification images of full brain and 200 m for Higher-magnification images of the cortex and hippocampus.

FIGS. 14A-F. Widespread transduction of spinal cord and brain after lumbar intrathecal injection of AAV-F vector. Ten microliters of AAV9 ($1.25\times10^{11}$ vg) or AAV-F ($8.8\times10^{10}$ vg) packaging a single stranded AAV-CBA-GFP expression cassette were injected intrathecally in the lumbar region of adult mice (n=2/vector). Three weeks later, mice were killed and spinal cord and brain analyzed for GFP expression after anti-GFP immunostaining. (a) Top images: Full coronal brain section scans showing robust transduction of brain with AAV-F but not AAV9. Lower images: Full section scans of spinal cord with AAV-F and AAV9. AAV-F injected mice showed very high GFP signal. AAV9 showed very low expression in both mice. All images were taken at an exposure time of 33 ms; an additional image at 4 ms was taken for AAV-F to better resolve features. White outlines of section limits are included where section is dim. Where not listed, scale bars equal 250 m. (b-d) High magnification images of spinal cords from mice treated with AAV9 (b) and AAV-F (c,d). GFAP indicates astrocyte-specific staining and NeuN for neurons. The area of the spinal cord is indicated in the upper right of each image. Images in lower panels are higher magnification images of the boxed in area in the upper image. (e, f) High magnification images of AAV-F transduced brain after intrathecal injection. (e) depicts astrocytes (f) neurons transduced by AAV-F. AAV9 did not mediate detectable transduction of brain after intrathecal injection. SC, spinal cord; CC, corpus callosum, CP, caudate putamen.

FIGS. 15A-D. GFP fluorescence following AAV-S-CBA-GFP administration to the inner ear. (a,b): Representative images of cochlear sensory epithelium transduced with AAV-S(63× magnification). (c): Transduction in the spiral limbus. (d): Transduction in spiral ganglion region. Z and arrow indicates different layers of Z-stack. OHC: outer hair cells. IHC: inner hair cells.

Figure 16A:
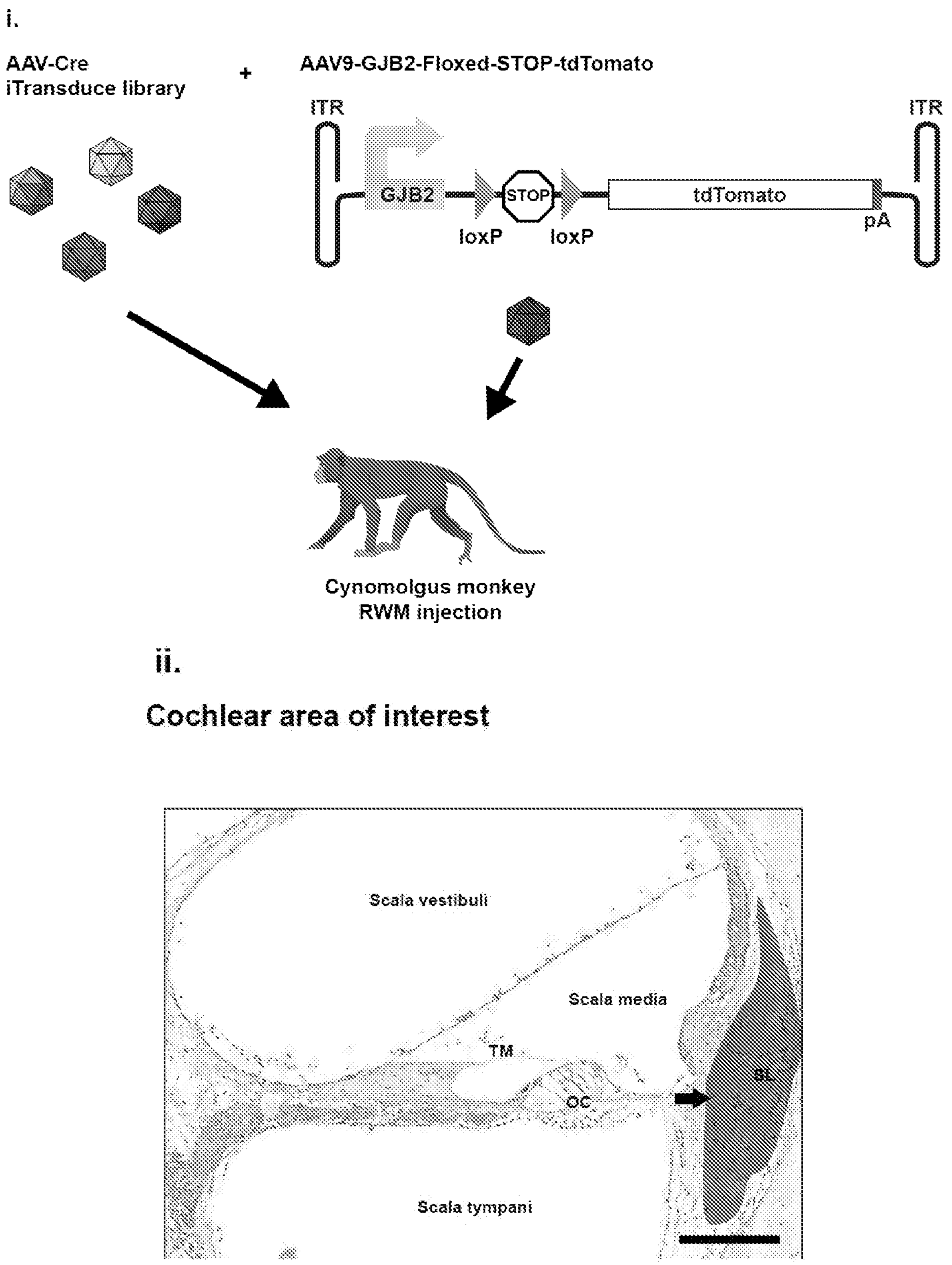
Figure 16B:
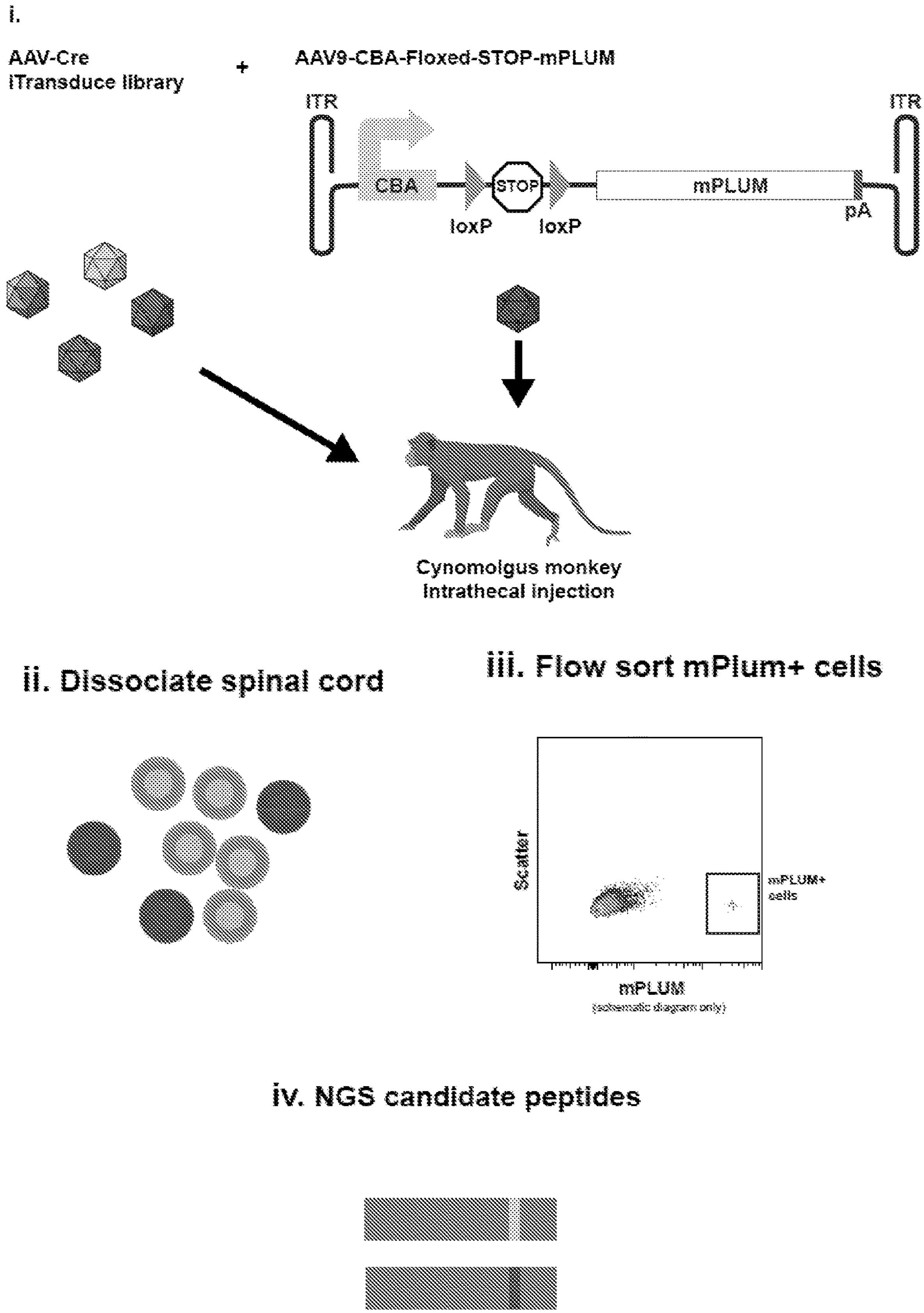

FIGS. 16A-B. Use of the iTransduce library in non-transgenic NHP to select AAV capsids that efficiently transduce inner-ear fibrocytes and spinal cord. (A) i. Cynomolgus monkeys (or other non-human primates) are co-injected with the AAV capsid library along with an AAV9-PHP.B encoding a GJB2-driven floxed-Stop-tdTomato cassette. ii. AAV9-PHP.B will selectively express tdTomato in fibrocytes (indicating by shading) when an AAV library capsid expresses Cre. iii. the inner ear is dissociated and iv. tdTomato positive fibrocytes are flow-sorted. v. Potentially functional capsids are PCR-amplified from recovered DNA from the sorted cells, the library is repackaged and another round of selection is performed. Next generation DNA sequencing analysis is utilized after each round to monitor selection process. Abbreviations: TM, tectorial membrane; OC, organ of Corti; SL, spiral ligament. (B). i. Cynomolgus monkeys (or other non-human primates) are co-injected with the AAV capsid library along with an AAV9-encoding a CBA-driven floxed-Stop-mPlum cassette. ii., iii. AAV9 will express mPlum in spinal cord (indicating by shading) when an AAV library capsid expresses Cre. The spinal cord is dissociated and mPlum positive cells are flow-sorted. iv. Potentially functional capsids are PCR-amplified from recovered DNA from the sorted cells, the library is repackaged and another round of selection is performed. Next generation DNA sequencing analysis is utilized after each round to monitor selection process.

DETAILED DESCRIPTION

A promising approach to efficient delivery of transgenes to target cells is via a process of submitting a pool, or library, of AAV vector capsids variants to an in vivo selection process—a veritable "survival of the fittest" approach[4-8]. AAV library approaches which use random oligomer nucleotides to insert short (6-9 amino acid) random peptides into an exposed region on the capsid surface have demonstrated success in identifying new AAV capsid variants with unique properties such as enhanced transduction of target tissues[9, 10]. One major limitation of AAV libraries is that the end readout of the selection process does not always differentiate capsids which mediate functional transgene expression from those which do not. AAV transduction is a process involving multiple steps, from cell receptor binding and entry to nuclear transport, second-strand synthesis and finally gene and protein expression[11]. A recent advance on the conventional AAV library approach, called CREATE, engineered a Cre-sensitive AAV genome which enabled selectively isolate capsids that have successfully trafficked to the nucleus in the context of a Cre-expressing transgenic animal[12]. Herein is described a capsid selection system, one example of which is called iTransduce, that utilizes the power of the Cre/loxP system. Instead of using Cre transgenic mice, the AAV was engineered to encode both the capsids with peptide inserts, along with a Cre-expression cassette. Selection was then performed in mice with a Cre-sensitive fluorescent reporter to enable selection of capsids which mediate the entire process of transduction including transgene expression. In vivo selection of the library resulted in the identification of an AAV capsid that mediates remarkable transduction efficiency of the CNS, and another capsid that mediates transduction in the inner ear.

Using the iTransduce system, we have isolated two new AAV capsids, referred to herein as AAV-F and AAV-S, which mediate highly efficient transgene expression in the murine CNS (two strains tested) and inner ear, respectively. The AAV-F capsid also mediated robust transduction of primary human neurons.

Interestingly, using expression-based selection, 3 peptide clones (STTLYSP (SEQ ID NO:1), FVVGQSY (SEQ ID NO:2), and FQPCP* (SEQ ID NO:3) were identified that represented 97% of NGS reads. Since FQPCP* had a stop codon, it was reasoned that this genome was cross-packaged in another capsid during production, a phenomenon noted to occur with AAV libraries[15]. This may also be the case for STTLYSP (SEQ ID NO:1, "AAV-S"), (FIG. 2). AAV-S was not a defective vector, as it mediated robust transduction of peripheral organs (FIG. 4*e*) and the inner ear (FIG. 15). Since it had such a high production efficiency (Table 4), AAV-S may have had a propensity to be cross-packaged. On the other hand, AAV-F (FVVGQSY (SEQ ID NO:2)) was extremely efficient at transduction and was one of only two prospective candidates from the NGS (FIG. 2). Both of these candidates were detectable at very low levels in the Round 2 library pool (FIG. 2)—as such, we could confirm that their enrichment was not due to a preexisting bias.

Since we performed a demonstration of the iTransduce system using an agnostic approach to cell type (whole brain), it is not surprising that AAV-F was highly tropic to astrocytes and neurons, cells that are transduced by AAV9. In future studies we will combine cell specific promoters to drive Cre expression from the AAV library vector as well as magnetic cell sorting to isolate capsids that can transduce cells that are refractory to conventional AAV vector transduction.

In addition to the potential of the iTransduce system to select clinical candidate AAV vectors, it can be used to identify vectors for use as research tools. The recently identified AAV-PHP.B capsid has served as an efficient vector to genetically modify the murine brain[12]. However, it does not transduce BALB/c or BALB/c related mouse lineages[13, 14 16] Interestingly, robust transduction of BALB/c and C57BL/6 murine brain was observed after intravenous injection of AAV-F. This indicates that the mechanism of enhanced transduction over AAV9 differs between AAV-PHP.B and AAV-F. It also enables AAV-F to be utilized as an efficient tool for CNS research in the popular BALB/c strain (labome.com/method/Laboratory-Mice-and-Rats.html). Additionally, as shown herein AAV-F can also mediate robust transgene expression in the CNS after both direct and intrathecal bolus injection, and AAV-S can mediate transgene expression in the inner ear.

Future studies in larger animals can be carried out to further test AAV-F, e.g., in preclinical studies. Dose escalation studies can be performed to test for dose-related toxicity of AAV-F, as was observed with PHP.B in NHPs.[14]. Iterative rounds of selection can be done in different species (e.g. mice then rats) to allow better cross-species translation of the transduction efficiency. For example, this could be done in mice followed by floxed STOP tdTomato transgenic rats[17]. Alternatively, direct selection of the iTransduce library can be performed in transgenic marmosets[18, 19] or even in other non-human non-transgenic primates (FIGS. 16A and B).

Methods of Identifying Optimized Capsid Sequences

"Virus vector libraries" are pooled variants of viruses, which under selective pressure (in vivo or in vitro) can drive isolation of clones of viruses specific for a target cell/tissue/organ of interest. One limitation of current library technologies is that many of the candidate virus clones do not mediate transgene expression (the required final function of the vector). The main reason for this limitation is that there has been no strategy devised to allow vector selection based on vector-mediated transgene expression. Described herein are methods that use an adeno-associated virus (AAV) vector genome with a two-part expression cassette. The first is a Cre-recombinase cassette under a promoter of interest. The second part is an AAV promoter to drive expression of the capsid gene, cloned "in cis" to the first section of the viral genome. Virus vectors can now be selected for transgene expression (highly sensitive Cre expression) using cells that express a reporter gene (e.g., green fluorescent protein) with an upstream loxP/stop site, thus preventing reporter expression until AAV vector-delivered Cre removes the stop site. Reporter gene positive cells can be isolated and recovered AAV capsid sequences will have a higher likelihood of mediating efficient transgene expression.

Figure 1A:
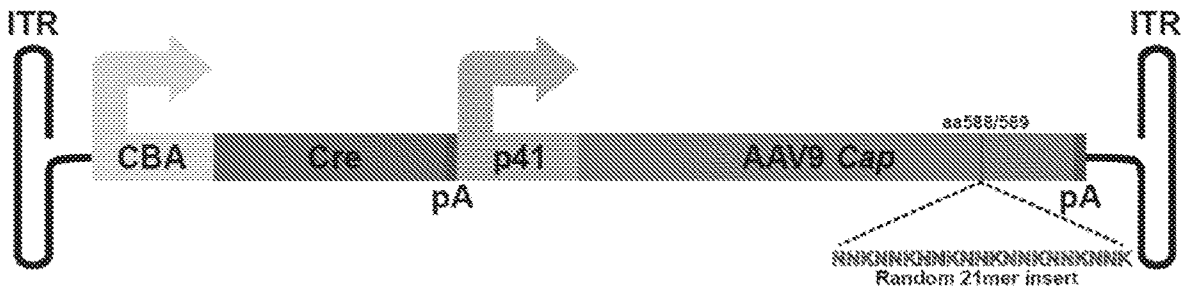
FIGS. 1A-B. iTransduce library for selection of novel AAV capsids capable of efficient transgene expression in target tissue. a. Two-component system of the library construct. 1. Cre recombinase is driven by a minimal chicken beta actin (CBA) promoter. 2. p41 promoter driven AAV9 capsid with random heptamer peptide inserted between aa 588-589, cloned downstream of the Cre cassette. b. Selection strategy. i. The iTransduce library comprised of different peptide inserts expressed on the capsid (represented by different colors), are injected i.v. into Ai9 transgenic mouse with a loxP-flanked STOP cassette upsteam of the tdTomato reporter gene, inserted into the Gt(ROSA)26Sor locus. AAV capsids able to enter the cell of interest but do not functionally transduce the cell (no Cre expression) do not turn on tdTomato expression. Capsids that can mediate functional transduction (express Cre) will turn on tdTomato expression. ii. Cells are isolated from the organ of interest (e.g. brain), and transduced cells are sorted for tdTomato expression and optionally cell markers. iii. Capsid DNA is PCR-amplified from the sorted cells, cloned back to the library vector and repackaged for another round of selection. DNA sequencing analysis is utilized after each round to monitor selection process.

Thus provided herein are library construct AAVs comprising: (i) a Cre recombinase driven by a promoter, e.g., a minimal chicken beta actin (CBA) promoter; (ii) a promoter (e.g., p41 promoter)-driven AAV9 capsid sequence with a sequence encoding a peptide as described herein, e.g., a random heptamer peptide or selected heptamer peptide, inserted into a capsid protein, downstream of the Cre cassette. Preferably the peptide is inserted between the sequences encoding amino acids (aa) 588-589 of the capsid, but it can also be inserted elsewhere as long as it doesn't interfere with function of the virus and maintains its activity in promoting infection of selected cells, e.g., at the VP1/VP2 interface (amino acid 138) or any site between 583-590. The CBA promoter is strong, active promoter to drive Cre in most cell types. The P41 promoter is an AAV specific natural promoter which drives Cap gene expression Other promoters that can be used include, but are not limited to, Synapsin promoter, GFAP promoter, CD68 promoter, F4/80 promoter, CX3CR1 promoter, CD3 or CD4 promoter, CMV promoter, liver specific promoter; other examples are listed below. The constructs can also include a stop codon at the end of the Cre cDNA and at the end of the cap DNA. There are poly A signals after the Cre cassette and the cap cassette. Cre recombinases are known in the art, see, e.g., Van Duyne, Microbiol Spectr. 2015 February; 3(1):MDNA3-0014-2014. FIG. 1A provides an exemplary library construct.

Also provided herein are libraries (i.e., compositions comprising a plurality of the library constructs). Where random heptamer sequences are used, preferably the library comprises constructs with sequences encoding all or almost all possible variants of the heptamer).

Figure 1B:
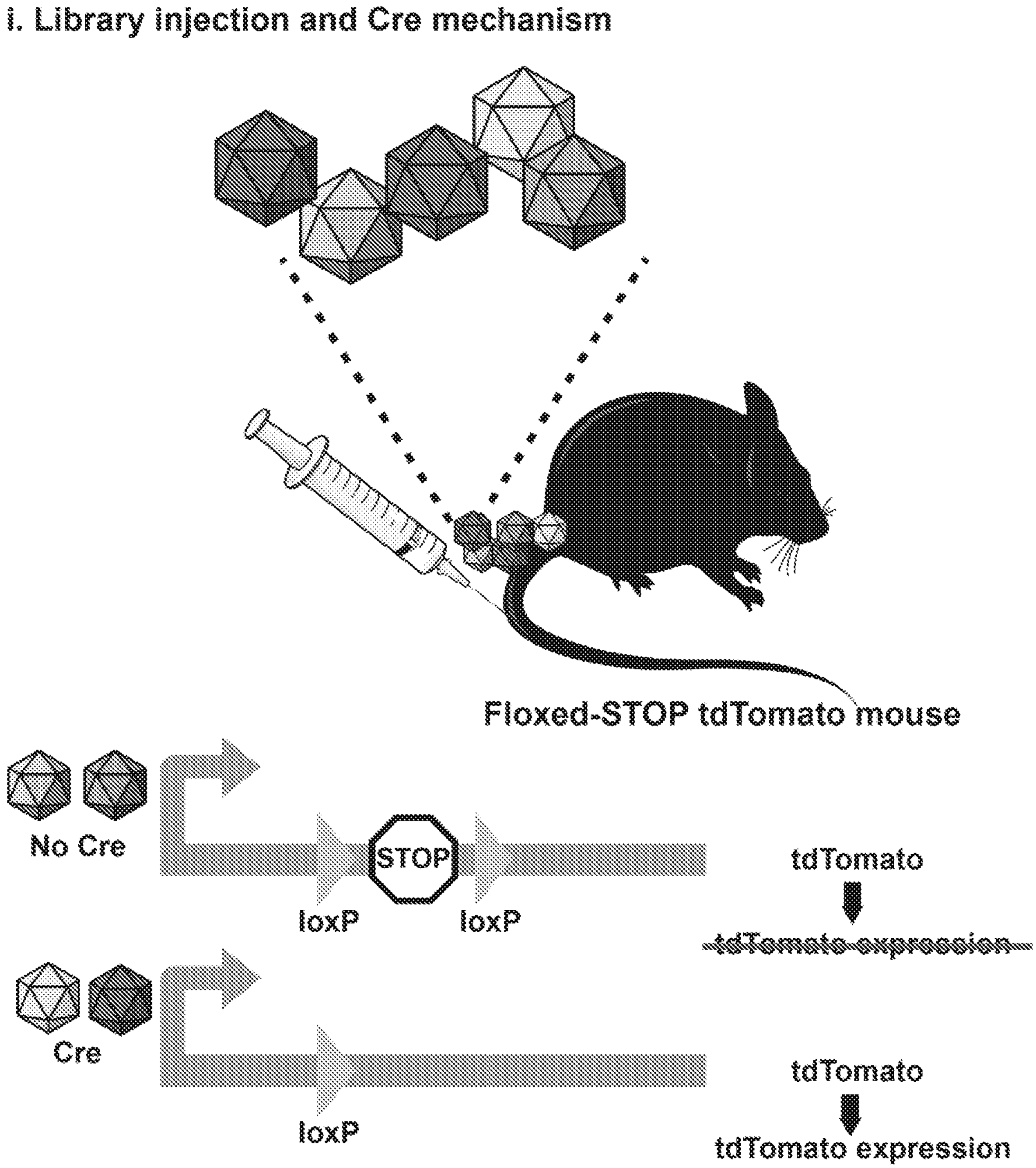

The methods, illustrated in FIG. 1B(i), can include administering a library comprised of different peptide inserts expressed on the capsid (represented by different shades of gray) to a model animal, e.g., a mammal such as a mouse (e.g., an Ai9 transgenic mouse), rabbit, rat, or monkey. The model animal comprises a loxP-flanked STOP cassette upstream of a reporter sequence, e.g., a fluorescent reporter protein sequence, e.g., a tdTomato reporter gene, optionally inserted into a Gt(ROSA)26Sor locus. The model animal can be transgenic, or the loxP-flanked STOP cassette upstream of a reporter sequence can be expressed from a second construct, e.g., a second AAV administered to the animal model (e.g., administered before, after, or concurrently with the library constructs). Any AAV capsids that enter the cell of interest but do not functionally transduce the cell (no Cre expression) do not turn on expression of the reported. Capsids that can mediate functional transduction (express Cre) will turn on tdTomato expression. As shown in FIG. 1B(ii), cells are isolated from the organ of interest (e.g., brain, eye, ear, retina, heart, etc.), and then transduced cells can then be sorted for reporter gene expression and optionally cell markers. As shown in FIG. 1B(iii), capsid DNA is obtained and analyzed, e.g., optionally by PCR-amplifying sequences from the sorted cells, cloning them back to the library vector and repackaged for another round of selection. DNA sequencing analysis can be utilized after each round to monitor selection process.

Promoters

The library constructs described herein include two promoters; one driving the Cre recombinase, and a second driving the AAV capsid sequence.

A number of promoter sequences are known in the art, including so-called "ubiquitous" promoters that drive expression in most cell types, e.g., cytomegalovirus (CMV) promoter (optionally with the CMV enhancer), chicken beta-actin (CBA) promoter, Rous sarcoma virus (RSV) LTR promoter (optionally with the RSV enhancer), SV40 promoter, dihydrofolate reductase promoter, phosphoglycerol kinase promoter, phosphoglycerol kinase (PGK) promoter, EFlalpha promoter, Ubiquitin C (UBC), B-glucuronidase (GUSB), and CMV immediate/early gene enhancer/CBA promoter.

Expression of the Cre-recombinase can also be driven by a tissue-specific promoter, e.g., a tissue-specific promoter for CNS, liver, heart cochlea, retina, or T cells, inter alia. In some embodiments, the tissue specific promoter for CNS includes neuronal, macrophage/microglial promoter and astrocyte promoters. A number of tissue specific promoters are known in the art, including synapsin promoter (neurons), neuron-specific enolase (NSE) (neurons), MeCP2 (methyl-CPG binding protein 2) (neurons), a glial fibrillary acidic protein (GFAP) (astrocytes), oligodendrocyte transcription factor 1 (Olig1) (oligodendrocytes), CNP (2',3'-Cyclic-nucleotide 3'-phosphodiesterase) (broad), or CBh (hybrid CBA or a MVM intron with CBA promoter)(broad). See, e.g., US20190032078. Macrophage/microglial promoters include, but are not limited to, a C-X3-C motif chemokine receptor 1 (CX3CR1) promoter, CD68 promoter, an ionized calcium binding adaptor molecule 1 (IBA1) promoter, a transmembrane protein 119 (TMEM119) promoter, a spalt like transcription factor 1 (SALL1) promoter, an adhesion G protein-coupled receptor E1 (F4/80) promoter, a myeloproliferative sarcoma virus enhancer, negative control region deleted, d1587rev primer-binding site substituted (MND) promoter; integrin subunit alpha M (ITGAM; CD11b-myeloid cells (neutrophils, monocytes, and macrophages)) promoter. For expression in the inner ear, the promoter can be, e.g., a PKG, CAG, prestin, Atoh1, POU4F3, Lhx3, Myo6, α9AchR, α10AchR, oncomod, or myo7A promoter; see Ryan et al., Adv Otorhinolaryngol. 2009; 66: 99-115.

Reporter Proteins

A number of reporter proteins are known in the art, and include green fluorescent protein (GFP), variant of green fluorescent protein (GFP10), enhanced GFP (eGFP), TurboGFP, GFPS65T, TagGFP2, mUKGEmerald GFP, Superfolder GFP, GFPuv, destabilised EGFP (dEGFP), Azami Green, mWasabi, Clover, mClover3, mNeonGreen, NowGFP, Sapphire, T-Sapphire, mAmetrine, photoactivatable GFP (PA-GFP), Kaede, Kikume, mKikGR, tdEos, Dendra2, mEosFP2, Dronpa, blue fluorescent protein (BFP), eBFP2, azurite BFP, mTagBFP, mKalamal, mTagBFP2, shBFP, cyan fluorescent protein (CFP), eCFP, Cerulian CFP, SCFP3A, destabilised ECFP (dECFP), CyPet, mTurquoise, mTurquoise2, mTFPI, photoswitchable CFP2 (PS-CFP2), TagCFP, mTFP1, mMidoriishi-Cyan, aquamarine, mKeima, mBeRFP, LSS-mKate2, LSS-mKate1, LSS-mOrange, CyOFP1, Sandercyanin, red fluorescent protein (RFP), eRFP, mRaspberry, mRuby, mApple, mCardinal, mStable, mMaroonl, mGarnet2, tdTomato, mTangerine, mStrawberry, TagRFP, TagRFP657, TagRFP675, mKate2, HcRed, t-HcRed, HcRed-Tandem, mPlum, mNeptune, NirFP, Kindling, far red fluorescent protein, yellow fluorescent protein (YFP), eYFP, destabilised EYFP (dEYFP), TagYFP, Topaz, Venus, SYFP2, mCherry, PA-mCherry, Citrine, mCitrine, Ypet, IANRFP-AS83, mPapayal, mCyRFP1, mHoneydew, mBanana, mOrange, Kusabira Orange, Kusabira Orange 2, mKusabira Orange, mOrange 2, mKOK, mKO2, mGrape1, mGrape2, zsYellow, eqFP611, Sirius, Sandercyanin, shBFP-N158S/L173I, near infrared proteins, iFP1.4, iRFP713, iRFP670, iRFP682, iRFP702, iRFP720, iFP2.0, mIFP, TDsmURFP, miRFP670, Brilliant Violet (BV) 421, BV 605, BV 510, BV 711, BV786, PerCP, PerCP/Cy5.5, DsRed, DsRed2, mRFPl, pocilloporin, Renilla GFP, Monster GFP, paGFP, or a Phycobiliprotein, or a biologically active variant or fragment of any one thereof.

Kits

Also provided herein are kits comprising one or more library construct AAVs as described herein, with or without the random heptamer sequences. The kits can also include a construct comprising a loxP-flanked STOP cassette upstream of a reporter sequence.

Engineered AAV Capsid Proteins

The present methods identified two peptide sequences that alter the ability of an AAV to mediate transgene expression in specified cells when inserted into the capsid of the AAV, e.g., AAV1, AAV2, AAV8, or AAV9. In some embodiments, the peptides comprise sequences of at least 7 amino acids. In some embodiments, the amino acid sequence comprises at least 4, e.g., 5, 6, or 7 contiguous amino acids of the sequences (STTLYSP (SEQ ID NO: 1) or FVVGQSY (SEQ ID NO:2).

Peptides including reversed sequences can also be used, e.g., PSYLTTS (SEQ ID NO:4) and YSQGVVF (SEQ ID NO:5). Alternatively, the peptides can comprise at least four, five, or six contiguous amino acids from the sequences shown in FIG. 2A or 7C (SEQ ID NOs:17-150).

AAVs

Viral vectors for use in the present methods, kits and compositions include recombinant retroviruses, adenovirus, adeno-associated virus, alphavirus, and lentivirus, preferably comprising a capsid peptide as described herein and optionally a transgene for expression in a target tissue.

A preferred viral vector system useful for delivery of nucleic acids in the present methods is the adeno-associated virus (AAV). AAV is a tiny non-enveloped virus having a 25 nm capsid. No disease is known or has been shown to be associated with the wild type virus. AAV has a single-stranded DNA (ssDNA) genome. AAV has been shown to exhibit long-term episomal transgene expression, and AAV has demonstrated excellent transgene expression in the brain, particularly in neurons. Space for exogenous DNA is limited to about 4.7 kb. An AAV vector such as that described in Tratschin et al., Mol. Cell. Biol. 5:3251-3260 (1985) can be used to introduce DNA into cells. A variety of nucleic acids have been introduced into different cell types using AAV vectors (see for example Hermonat et al., Proc. Natl. Acad. Sci. USA 81:6466-6470 (1984); Tratschin et al., Mol. Cell. Biol. 4:2072-2081 (1985); Wondisford et al., Mol. Endocrinol. 2:32-39 (1988); Tratschin et al., J. Virol. 51:611-619 (1984); and Flotte et al., J. Biol. Chem. 268: 3781-3790 (1993). There are numerous alternative AAV variants (over 100 have been cloned), and AAV variants have been identified based on desirable characteristics. In some embodiments, the AAV is AAV1, AAV2, AAV3, AAV4, AAV5, AAV6, AV6.2, AAV7, AAV8, rh.8, AAV9, rh.10, rh.39, rh.43 or CSp3; for CNS use, in some embodiments the AAV is AAV1, AAV2, AAV4, AAV5, AAV6, AAV8, or AAV9. As one example, AAV9 has been shown to somewhat efficiently cross the blood-brain barrier. Using the present methods, the AAV capsid can be genetically engineered to increase permeation across the BBB, or into a specific tissue, by insertion of a peptide sequence as described herein into the capsid protein, e.g., into the AAV9 capsid protein VP1 between amino acids 588 and 589.

An exemplary wild type AAV9 capsid protein VP1 (Q6JC40-1) sequence is as follows:

```
                                        (SEQ ID NO: 6)
         10         20         30         40
MAADGYLPDW LEDNLSEGIR EWWALKPGAP QPKANQQHQD

         50         60         70         80
NARGLVLPGY KYLGPGNGLD KGEPVNAADA AALEHDKAYD

         90        100        110        120
QQLKAGDNPY LKYNHADAEF QERLKEDTSF GGNLGRAVFQ

        130        140        150        160
AKKRLLEPLG LVEEAAKTAP GKKRPVEQSP QEPDSSAGIG

        170        180        190        200
KSGAQPAKKR LNFGQTGDTE SVPDPQPIGE PPAAPSGVGS

        210        220        230        240
LTMASGGGAP VADNNEGADG VGSSSGNWHC DSQWLGDRVI

        250        260        270        280
TTSTRTWALP TYNNHLYKQI SNSTSGGSSN DNAYFGYSTP

        290        300        310        320
WGYFDFNRFH CHFSPRDWQR LINNNWGFRP KRLNFKLFNI
```

-continued

```
        330        340        350        360
QVKEVTDNNG VKTIANNLTS TVQVFTDSDY QLPYVLGSAH

        370        380        390        400
EGCLPPFPAD VFMIPQYGYL TLNDGSQAVG RSSFYCLEYF

        410        420        430        440
PSQMLRTGNN FQFSYEFENV PFHSSYAHSQ SLDRLMNPLI

        450        460        470        480
DQYLYYLSKT INGSGQNQQT LKFSVAGPSN MAVQGRNYIP

        490        500        510        520
GPSYRQQRVS TTVTQNNNSE FAWPGASSWA LNGRNSLMNP

        530        540        550        560
GPAMASHKEG EDRFFPLSGS LIFGKQGTGR DNVDADKVMI

        570        580        590        600
TNEEEIKTTN PVATESYGQV ATNHQSAQAQ AQTGWVQNQG

        610        620        630        640
ILPGMVWQDR DVYLQGPIWA KIPHTDGNFH PSPLMGGFGM

        650        660        670        680
KHPPPQILIK NTPVPADPPT AFNKDKLNSF ITQYSTGQVS

        690        700        710        720
VEIEWELQKE NSKRWNPEIQ YTSNYYKSNN VEFAVNTEGV

        730
YSEPRPIGTR YLTRNL
```

Thus provided herein are AAV that include one or more of the peptide sequences described herein, e.g., an AAV comprising a capsid protein comprising a sequence described herein, e.g., a capsid protein comprising SEQ ID NO:1 or SEQ ID NO:2, wherein a peptide sequence has been inserted into the sequence, e.g., between amino acids 588 and 589.

Exemplary sequences of AAVs are provided below. The inserted peptide sequences are bold and double-underlined highlighted in the protein sequences, and bold and capitalized in the DNA sequences.

AAV-F capsid protein sequence (SEQ ID NO: 7)

MAADGYLPDWLEDNLSEGIREWWALKPGAPQPKANQQHQDNARGLVLPGY

KYLGPGNGLDKGEPVNAADAAALEHDKAYDQQLKAGDNPYLKYNHADAEF

QERLKEDTSFGGNLGRAVFQAKKRLLEPLGLVEEAAKTAPGKKRPVEQSP

QEPDSSAGIGKSGAQPAKKRLNFGQTGDTESVPDPQPIGEPPAAPSGVGS

LTMASGGGAPVADNNEGADGVGSSSGNWHCDSQWLGDRVITTSTRTWALP

TYNNHLYKQISNSTSGGSSNDNAYFGYSTPWGYFDFNRFHCHFSPRDWQR

LINNNWGFRPKRLNFKLFNIQVKEVTDNNGVKTIANNLTSTVQVFTDSDY

QLPYVLGSAHEGCLPPFPADVFMIPQYGYLTLNDGSQAVGRSSFYCLEYF

PSQMLRTGNNFQFSYEFENVPFHSSYAHSQSLDRLMNPLIDQYLYYLSKT

INGSGQNQQTLKFSVAGPSNMAVQGRNYIPGPSYRQQRVSTTVTQNNNSE

FAWPGASSWALNGRNSLMNPGPAMASHKEGEDRFFPLSGSLIFGKQGTGR

DNVDADKVMITNEEEIKTTNPVATESYGQVATNHQSAQFVVGQSYAQAQT

GWVQNQGILPGMVWQDRDVYLQGPIWAKIPHTDGNFHPSPLMGGFGMKHP

PPQILIKNTPVPADPPTAFNKDKLNSFITQYSTGQVSVEIEWELQKENSK

RWNPEIQYTSNYYKSNNVEFAVNTEGVYSEPRPIGTRYLTRNL

-continued

AAV-F capsid DNA sequence (SEQ ID NO: 8)

atggctgccgatggttatcttccagattggctcgaggacaaccttagtga aggaattcgcgagtggtgggctttgaaacctggagcccctcaacccaagg caaatcaacaacatcaagacaacgctcgaggtcttgtgcttccgggttac aaataccttggacccggcaacggactcgacaagggggagccggtcaacgc agcagacgcggcggccctcgagcacgacaaggcctacgaccagcagctca aggccggagacaacccgtacctcaagtacaaccacgccgacgccgagttc caggagcggctcaaagaagatacgtcttttgggggcaacctcgggcgagc agtcttccaggccaaaaagaggcttcttgaacctcttggtctggttgagg aagcggctaagacggctcctggaaagaagaggcctgtagagcagtctcct caggaaccggactcctccgcgggtattggcaaatcgggtgcacagcccgc taaaaagagactcaatttcggtcagactggcgacacagagtcagtcccag accctcaaccaatcggagaacctcccgcagccccctcaggtgtgggatct cttacaatggcttcaggtggtggcgcaccagtggcagacaataacgaagg tgccgatggagtgggtagttcctcgggaaattggcattgcgattcccaat ggctgggggacagagtcatcaccaccagcacccgaacctgggccctgccc acctacaacaatcacctctacaagcaaatctccaacagcacatctggagg atcttcaaatgacaacgcctacttcggctacagcaccccctgggggtatt ttgacttcaacagattccactgccacttctcaccacgtgactggcagcga ctcatcaacaacaactggggattccggcctaagcgactcaacttcaagct cttcaacattcaggtcaaagaggttacggacaacaatggagtcaagacca tcgccaataaccttaccagcacggtccaggtcttcacggactcagactat cagctcccgtacgtgctcgggtcggctcacgagggctgcctcccgccgtt cccagcggacgttttcatgattcctcagtacgggtatctgacgcttaatg atggaagccaggccgtgggtcgttcgtccttttactgcctggaatatttc ccgtcgcaaatgctaagaacgggtaacaacttccagttcagctacgagtt tgagaacgtacctttccatagcagctacgctcacagccaaagcctggacc gactaatgaatccactcatcgaccaatacttgtactatctctcaaagact attaacggttctggacagaatcaacaaacgctaaaattcagtgtggccgg acccagcaacatggctgtccagggaagaaactacatacctggacccagct accgacaacaacgtgtctcaaccactgtgactcaaaacaacaacagcgaa tttgcttggcctggagcttcttcttgggctctcaatggacgtaatagctt gatgaatcctggacctgctatggccagccacaaagaaggagaggaccgtt tctttcctttgtctggatctttaatttttggcaaacaaggaactggaaga gacaacgtggatgcggacaaagtcatgataaccaacgaagaagaaattaa aactactaacccggtagcaacggagtcctatggacaagtggccacaaacc accagagtgcccaaTTTGTTGTTGGTCAGAGTTATgcacaggcgcagacc ggctgggttcaaaaccaaggaatacttccgggtatggtttggcaggacag agatgtgtacctgcaaggacccatttgggccaaaattcctcacacggacg gcaactttcacccttctccgctgatgggagggtttggaatgaagcacccg cctcctcagatcctcatcaaaaacacacctgtacctgcggatcctccaac -continued ggccttcaacaaggacaagctgaactctttcatcacccagtattctactg gccaagtcagcgtggagatcgagtgggagctgcagaaggaaaacagcaag cgctggaacccggagatccagtacacttccaactattacaagtctaataa tgttgaatttgctgttaatactgaaggtgtatatagtgaaccccgcccca ttggcaccagatacctgactcgtaatctg AAV-S capsid protein sequence (SEQ ID NO: 9)

MAADGYLPDWLEDNLSEGIREWWALKPGAPQPKANQQHQDNARGLVLPGY

KYLGPGNGLDKGEPVNAADAAALEHDKAYDQQLKAGDNPYLKYNHADAEF

QERLKEDTSFGGNLGRAVFQAKKRLLEPLGLVEEAAKTAPGKKRPVEQSP

QEPDSSAGIGKSGAQPAKKRLNFGQTGDTESVPDPQPIGEPPAAPSGVGS

LTMASGGGAPVADNNEGADGVGSSSGNWHCDSQWLGDRVITTSTRTWALP

TYNNHLYKQISNSTSGGSSNDNAYFGYSTPWGYFDFNRFHCHFSPRDWQR

LINNNWGFRPKRLNFKLFNIQVKEVTDNNGVKTIANNLTSTVQVFTDSDY

QLPYVLGSAHEGCLPPFPADVFMIPQYGYLTLNDGSQAVGRSSFYCLEYF

PSQMLRTGNNFQFSYEFENVPFHSSYAHSQSLDRLMNPLIDQYLYYLSKT

INGSGQNQQTLKFSVAGPSNMAVQGRNYIPGPSYRQQRVSTTVTQNNNSE

FAWPGASSWALNGRNSLMNPGPAMASHKEGEDRFFPLSGSLIFGKQGTGR

DNVDADKVMITNEEEIKTTNPVATESYGQVATNHQSAQSTTLYSPAQAQ

TGWVQNQGILPGMVWQDRDVYLQGPIWAKIPHTDGNFHPSPLMGGFGMKH

PPPQILIKNTPVPADPPTAFNKDKLNSFITQYSTGQVSVEIEWELQKENS

KRWNPEIQYTSNYYKSNNVEFAVNTEGVYSEPRPIGTRYLTRNL

AAV-S capsid DNA sequence (SEQ ID NO: 10)

atggctgccgatggttatcttccagattggctcgaggacaaccttagtga aggaattcgcgagtggtgggctttgaaacctggagcccctcaacccaagg caaatcaacaacatcaagacaacgctcgaggtcttgtgcttccgggttac aaataccttggacccggcaacggactcgacaagggggagccggtcaacgc agcagacgcggcggccctcgagcacgacaaggcctacgaccagcagctca aggccggagacaacccgtacctcaagtacaaccacgccgacgccgagttc caggagcggctcaaagaagatacgtcttttgggggcaacctcgggcgagc agtcttccaggccaaaaagaggcttcttgaacctcttggtctggttgagg aagcggctaagacggctcctggaaagaagaggcctgtagagcagtctcct caggaaccggactcctccgcgggtattggcaaatcgggtgcacagcccgc taaaaagagactcaatttcggtcagactggcgacacagagtcagtcccag accctcaaccaatcggagaacctcccgcagccccctcaggtgtgggatct cttacaatggcttcaggtggtggcgcaccagtggcagacaataacgaagg tgccgatggagtgggtagttcctcgggaaattggcattgcgattcccaat ggctgggggacagagtcatcaccaccagcacccgaacctgggccctgccc acctacaacaatcacctctacaagcaaatctccaacagcacatctggagg atcttcaaatgacaacgcctacttcggctacagcaccccctgggggtatt ttgacttcaacagattccactgccacttctcaccacgtgactggcagcga -continued ctcatcaacaacaactggggattccggcctaagcgactcaacttcaagct cttcaacattcaggtcaaagaggttacggacaacaatggagtcaagacca tcgccaataaccttaccagcacggtccaggtcttcacggactcagactat cagctcccgtacgtgctcgggtcggctcacgagggctgcctcccgccgtt cccagcggacgttttcatgattcctcagtacgggtatctgacgcttaatg atggaagccaggccgtgggtcgttcgtccttttactgcctggaatatttc ccgtcgcaaatgctaagaacgggtaacaacttccagttcagctacgagtt tgagaacgtacctttccatagcagctacgctcacagccaaagcctggacc gactaatgaatccactcatcgaccaatacttgtactatctctcaaagact attaacggttctggacagaatcaacaaacgctaaaattcagtgtggccgg acccagcaacatggctgtccagggaagaaactacatacctggacccagct accgacaacaacgtgtctcaaccactgtgactcaaaacaacaacagcgaa tttgcttggcctggagcttcttcttgggctctcaatggacgtaatagctt gatgaatcctggacctgctatggccagccacaaagaaggagaggaccgtt tctttcctttgtctggatctttaattttggcaaacaaggaactggaaga gacaacgtggatgcggacaaagtcatgataaccaacgaagaagaaattaa aactactaacccggtagcaacggagtcctatggacaagtggccacaaacc accagagtgcccaaTCTACTACGCTTTATAGTCCTgcacaggcgcagacc ggctgggttcaaaaccaaggaatacttccgggtatggtttggcaggacag agatgtgtacctgcaaggacccatttgggccaaaattcctcacacggacg gcaactttcacccttctccgctgatgggagggtttggaatgaagcacccg cctcctcagatcctcatcaaaaacacacctgtacctgcggatcctccaac ggccttcaacaaggacaagctgaactctttcatcacccagtattctactg gccaagtcagcgtggagatcgagtgggagctgcagaaggaaaacagcaag cgctggaacccggagatccagtacacttccaactattacaagtctaataa tgttgaatttgctgttaatactgaaggtgtatatagtgaaccccgcccca ttggcaccagatacctgactcgtaatctg The AAV sequences can be, e.g., at least 80, 85, 90, 95, 97, or 99% identical to a reference AAV sequence set forth herein, e.g., can include variants, preferable that do not reduce the ability of the AAV to mediate transgene expression in a cell. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 80% of the length of the reference sequence, and in some embodiments is at least 90% or 100%. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. For example, the percent identity between two amino acid sequences can determined using the Needleman and Wunsch ((1970) J. Mol. Biol. 48:444-453) algorithm which has been incorporated into the GAP program in the GCG software package (available on the world wide web at gcg.com), using the default parameters, e.g., a Blossum 62 scoring matrix with a gap penalty of 12, a gap extend penalty of 4, and a frameshift gap penalty of 5.

Transgenes

In some embodiments, the AAV also includes a transgene sequence (i.e., a heterologous sequence), e.g., a transgene encoding a therapeutic agent, e.g., as described herein or as known in the art, or a reporter protein, e.g., a fluorescent protein, an enzyme that catalyzes a reaction yielding a detectable product, or a cell surface antigen. The transgene is preferably linked to sequences that promote/drive expression of the transgene in the target tissue.

Exemplary transgenes for use as therapeutics include neuronal apoptosis inhibitory protein (NAIP), nerve growth factor (NGF), glial-derived growth factor (GDNF), brain-derived growth factor (BDNF), ciliary neurotrophic factor (CNTF), tyrosine hydroxlase (TH), GTP-cyclohydrolase (GTPCH), amino acid decarboxylase (AADC), aspartoacylase (ASPA), blood factors, such as β-globin, hemoglobin, tissue plasminogen activator, and coagulation factors; colony stimulating factors (CSF); interleukins, such as IL-1, IL-2, IL-3, IL-4, IL-5, IL-6, IL-7, IL-8, IL-9, etc.; growth factors, such as keratinocyte growth factor (KGF), stem cell factor (SCF), fibroblast growth factor (FGF, such as basic FGF and acidic FGF), hepatocyte growth factor (HGF), insulin-like growth factors (IGFs), bone morphogenetic protein (BMP), epidermal growth factor (EGF), growth differentiation factor-9 (GDF-9), hepatoma derived growth factor (HDGF), myostatin (GDF-8), nerve growth factor (NGF), neurotrophins, platelet-derived growth factor (PDGF), thrombopoietin (TPO), transforming growth factor alpha (TGF-α), transforming growth factor beta (TGF-β), and the like; soluble receptors, such as soluble TNF-α receptors, soluble VEGF receptors, soluble interleukin receptors (e.g., soluble IL-1 receptors and soluble type II IL-1 receptors), soluble gamma/delta T cell receptors, ligand-binding fragments of a soluble receptor, and the like; enzymes, such as α-glucosidase, imiglucarase, and β-glucocerebrosidase; enzyme activators, such as tissue plasminogen activator; chemokines, such as IP-10, monokine induced by interferon-gamma (Mig), Groa/IL-8, RANTES, MIP-1α, MIP-1β, MCP-1, PF-4, and the like; angiogenic agents, such as vascular endothelial growth factors (VEGFs, e.g., VEGF121, VEGF165, VEGF-C, VEGF-2), transforming growth factor-beta, basic fibroblast growth factor, glioma-derived growth factor, angiogenin, angiogenin-2, and the like; anti-angiogenic agents, such as a soluble VEGF receptor; protein vaccine; neuroactive peptides, such as nerve growth factor (NGF), bradykinin, cholecystokinin, gastin, secretin, oxytocin, gonadotropin-releasing hormone, beta-endorphin, enkephalin, substance P, somatostatin, prolactin, galanin, growth hormone-releasing hormone, bombesin, dynorphin, warfarin, neurotensin, motilin, thyrotropin, neuropeptide Y, luteinizing hormone, calcitonin, insulin, glucagons, vasopressin, angiotensin II, thyrotropin-releasing hormone, vasoactive intestinal peptide, a sleep peptide, and the like; thrombolytic agents; atrial natriuretic peptide; relaxin; glial fibrillary acidic protein; follicle stimulating hormone (FSH); human alpha-1 antitrypsin; leukemia inhibitory factor (LIF); transforming growth factors (TGFs); tissue factors, luteinizing hormone; macrophage activating factors; tumor necrosis factor (TNF); neutrophil chemotactic factor (NCF); nerve growth factor; tissue inhibitors of metalloproteinases; vasoactive intestinal peptide; angiogenin; angiotropin; fibrin; hirudin; IL-1 receptor antagonists; and the like. Some other examples of protein of interest include ciliary neurotrophic factor (CNTF); neurotrophins 3 and 4/5 (NT-3 and 4/5); glial cell derived neurotrophic factor (GDNF); aromatic amino acid decarboxylase (AADC); hemophilia related clotting proteins, such as Factor VIII, Factor IX, Factor X; dystrophin or nini-dystrophin; lysosomal acid lipase; phenylalanine hydroxylase (PAH); glycogen storage disease-related enzymes, such as glucose-6-phosphatase, acid maltase, glycogen debranching enzyme, muscle glycogen phosphorylase, liver glycogen phosphorylase, muscle phosphofructokinase, phosphorylase kinase (e.g., PHKA2), glucose transporter (e.g., GLUT2), aldolase A, β-enolase, and glycogen synthase; lysosomal enzymes (e.g., beta-N-acetylhexosaminidase A); and any variants thereof.

The transgene can also encode an antibody, e.g., an immune checkpoint inhibitory antibody, e.g., to PD-L1, PD-1, CTLA-4 (Cytotoxic T-Lymphocyte-Associated Protein-4; CD152); LAG-3 (Lymphocyte Activation Gene 3; CD223); TIM-3 (T-cell Immunoglobulin domain and Mucin domain 3; HAVCR2); TIGIT (T-cell Immunoreceptor with Ig and ITIM domains); B7-H3 (CD276); VSIR (V-set immunoregulatory receptor, aka VISTA, B7H5, C10orf54); BTLA 30 (B- and T-Lymphocyte Attenuator, CD272); GARP (Glycoprotein A Repetitions; Predominant; PVRIG (PVR related immunoglobulin domain containing); or VTCN1 (Vset domain containing T cell activation inhibitor 1, aka B7-H4).

Other transgenes can include small or inhibitory nucleic acids that alter/reduce expression of a target gene, e.g., siRNA, shRNA, miRNA, antisense oligos, or long non-coding RNAs that alter gene expression (see, e.g., WO2012087983 and US20140142160), or CRISPR Cas9/cas12a and guide RNAs.

The virus can also include one or more sequences that promote expression of a transgene, e.g. one or more promoter sequences; enhancer sequences, e.g. 5' untranslated region (UTR) or a 3' UTR; a polyadenylation site; and/or insulator sequences. In some embodiments, the promoter is a brain tissue specific promoter, e.g. a neuron-specific or glia-specific promoter. In certain embodiments, the promoter is a promoter of a gene selected from: neuronal nuclei (NeuN), glial fibrillary acidic protein (GFAP), MeCP2, adenomatous polyposis coli (APC), ionized calcium-binding adapter molecule 1 (Iba-1), synapsin I (SYN), calcium/calmodulin-dependent protein kinase II, tubulin alpha I, neuron-specific enolase and platelet-derived growth factor beta chain. In some embodiments, the promoter is a pan-cell type promoter, e.g., cytomegalovirus (CMV), beta glucuronidase, (GUSB), ubiquitin C (UBC), or rous sarcoma virus (RSV) promoter. The woodchuck hepatitis virus post-transcriptional response element (WPRE) can also be used.

In some embodiments, the AAV also has one or more additional mutations that increase delivery to the target tissue, e.g., the CNS, or that reduce off-tissue targeting, e.g., mutations that decrease liver delivery when CNS, heart, or muscle delivery is intended (e.g., as described in Pulicherla et al. (2011) Mol Ther 19:1070-1078); or the addition of other peptides, e.g., as described in Chen et al. (2008) Nat Med 15:1215-1218 or Xu et al., (2005) Virology 341:203-214 or U.S. Pat. Nos. 9,102,949; 9,585,971; and US20170166926. See also Gray and Samulski (2011) "Vector design and considerations for CNS applications," in *Gene Vector Design and Application to Treat Nervous System Disorders* ed. Glorioso J., editor. (Washington, DC: Society for Neuroscience;) 1-9, available at sfn.org/~/media/SfN/Documents/Short %20Courses/2011%20Short %20 Course %20I/2011_SC1_Gray.ashx.

Methods of Use

The methods and compositions described herein can be used to deliver any composition, e.g., a sequence of interest to a tissue, e.g., to the central nervous system (brain), heart, muscle, peripheral nervous system (e.g., dorsal root ganglion or spinal cord), or to the inner ear or retina. In some embodiments, the methods include delivery to specific brain regions, e.g., cortex, cerebellum, hippocampus, substantia nigra, amygdala. In some embodiments, the methods include lumbar delivery, e.g., into the subarachnoid space or epidural space. In some embodiments, the methods include delivery to neurons, astrocytes, or glial cells. In some embodiments, the methods include delivery to inner and/or outer hair cells, spiral ganglion neurons, supporting cells, or fibrocytes of the inner ear. In some embodiments, the methods include delivery to the photoreceptors, interneurons, retinal ganglion cells (e.g., using AAV-F), or retinal pigment epithelium (RPE) (e.g., using AAV-S) of the retina.

In some embodiments, the methods and compositions, e.g., AAVs, are used to deliver a nucleic acid sequence to a subject who has a disease, e.g., a disease of the CNS; see, e.g., U.S. Pat. Nos. 9,102,949; 9,585,971; and US20170166926. In some embodiments, the subject has a condition listed in Tables 1-3; in some embodiments, the vectors are used to deliver a therapeutic agent listed in Tables 1-3 for treating the corresponding disease listed in Tables 1-3. The therapeutic agent can be delivered as a nucleic acid, e.g. via a viral vector, wherein the nucleic acid encodes a therapeutic protein or other nucleic acid such as an antisense oligo, siRNA, shRNA, and so on; or as a fusion protein/complex with a peptide as described herein.

The methods and compositions described herein can be used to treat these conditions in a subject in need thereof, by administration of a therapeutically effective amount of an AAV carrying a therapeutic transgene, sufficient to ameliorate, reduce risk of, or delay onset of one or more symptoms of the condition.

TABLE 1

| CNS Targets (AAV-F, AAV-S) | | | |
|---|---|---|---|
| Disease | Target genes | Target cells/tissues | Reference |
| Alzheimer's Disease | CD33, APOE, BACE, | Brain | (Griciuc et al., 2013) |
| Parkinson's Disease | GDNF, AADC | Brain Neurons | (Christine et al., 2019) |
| X-linked Adrenoleukodystrophy | ABCD1 | Brain/spinal cord Neurons/astrocytes/ microglia/ endothelial cells | (Eichler et al., 2017; Gong et al., 2015) |
| Canavan's | ASPA | Brain | (Leone et al., 2012) |
| Niemann Pick | NPC1 | Brain | (Hughes et al., 2018) |
| Spinal muscular atrophy | SMN | Motor neurons | (Al-Zaidy et al., 2019) |
| Huntington' Disease | HTT | Brain neurons | (Caron et al., 2020; Keskin et al., 2019) |

TABLE 2

| Inner Ear targets (AAV-S) | | | |
|---|---|---|---|
| Disease | Target genes | Target cells/tissues | Reference |
| Connexin-26 | GJB2 | Inner ear - cochlea Fibrocytes/supporting cells | ARO 2020 |
| Usher Type 3A* | CLRN1 | Inner ear - cochlea Hair cells (inner and outer) | (György et al., 2019) |
| Usher Type 2D* | WHLN | Inner ear - cochlea Hair cells (inner and outer) | (Isgrig et al., 2017) |
| Hair cell-related hearing loss | ATOH1 | Inner ear - cochlea Supporting cells (for HC regeneration) | (Tan et al., 2019) |
| Hair cell-related hearing loss (DFNB7/11) | TMC1 | Inner ear - cochlea Hair cells (inner and outer) | (Nist-Lund et al., 2019) |
| Inner hair cell-related hearing loss (DFNB9) | OTOF | Inner ear - cochlea Inner hair cells | (Akil et al., 2019) |
| Usher Type 1F* | PCDH15 | Inner ear - cochlea Hair cells (inner and outer) | Reviewed in (Zhang et al., 2018) |
| Usher Type 1B* | Myo7a | Inner ear - cochlea Hair cells (inner and outer) | Reviewied in (Lopes and Williams, 2015) |

*Usher syndrome results in both deafness as above, and in blindness via retinitis pigmentosa

TABLE 3

| Peripheral targets (AAV-F, AAV-S) | | | |
|---|---|---|---|
| Disease | Target genes | Target cells/tissues | Reference |
| Retinitis pigmentosa (RP; non-syndromic) | RHO, RPGR, RP2, NRL others | Retina (photoreceptors) | (Cehajic-Kapetanovic et al., 2020; Millington-Ward et al., 2011; Mookherjee et al., 2015; Yu et al., 2017) |
| Leber congenital amaurosis | RPE65 | Retina (retinal pigment epithelium) | (Maguire et al., 2019) |
| Leber Hereditary Optic Neuropathy | ND1-6 mito-chondrial | Retina (retinal ganglion cells) | (Wan et al., 2016; Yang et al., 2016) |
| Usher Syndrome (RP; syndromic with deafness) | Usher genes listed above | Retina (photoreceptors) | As above |
| Duchenne Muscular Dystrophy | Dystro-phin | Muscle | Reviewed in (Duan, 2018) |
| Allograft vasculopathy | TIMP-1 | Heart | (Remes et al., 2020) |
| Hemophilia A and B | FVIII, FIX | Liver | Reviewed in (Nathwani, 2019) |

Pharmaceutical Compositions and Methods of Administration

The methods described herein include the use of pharmaceutical compositions comprising the AAVs as an active ingredient.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration.

Pharmaceutical compositions are typically formulated to be compatible with its intended route of administration. Examples of routes of administration include parenteral, e.g., intravenous, intraarterial, subcutaneous, intraperitoneal, intrathecal, intramuscular, or injection or infusion administration. Delivery can thus be systemic or localized. For example, for delivery into the inner ear, delivery into the cochlea through application over or through the round window membrane, through a surgically drilled cochleostomy adjacent to the round window, a fenestra in the bony oval window, or a semicircular canal can be used (see, e.g., Kim et al., Mol Ther Methods Clin Dev. 2019 Jan. 11; 13:197-204; Ren et al., Front Cell Neurosci. 2019; 13: 323); for delivery into the retina, subretinal or intravitreal injections can be used (see, e.g., Ochakovski et al., Front Neurosci. 2017; 11: 174; Xue et al., Eye (Lond). 2017 September; 31(9):1308-1316).

Methods of formulating suitable pharmaceutical compositions are known in the art, see, e.g., *Remington: The Science and Practice of Pharmacy,* 21st ed., 2005; and the books in the series *Drugs and the Pharmaceutical Sciences: a Series of Textbooks and Monographs* (Dekker, N.Y.). For example, solutions or suspensions used for parenteral application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, NJ) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

The pharmaceutical compositions can be included in a kit, container, pack, or dispenser together with instructions for administration. For example, the kit can include compositions comprising an AAV comprising a peptide as described herein.

EXAMPLES

The invention is further described in the following examples, which do not limit the scope of the invention described in the claims.

Materials and Methods

The following materials and methods were used in the Examples below, unless otherwise noted.

AAV Library Construction.

iTransduce Plasmid: pAAV-CBA-Cre-$^{mut}$-p41-Cap9del

We constructed the iTransduce library backbone plasmid called pAAV-CBA-Cre$^{mut}$-p41-Cap9del, containing two expression cassettes in-cis: 1) the CBA-Cre$^{mut}$ in which we introduced a mutant Cre cDNA (CCG→CCT encoding the Pro15 amino acid to eliminate the AgeI site initially present) under the ubiquitous promoter CBA, 2) the p41-Cap9del composed of the AAV9 capsid gene under the AAV5 p41 promoter (residues 1680-1974 of GenBank AF085716.1) and splicing sequences of the AAV2 rep gene (similar as described in[12]).

Both the mutant Cre cDNA (Cre$^{mut}$) flanked by KpnI and SalI restriction sites and the p41-CAP9(del)-polyA fragment were synthesized by GenScript and cloned into a puC57 backbone. We constructed first the pAAV-CBA-Cre$^{mut}$-polyA plasmid by subcloning the mutant Cre cDNA (fragment KpnI-blunt, SalI) in place of eGFP-WPRE in our pAAV-CBA-WPRE backbone (opened with NcoI-blunt/SalI, which eliminated the eGFP-WPRE fragment initially present). We then introduced the p41-Cap9del fragment harbouring a K449R mutation in the Cap9 sequence allowing the creation of a unique XbaI site, and in which the 447 bp Cap sequence between XbaI and AgeI restriction sites had been deleted.

Plasmid for Generating Random 7-Mer Peptide Cap Fragments and Subcloning the CAP9 Fragments Retrieved by PCR: pUC57-Cap9-XbaI/KpnI/AgeI.

We first had the 447 bp region of the AAV9 capsid sequence between the XbaI/AgeI sites (sequence that is missing in pAAV-CBA-Cre$^{mut}$-p41-Cap9del) synthesized by Genscript (Piscataway, NJ) and subcloned into a pUC57-Kan plasmid. This capsid sequence contains the same removal of the EarI site in this 447 bp region WT AAV9 cap that allows restriction digest removal of WT AAV9 as described by Deverman et al. 2015. This also creates a unique KpnI site. The cap fragment of pUC57-Cap9-XbaI/KpnI/AgeI was used to generate the initial library of random 21-mer nucleotide sequences (encoding for 7-mer peptides) inserted between nucleotides encoding amino acids 588 and 589 of AAV9 VP1. We used a strategy similar to that of Deverman et al. (2015). Briefly, pUC57-Cap9-XbaI/KpnI/AgeI served as template to amplify the cap DNA and insert random 21-mer sequences using a forward and reverse primer. Primer information: XF-extend (5'GTACTATCTCTCTAGAACtattaacggttc3'; SEQ ID NO: 11) and reverse primer 588iRev 5' (GTATTCCTTGGTTTTGAA CCCAACCGGTCTGCGCCTGTGCXMNNMNNMNNM NNMNNMNNMNNTTGGGCACTCTGGTGGTTTGTG 3'; SEQ ID NO: 12) in which the MNN repeat refers to the the randomized 21-mer nucleotides (purchased from IDT). XF-extend and 588iRev were used in a PCR with Phusion polymerase (NEB) and pUC57-Cap9-XbaI/KpnI/AgeI as template. The 447 bp PCR product was digested with XbaI and AgeI overnight at 37° C. and then gel-purified the product (Qiagen). Similarly, pAAV-CBA-Cre-$^{mut}$p41-Cap9del was digested with XbaI and AgeI and gel purified. Next, a ligation reaction (1 h at room temperature) with T4 DNA ligase (NEB) was performed using a 3:1 cap insert to vector molar ratio. The subsequent ligated plasmid was called pAA V-CBA-Cre-$^{mut}$-p41-Cap9-7mer and contained a pool of plasmids with random 7-mer peptides inserted in the cap gene between nucleotides encoding 588 and 589 of AAV9 VP1.

This plasmid (pUC57-Cap9-XbaI/KpnI/AgeI) was also used as our recipient plasmid for subcloning the CAP9 fragments amplified by PCR from brain tissue. We removed an upstream KpnI site in the pUC57 plasmid by digestion with SacI and NsiI and ligation. This allowed the KpnI site in the capsid fragment to be unique. See below in Rep expression plasmid.

We constructed a rep expression plasmid called pAR9-Cap9-stop/AAP/Rep using a similar strategy to that as Deverman et al.[12]. The entire cDNA was synthesized by Genscript and cloned into a pUC57-Kan plasmid. Stop codons were inserted in place of start codons for VP1, VP2, VP3 so that no parental AAV9 capsids were produced, while maintaining AAP and rep expression.

AAV Library Production and Purification.

For each production, we plated 15-cm tissue culture dishes with $1.5\times10^7$ 293T cells/dish. The next day cells were transfected using the calcium phosphate method, with the adenovirus helper plasmid (pAdΔF6, 26 μg per plate), rep plasmid (pAR9-Cap9-stop/AAP/Rep, 12 μg per plate) and ITR-flanked AAV library (pAAV-CBA-Cre-mut/p41-Cap9-7mer, 1 μg per plate) to induce production of AAV. The day after transfection, medium was changed to DMEM containing 2% FBS. AAV was purified from the cell lysate using iodixanol density-gradient ultracentrifugation. Buffer exchange to PBS was done using ZEBA spin columns (7K MWCO; Thermo Fisher Scientific) and further concentration was performed using Amicon Ultra 100 kDa MWCO ultrafiltration centrifugal devices (Millipore). Vectors were stored at −80° C. until use. We quantified AAV genomic copies (vg) in AAV preparations using TaqMan qPCR with ITR-sequence specific primers and probes[20, 21].

Next Generation Sequencing of Library.

Next generation sequencing was performed on the plasmid AAV9 library pool, as well as following packaging of capsids. Sequencing was also performed following PCR rescue of the cap fragment (either from brain tissue or from isolated tdTomato-positive cells sorted by flow cytometry). For each round of selection viral DNA corresponding to the insert-containing region was amplified by PCR using the Phusion High-Fidelity PCR kit from New England Biolabs (Forward primer: 5'-AATCCTGGACCTGCTATGGC-3' (SEQ ID NO:13), reverse primer: 5'-TGCCAAACCATACCCGGAAG-3' (SEQ ID NO:14)). PCR amplification was performed using Q5 polymerase (New England Biolabs). Unique barcode adapters were annealed to each sample, and samples were sequenced on an Illumina Miseq (150 bp reads). Approximately 50-100,000 reads per sample were analysed. Sequence output files were quality-checked initially using FastQC (bioinformatics.babraham.ac.uk/projects/fastqc/), and analyzed on a program custom-written in Python. Briefly, sequences were binned based on the presence or absence of insert; insert-containing sequences were then compared to a baseline reference sequence and error-free reads were tabulated based on incidences of each detected unique insert. Inserts were translated and normalized.

Animals.

All animal experiments were approved by the Massachusetts General Hospital Subcommittee on Research Animal Care following guidelines set forth by the National Institutes of Health Guide for the Care and Use of Laboratory Animals. We used adult age (8-10 week old) Ai9 (strain #007909), C57BL/6 (strain #000664), and BALB/c (strain #000651) mice all from The Jackson Laboratory, Bar Harbor, ME All animals were euthanized three weeks post-injection, perfused transcardially and tissues were harvested and either fixed in 4% paraformaldehyde in PBS, snap frozen in liquid nitrogen or dissociated for flow cytometry.

In Vivo Selection of Brain-Tropic Capsids.

Ai9 mice were injected intravenously (tail vein) with the dose in vg indicated in the results section and 3 weeks post injection, mice were euthanized, and tissue harvested.

Mice were deeply anesthetized by isofluorane and decapitated. For round 1, the brain was rapidly dissected and two coronal sections (2 mm thick) were harvested. One section was used for extracting whole brain DNA (DNeasy Blood and Tissue Kits, Qiagen, Hilden, Germany). The other coronal section was fixed in 4% PFA and paraffin embedded for immunohistology (tdtomato-positive cells were detected after each round of selection by DAB staining using a rabbit anti-RFP antibody from Rockland Immunochemicals). For round 2, brain tissue was then cut with a razor blade into 1 mm3 pieces and neural cells were isolated by papain dissociation (Papain Dissociation System, Worthington), according to the manufacturer's instructions. Following dissociation, myelin was removed (Myelin Removal Beads II, human, mouse, rat from Miltenyi) and the Td-tomato positive cells were sorted by a S3e™ Cell Sorter (Bio-Rad). Cells were sorted by first setting gates to exclude cellular debris and select for singlets only. Cell suspensions from an AAV9-PHP.B-Cre injected Ai9 (positive control) and a PBS injected Ai9 mouse (negative control) were used to set gates to sort tdTomato-positive and negative cells. After sorting, the tdTomato-positive cells were immediately pelleted by centrifugation, and DNA was extracted using the ARCTURUS PicoPure DNA extraction kit (ThermoFisher).

After DNA extraction, the Cap9 inserts (containing the 21-mer sequence encoding the 7mer peptides) were amplified using the following primers: Cap9_Kpn/Age_For: 5'-AGCTACCGACAACAACGTGT-3' (SEQ ID NO:15) and Cap9_Kpn/Age_Rev: 5'-AGAAGGGTGAAAGTTGCCGT-3' (SEQ ID NO:16) (Phusion High-Fidelity PCR kit, New England Biolabs). The amplicons were then purified (Monarch PCR & DNA Cleanup kit, New England Biolabs), digested by KpnI, AgeI and BanII and the Cap9 KpnI-AgeI fragments (144 bp) were agarose gel purified (Monarch DNA Gel Extraction kit, New England Biolabs) before ligation in the pUC57-Cap9-XbaI/AgeI/KpnI plasmid (opened with KpnI and AgeI and dephosphorylated with Calf Inositol Phosphatase, New England Biolabs). The ligation products were transformed into electrocompetent DHS-alpha bacteria (New England Biolabs) and the entire transformation was grown overnight in LB-ampicillin medium. pUC57-Cap9-XbaI/AgeI/KpnI plasmid was purified by maxi prep (Qiagen). Plasmid was digested by XbaI/AgeI to release the 447 bp cap fragment which was gel purified and ligated with similarly cut pAAV-CBA-Cre-mut/p41-Cap9del for the next round of AAV library production.

AAV Rep Cap Plasmids Containing AAV-F and AAV-S Peptide Inserts for Vector Production.

To create rep cap plasmids encoding AAV9 capsids displaying the peptide insert of interest for production of vectors encoding a transgene of interest (e.g. GFP), we digested an AAV9 rep cap plasmid with BsiWI and BaeI which removes a fragment flanking the VP3 amino acid 588 site for peptide sequence insertion. Next we ordered a 997 bp dsDNA fragment from Integrated DNA Technologies (IDT, Coralville, IA), which contains overlapping Gibson homology arms with the BsiWI/BaeI cut AAV9 as well as the 21-mer nucleotide sequence encoding the peptide of interest in frame after amino acid 588 of VP3. Last, we performed Gibson assembly using the Gibson Assembly® Master Mix (NEB, Ipswich, MA) to ligate the peptide containing insert into the AAV9 rep cap plasmid.

AAV Vectors for Transduction Analysis.

For each production, we plated 15-cm tissue culture dishes with $1.5\times10^7$ 293T cells/dish. The next day cells were transfected using the calcium phosphate method, with the adenovirus helper plasmid (pAdΔF6, 26 μg per plate), rep/cap plasmid (AAV9, AAV-F, AAV-S; 12 μg per plate) and ITR-flanked transgene cassette plasmid (single-stranded AAV-CBA-GFP-WPRE[22], 10 μg/plate) to induce production of AAV. The day after transfection, medium was changed to DMEM containing 2% FBS. AAV was purified from the cell lysate using iodixanol density-gradient ultracentrifugation. Buffer exchange to PBS was done using ZEBA spin columns (7K MWCO; Thermo Fisher Scientific) and further concentration was performed using Amicon Ultra 100 kDa MWCO ultrafiltration centrifugal devices (Millipore). Vectors were stored at −80° C. until use. We quantified AAV genomic copies in AAV preparations using TaqMan qPCR with BGH polyA-sequence specific primers and probe[23].

Animal Euthanasia and Tissue Harvesting

Mice (strain indicated in each FIGure) were slowly injected via the lateral tail vein with 200 μl of the tested AAV vector diluted in sterile PBS (low dose: $4\times10^{12}$ vg/kg and high dose: $3.2\times10^{13}$ vg/kg), before gently finger-clamping the injection site until bleeding stopped. Three weeks post injection mice were euthanized and perfused transcardially with sterile cold phosphate buffered saline (PBS). Next the brain was longitudinally bisected into two hemispheres. One hemisphere was post-fixed in 15% Glycerol/4% paraformaldehyde diluted in PBS for 48 hours, followed by 30% glycerol for cryopreservation for another 48-72 hours. For the high-dose cohort, a small piece of heart, muscle (gastrocnemius) and the retina were also processed for immunohistology. We made 3 independent preparations of AAV-S, AAV-F, and AAV9 (Table I). The transduction results in mice were from one preparation of each vector, however we have replicated these results in two more independent experiments.

Immunohistology and High-Magnification Imaging of AAV-CBA-GFP Transduced Neural and Neuronal Cell Populations Coronal floating sections (40 μm) were cut using a cryostat microtome. After rinsing off the glycerol in tris-buffered saline (TBS) buffer, cryosections were permeabilized with 0.5% Triton X-100 (AmericanBio) in TBS for 30 minutes at room temperature and blocked with 5% normal goat serum (or normal donkey serum) and 0.05% Triton in TBS for 1 hour at room temperature. Primary antibodies were incubated overnight at 4° C. in 2.5% NGS and 0.05% Triton in TBS, while Alexa Fluor 488 or -Cy3 conjugated secondary antibodies (Jackson ImmunoResearch laboratories, Baltimore, USA) were incubated for 1 hour the next day. Primary antibodies used for this study were: chicken anti-GFP (Aves Labs, Tigard, USA), Mouse anti-NeuN (EMD Millipore, Burlington, USA); rabbit anti-Glutamine Synthetase (Abcam, Cambridge, USA); rabbit anti-Olig2 (EMD Millipore, Burlington, USA); rabbit anti-Iba1 (Wako, Japan); rabbit anti-CamKII (Abcam, Cambridge, USA); mouse anti-GAD67 (EMD Millipore, Burlington, USA); rabbit anti-ChAT (EMD Millipore, Burlington, USA); mouse anti-calbindin (Abcam, Cambridge, USA) and rabbit anti-TH (Novus Biologicals, Littleton, USA). Sections were mounted with Vectashield mounting medium with DAPI (Vector Laboratories, Burlingame, USA).

To identify the neural cell types transduced by each vector and investigate the various neuronal sub-types targeted by AAV-F, a Zeiss Axio Imager Z epifluorescence microscope equipped with AxioVision software and a 60× objective was used to take high-resolution images showing colocalization between GFP and each cell marker.

Imaging and Quantification of Global GFP Signal Coverage

To quantify the overall native GFP fluorescence signal in brain and liver section, a robotic slide scanner Virtual slide microscope VS120 (Olympus) was used to image the entire batch of slides on one go using an Olympus UPLSAPO 10× objective. In order to reduce variability, the entire batch of slides was imaged in one session. The initial exposure time for GFP was set up so that the fluorescent signal was neither under-no over-saturated across all experimental group and remained unchanged throughout the entire batch scan. The order of the slides was randomized and remained blinded until final statistical analysis. The Olympus cellSens Standard software was then used to analyze the percent GFP coverage in each brain section. A region of interest (ROI) was initially defined using the "ROI-polygon" tool and we quantified the GFP-positive area within this initial ROI, after applying a similar detection threshold on the GFP channel for all the slides analyzed (the threshold was set at a similar level for the analysis of all mouse brain sections, but a different threshold was applied for the analysis of all mouse liver sections and all rat brain sections). The percentage of GFP-positive area accordingly to the total surface of the ROI was then calculated. The autofluorescence signal was taken into account in our analysis as we set the threshold for eGFP fluorescence intensity above the autofluorescence level (making sure that only the signal from AAV-GFP transduced cells was taken into account). In addition, we drew each ROI for each brain section avoiding the very edges of the section, as those could also present with a high level of autofluorescence. The ventricular space was also excluded from our analysis. Finally, three technical replicates (brain sections) were measured per mouse and all measurements were done blind until the final step of the analysis.

Stereology-Based Quantitative Analyses of the Percentages of Transduced Astrocytes and Neurons Stereology-based studies were performed as previously described[24, 25], after co-staining the brain sections for GFP and NeuN (neuronal marker) or GFP and GS (Glutamine synthetase, pan-astrocytic marker). We did not include microglia and oligodendrocytes in this analysis as those cell types were not transduced to an appreciable amount. Stereological evaluation of the percentages of AAV-transduced neurons and astrocytes was done blindly after de-identification of the vector initially injected, using a motorized stage of an Olympus BX51 epifluorescence microscope equipped with a DP70 digital CCD camera, an X-Cite fluorescent lamp, and the associated CAST stereology software version 2.3.1.5 (Olympus, Tokyo, Japan). The cortex was initially outlined under the 4× objective. Random sampling of the selected area was defined using the optical dissector probe of the CAST software. To evaluate the percentage of AAV9, AAV9-PHP.B, AAV-S and AAV-F transduced astrocytes or neurons, the stereology-based counts were performed under the 20× objective, with a meander sampling of 10% for the surface of cortex for the "high transduction" AAVs, and 20% for "low transduction" AAVs (considering the infrequency of GFP positive cells in those cases). For each counting frame, the total number of astrocytes (GS positive cells) or neurons (NeuN positive cells) were evaluated, and, among each of those populations, the percentages of GFP positive cells. Only glial and neuronal cells with DAPI-positive nucleus within the counting frame were considered.

Vector Genome Quantification in the Brain and Liver

One brain hemisphere and a small piece of liver were fresh frozen for AAV genome isolation for vector genome biodistribution. For the fresh frozen brain and liver samples, we isolated genomic and AAV vector DNA from 10 mg of tissue using the DNeasy Blood and Tissue Kit (Qiagen) according to manufacturer's instructions. DNA was quantitated using a NanoDrop ND-1000 Spectrophotometer (Thermo Scientific). Next using 50 ng of genomic DNA as template, we performed a Tagman qPCR using probe and primers to the polyA region of the transgene expression cassette (same assay used to titer the purified AAV vectors). To ensure equal genomic DNA input for each sample, we performed a separate qPCR on each sample using a Tagman probe and primer set that detects GAPDH genomic DNA (Thermo Fisher Scientific, Assay ID Mm01180221_g1; gene symbol Gm12070). For each organ/tissue, we adjusted the AAV vector genome copies for each sample by taking into account any differences in GAPDH Ct values using the following formula: (AAV vector genome copies)/($2^{\Delta Ct}$). The ΔCt value was calculated by the following formula: GAPDH Ct value of sample of interest–average GAPDH Ct value of sample which had the lowest amount of GAPDH (highest Ct value). Data was expressed as AAV vector genomes per 50 ng genomic DNA.

Human Neuron Transduction:

Primary human fetal neural stem cells (NSCs) were obtained from the Birth Defects Research Laboratory (University of Washington, Seattle, WA) in full compliance with the NIH ethical guidelines. The isolation procedure has been detailed previously[26] with slight modifications. Briefly, brain tissue was incubated in 0.25% trypsin, DNase (90 Units/mL), diluted in Hank's balanced salt solution (HBSS) for 45 min. Tissue was titrated, transferred into 4° C. heat-inactivated fetal bovine serum and centrifuged at 500 g for 20 min. The pellet was resuspended in NSC complete media consisting of x-Vivo 15 (without phenol red and gentamicin; Lonza) supplemented with 10 μg of basic fibroblast growth factor (Life Technologies), 100 μg of epidermal growth factor (Life Technologies), 5 μg of leukemia inhibitory factor (EMD Millipore), 60 ng/mL of N-acetylcysteine (Sigma-Aldrich), 4 mL of neural survival factor-1 supplement (Lonza), 5 mL of 100× N-2 supplement (Life Technologies), 100 U of penicillin, 100 μg/mL of streptomycin (Life Technologies), and 2.5 μg/mL of fungizone (Life Technologies). Supernatants were then filtered through a 40 μm cell strainer (Corning Life Science). Neurospheres larger than 40 m in diameter were dissociated with Accutase (10 min). Neural Differentiation Medium consisted of 1× Neurobasal Medium, 2% B-27 serum-free supplement, and 2 mM GlutaMAX-I supplement (all from Invitrogen) and supplemented with human recombinant brain-derived neurotrophic factor (BDNF) (10 ng/mL; Peprotech).

Differentiating NSCs were grown in chamber slides in differentiation media for 2 weeks and then treated with the indicated AAV vector encoding GFP ($7\times10^{9}$ $^{vg}$/well added, 150 vg/cell). One week after transduction, cells were fixed with 4% paraformaldehyde and permeabilized with 0.05% Triton X-100 (Sigma-Aldrich) in 1× phosphate-buffered saline (PBS; Invitrogen). Cells were stained with a primary monoclonal antibody (TU-20) to neuron-specific class III β-Tubulin (1:50; Abcam). Secondary antibodies conjugated to Alexa Fluor 594 (diluted 1:200; Invitrogen) were added for 1 h, followed by DAPI for 30 min. The slides were then mounted with a ProLong antifade reagent (Invitrogen). Max projection Images were generated form captured Z-stacks using the Nikon AiR confocal microscope.

Z-stacks were loaded in Imaris, the surface module was used to render the images into 3D volumes. GFP+ neurons were counted (under channel 1-green) and Class III β-Tubulin positive neurons (under channel 2-red). Using Imaris' colocalization module, the population of neurons double positive for the above was determined.

Statistics

Statistical analysis of data was performed using GraphPad Prism software (version 8.00). A one-way ANOVA test followed by a Tukey's multiple comparisons test was performed, across the different groups AAV9, AAV9-PHP.B, AAV-S and AAV-F. A value of $p<0.05$ was considered to be statistically significant. Results are shown as the mean±S.E.M. Similar analyses were performed the biodistribution assay of AAV genomes in brain and liver, as well as transduction of human neurons.

Direct Stereotactic Injection of Vectors

Adult C57BL/6 mice were anesthetized by intraperitoneal injection of ketamine/xylazine (100 mg/kg and 50 mg/kg body weight, respectively) and positioned on a stereotactic frame (Kopf Instruments, Tujunga, USA). Injections of vectors were performed in the cortex (somatosensory cortex) and the hippocampus. A total of 3 μl of viral suspension was injected ($1.65\times10^{10}$ and $5.6\times10^{10}$ gc per injection site for AAV-F and AAV-S, respectively) at a rate of 0.15 μl/minute)

and using a 33-gauge sharp needle attached to a 10-μl Hamilton syringe (Sigma-Aldrich, St. Louis, USA). Stereotactic coordinates of injection sites were calculated from bregma (Cortex coordinates: anteroposterior −1 mm, mediolateral±1 mm and dorsoventral −0.8 mm; Hippocampus coordinates: anteroposterior −2 mm, mediolateral±1.7 mm and dorsoventral −2.5 mm).

Intrathecal Bolus Delivery (IT Bolus)

Adult C57BL/6 mice were put under anesthesia by isoflurane. After the skin over the lumbar region was shaved and cleaned, a 3~4 cm mid-sagittal incision was made through the skin exposing the muscle and spine. A catheter was inserted between L4-L5 spine region and attached to a gas-tight Hamilton syringe with a 33-gauge steel needle. Ten microliters of AAV9-CBA-GFP ($1.25\times10^{11}$ vg) vectors or AAV-F-CBA-GFP ($8.8\times10^{10}$ vg) were slowly injected at a rate of 2 μl/min. Mice were killed three weeks post injection.

For low magnification imaging of whole spinal cord and brain sections, we stained overnight with anti-GFP (Invitrogen, cat no. G10362, dilution 1:250) followed by secondary antibody staining and imaging as for FIG. 3.

For immunostaining of cell types in brain and spinal cord, fixed tissue sections were washed with PBS, blocked with goat serum and permeabilized with 0.3% Triton in PBS. Target antibodies were diluted in blocking buffer and incubated at 4° C. overnight.

Primary antibodies: anti-GFP: catalog no. ab1218 (abcam): Dilution, 1:1000

GFAP: catalog no catz0334, (Dako); Dilution, 1:500

NeuN: catalog no ab177487, (abcam); Dilution, 1:300

After overnight incubation slides were washed extensively with PBS with 0.1% Tween. Fluorochrome-conjugated secondary antibodies (1:500 dilution) were added and incubated for 1 h at RT. After washing slides were washed with PBS and mounted using DAPI mounting solution (ThermoFisher, cat no. P36931). Slides were imaged using a Zeiss LSM 800 confocal laser scanning microscope.

Transmission Electron Microscopy

Carbon-coated grids (Electron Microscopy Sciences, EMS) was rendered hydrophilic by exposure to a 25 mA glow discharge for 20 s. For each AAV vector pre, 5 μl was adsorbed onto a grid for 1 minute, and stained with 1% uranyl acetate (EMS #22400) for 20s. Grids were examined in a Tecnai$G^2$ Spirit BioTWIN and imaged with an AMT 2k CCD camera. Work was carried out at the Harvard Medical School Electron Microscopy Facility. Counts were performed as follows: 5 representative images of each vector prep were taken; all full and empty capsids were counted using the Count tool in Photoshop (CS6). Empty capsid percentage was calculated for each image, and plotted.

Example 1. Design of iTransduce—an Expression-Based AAV Library

First, we constructed an AAV library plasmid which consisted of an AAV2 ITR-flanked expression cassette comprised of a chicken beta actin (CBA)-driven Cre recombinase and a p41promoter-driven AAV9 capsid (schematic in FIG. 1*a*). Pseudorandom 21-base nucleotides were inserted between AAV9 VP1 nucleotides encoding amino acids 588/589 via PCR. Before viral packaging, we sequenced this plasmid library using low-depth next-generation sequencing (NGS) and confirmed the presence of 21-mer inserts in the vast majority of plasmids and the lack of variant bias (data not shown). We then packaged the capsid library and performed NGS to validate that the vector creation process maintained a sufficient diversity for selection. iTransduce relies on each unique capsid carrying both its own cap gene as well as a Cre-expressing construct (FIG. 1*b*). Transgenic mice (Ai9) carrying a floxed-STOP tdTomato cassette are injected intravenously with the AAV library (FIG. 1*b-i*). Those capsids that successfully transduce cells enable tdTomato expression in any target organ or cell type (without being dependent upon the availability of specific Cre transgenic mouse lines); these tdTomato-positive cells can then be flow sorted from the tissue of interest (optionally, alongside cell-specific markers, FIG. 1*b-ii*). Viral DNA rescued from these cells should correspond to capsid variants that can effectively overcome all of the extracellular and intracellular biological barriers to transgene expression (FIG. 1*b-iii*).

Figure 7A:
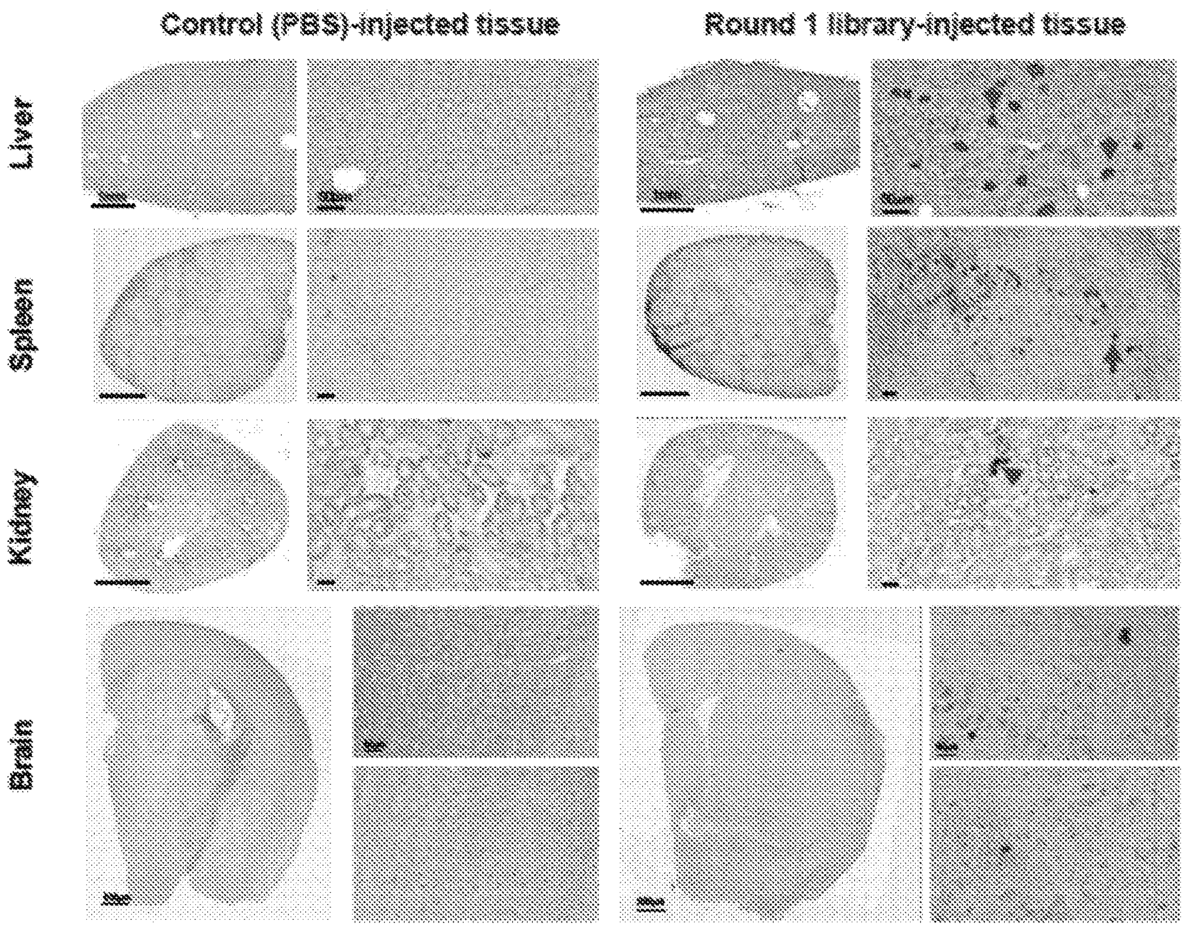
Figure 7B:
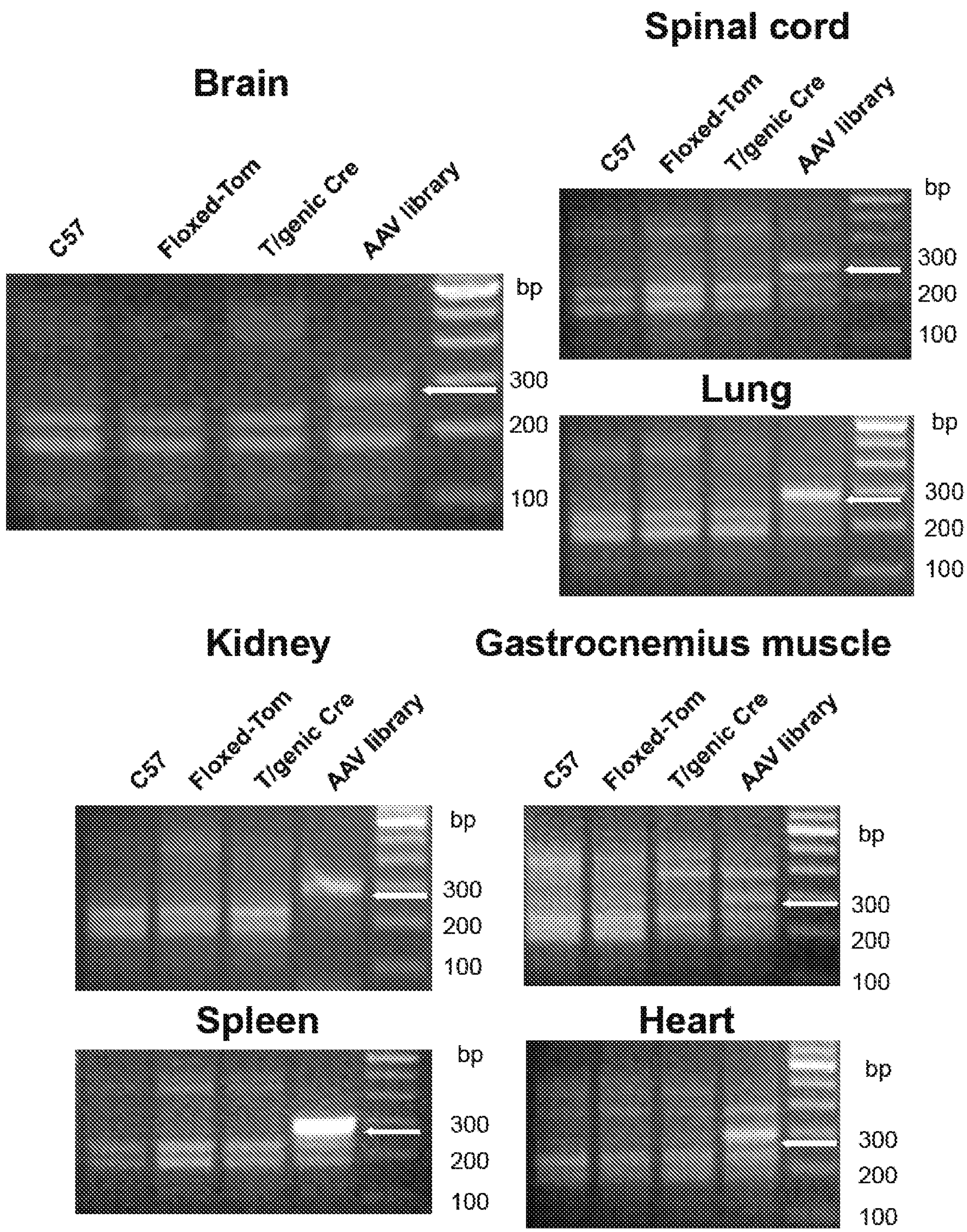

Example 2. Selection of New AAV9 Capsid Variants Using Transgene Expression to Identify Functional Capsids To test the iTransduce library strategy, we performed a proof-of-concept selection to attempt to isolate AAV capsid variants with the ability to transduce brain cells after systemic injection. $1.27\times10^{11}$ vector genomes (vg, $5\times10^{12}$ vg/kg) of the library were injected intravenously through the tail vein of one adult male and one female Ai9 mouse and three weeks post-injection the mice were killed; a section of liver, brain, spleen, and kidney were cut and immunostaining of tdTomato was performed. We readily detected tdTomato positive cells (likely hepatocytes) in the liver, with scattered tdTomato positive cells (both neurons and astrocytes) in the brain as well as the other organs (FIG. 7*a*). We also tested whether we could rescue the cap DNA containing the 21-base insert by PCR, and we detected specific bands in 10 organs/tissues in mice injected with the library, but not in control, non-injected mice (FIG. 7*b*). We pooled the remaining brain tissue from the female and male mice, and DNA was extracted, initially from total brain tissue for the first round of selection. We amplified cap DNA containing the 21-mer insert and analyzed their identity and read counts using NGS. We observed substantial enrichment of specific peptides in the library population harvested from brain tissue following a single round of selection when compared to the unselected library and with the variants retrieved from liver (FIG. 7*c* and data not shown). Next, we isolated the insert-containing region of viral DNA and re-cloned it back into the AAV plasmid backbone and repackaged capsids ("brain-enriched capsid library") for a second round of selection.

Figure 2B:
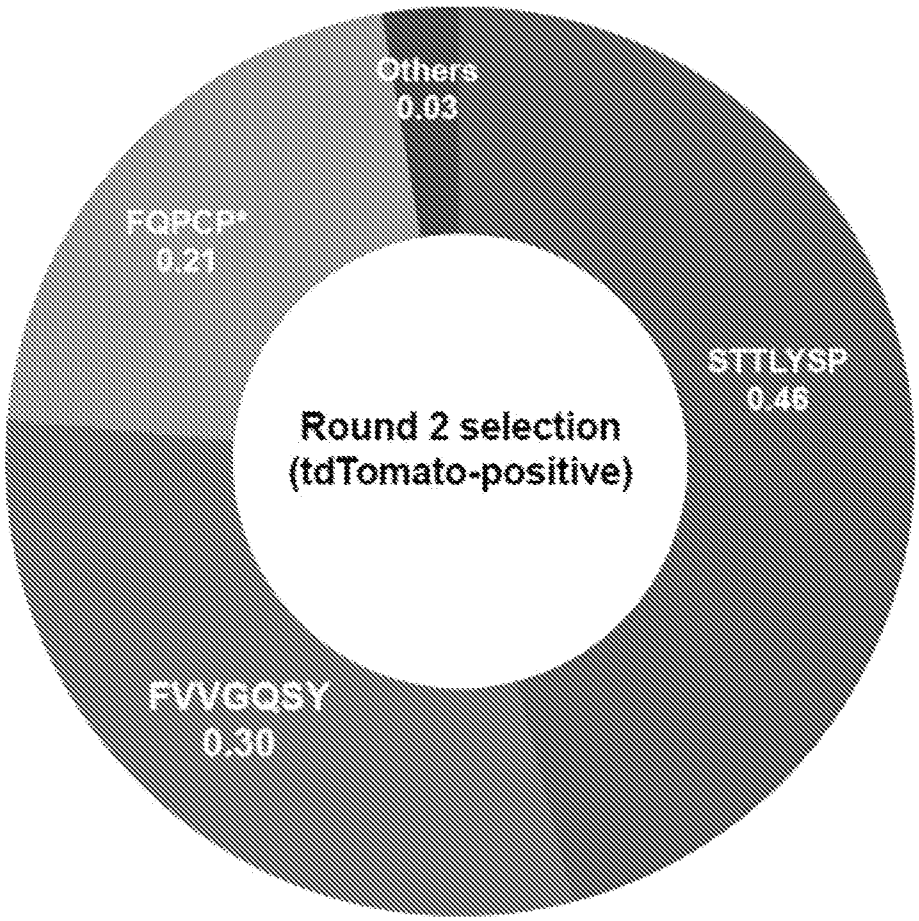

For the second round of selection, two Ai9 mice (one male, one female) were injected with the library rescued from round 1 (dose of $1.91\times10^{10}$ vg, $7.64\times10^{11}$ vg/kg) and sacrificed after three weeks. Prior to injection, sequence containing the variant region was amplified and sequenced by NGS to ensure a pre-existing bias had not been introduced into the vector pool (FIG. 2). The brain tissue was dissociated to obtain a cell suspension for sorting tdTomato-positive cells by flow cytometry. We flow sorted 3,834 tdTomato-positive cells (0.043% of the initial cell suspension), which were indicative of successful transduction (FIG. 8*a-b*). Viral DNA from tdTomato sorted cells was amplified and sequenced as previously done (FIG. 2). Viral DNA isolated from tdTomato-positive cells showed 97% of reads represented by just three peptides, STTLYSP, FVVGQSY, and FQPCP* (where * indicates a stop codon) (FIG. 2*b*). We selected two of these, STTLYSP (termed AAV-S) and FVVGQSY (termed AAV-F), for functional evaluation in vivo (we excluded evaluation of FQPCP* as it was likely a product of cross-packaging). As seen in FIG. 2, both of these sequences were detectable in the round 2 library at low levels (~0.4% of reads for each variant), but were highly enriched in the brain after selection.

Figure 3A:

Example 3. AAV-F Capsid Mediates Efficient Transgene Expression in the Murine CNS To test whether these peptides expressed on the capsid of AAV could mediate efficient transgene expression by an AAV vector, we produced these capsids (AAV-S and AAV-F), packaging a single-stranded CBA promoter-driven GFP expression cassette (FIG. 3*a*). For comparison, we included the parental AAV9 vector and AAV9-PHP.B, the most widely studied AAV9 variant with an 7-mer peptide insertion (TLAVPFK) generated by directed evolution[12]. All vectors produced well and gave slightly lower production efficiencies than AAV9 (Table 4).

TABLE 4

Production efficiency of AAV capsids*

| AAV capsid | Titer (vg/ml) | Production Efficiency (vg/cell) |
|---|---|---|
| AAV9 | $3.20 \times 10^{13}$ ($\pm 2.55 \times 10^{13}$) | $3.06 \times 10^{4}$ ($\pm 1.39 \times 10^{4}$) |
| AAV-F | $5.51 \times 10^{12}$ ($\pm 4.23 \times 10^{12}$) | $9.57 \times 10^{3}$ ($\pm 8.00 \times 10^{3}$) |
| AAV-S | $1.88 \times 10^{13}$ ($1.38 \times 10^{13}$) | $2.09 \times 10^{4}$ ($\pm 5.65 \times 10^{3}$) |

Figure 3E:
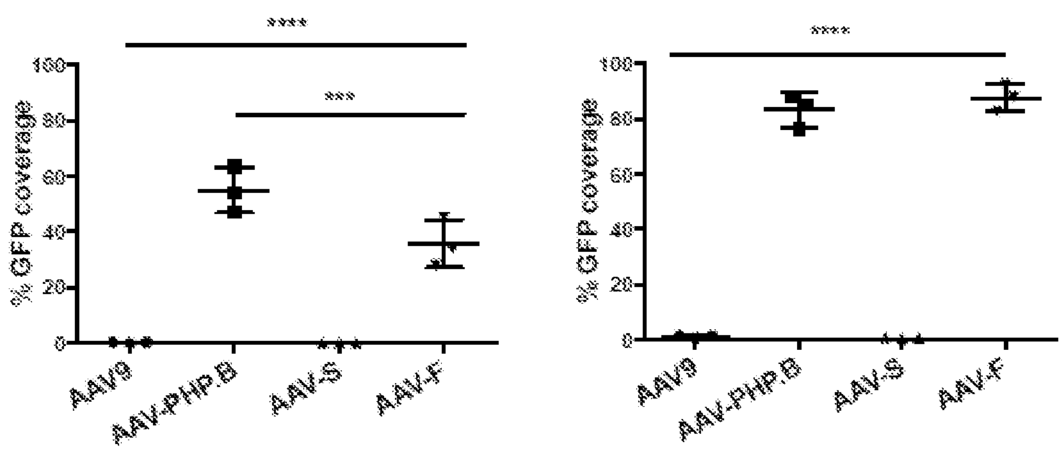
Figure 3F:
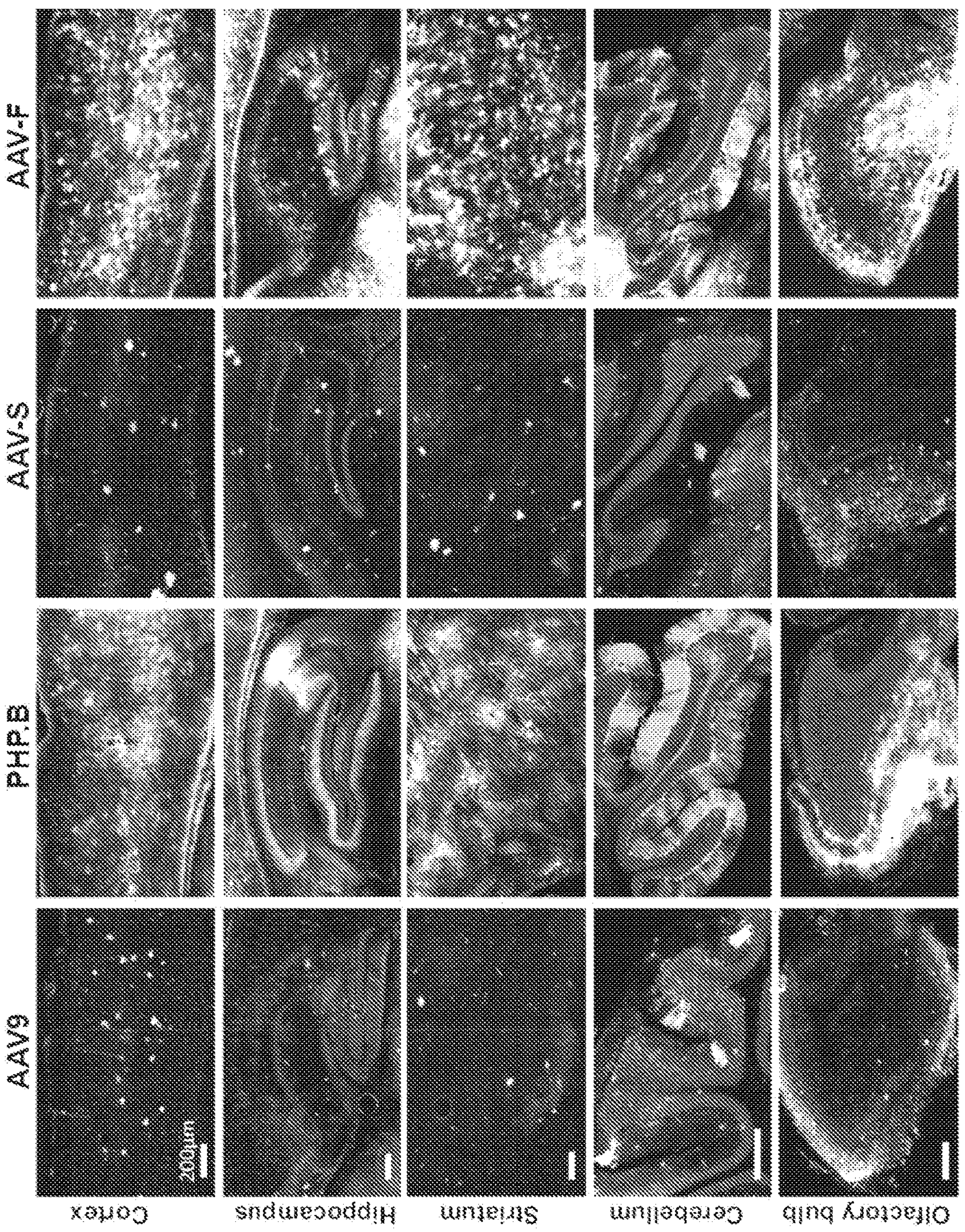

*All capsids packaged a single-stranded AAV2 ITR-flanked AAV-CBA-GFP-WPRE transgene cassette Adult male C57BL/6J mice were injected via the lateral tail vein with a low dose or a high dose ($1\times10^{11}$ vg and $8\times10^{11}$ vg of vector, respectively; approximately $4\times10^{12}$ and $3.2\times10^{13}$ vg/kg) of one of the following vectors: AAV9, AAV9-PHP.B, AAV-S and AAV-F (n=3 each). Three weeks post injection, mice were killed and organs harvested for endogenous (unstained) GFP fluorescence analysis. We quantitated the percent coverage of GFP signal in serial sagittal brain sections (3 sections were analyzed per animal). Remarkably, AAV-F demonstrated a 119-fold ($p<0.0001$) and 68-fold ($p=0.0004$) increased GFP fluorescence coverage compared to the parental AAV9 vector at $1\times10^{11}$ vg and $8\times10^{11}$ vg, respectively (FIG. 3*b, c, e, f*; FIG. 9A-B). AAV9 and AAV-S displayed similar GFP coverage levels (FIG. 3*b, c, e, f*). AAV9-PHP.B gave slightly higher GFP coverage at the low dose compared to AAV-F, while similar levels of GFP coverage was observed at the $8\times10^{11}$ vg dose (FIG. 3*b, c, e, f*). Similar to AAV9-PHP.B, AAV-F transduced the spinal cord with remarkable efficiency (FIG. 3*d*). Most areas of the brain were effectively targeted by AAV-F and robust GFP signal was observed in the cortex, hippocampus, striatum, cerebellum and olfactory bulb (FIG. 3*f*).

Figure 4C:
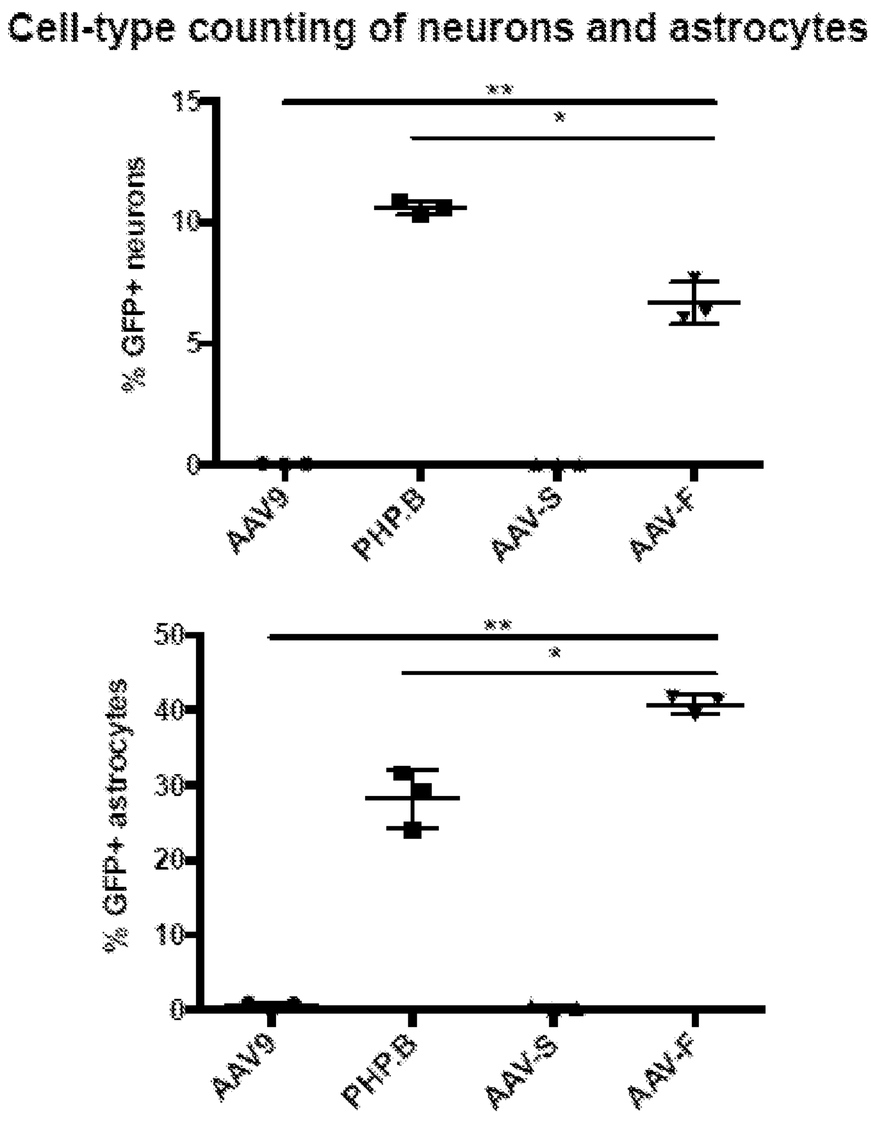

In order to get a detailed appreciation of the cell types being targeted by AAV-S and AAV-F, we next performed a series of co-immunostaining with GFP and markers of neurons (NeuN), astrocytes (Glutamine Synthetase, GS), microglia (Iba-1) and oligodendrocytes (Olig2). AAV-F and AAV-S, similar to the other two reference vectors, mainly transduced neurons and astrocytes (none of the variants appeared to effectively transduce microglial or oligodendroglial cells, FIG. 4*a, b*). Stereological quantitation of neurons and astrocytes in the cortex at the $1\times10^{11}$ vg dose confirmed the efficient transduction potential of AAV-F as compared with conventional AAV9 by a factor of 65 in astrocytes and 171 in neurons, while the difference between AAVS and AAV9 was not significant (the percent of GFP positive astrocytes was 0.63%±0.24% for AAV9 and 0.36±0.15% for AAV-S, respectively; and the percent of GFP positive neurons was 0.039%±0.0.02% for AAV9 and 0.029±0.002% for AAV-S; all ±numbers represent standard error of the mean, SEM). Of note, AAV-F targeted significantly more astrocytes (40.78±0.73%) than AAV9-PHP.B (28.21±0.25%) and the reverse was true for neurons (6.67±0.5% for AAV-F and 10.59±0.16% for AAV9-PHP.B, FIG. 4*c*), suggestive of a slightly different tropism between those two vectors in mice. In addition, AAV-F transduced a variety of neuronal subtypes, including excitatory (CamKII positive) and inhibitory (GAD67 positive) cortical neurons, dopaminergic neurons in the striatum (expressing Tyrosine Hydroxylase, TH), Purkinje neurons in the cerebellum (calbindin positive) and motor neurons in the spinal cord (expressing the Choline acetyltransferase marker, ChAT, FIG. 10*a*.) Consistent with the stereological counts in the cortex (FIG. 4*c*) and with the images of the high dose of AAV-F vs AAV9 (FIG. 3*f*), we observed efficient transduction of neurons and astrocytes with AAV-F and not AAV9 at the dose of $1\times10^{11}$ vg/mouse in the striatum, hippocampus, and cerrebellum (FIG. 10*b*).

Figure 4D:
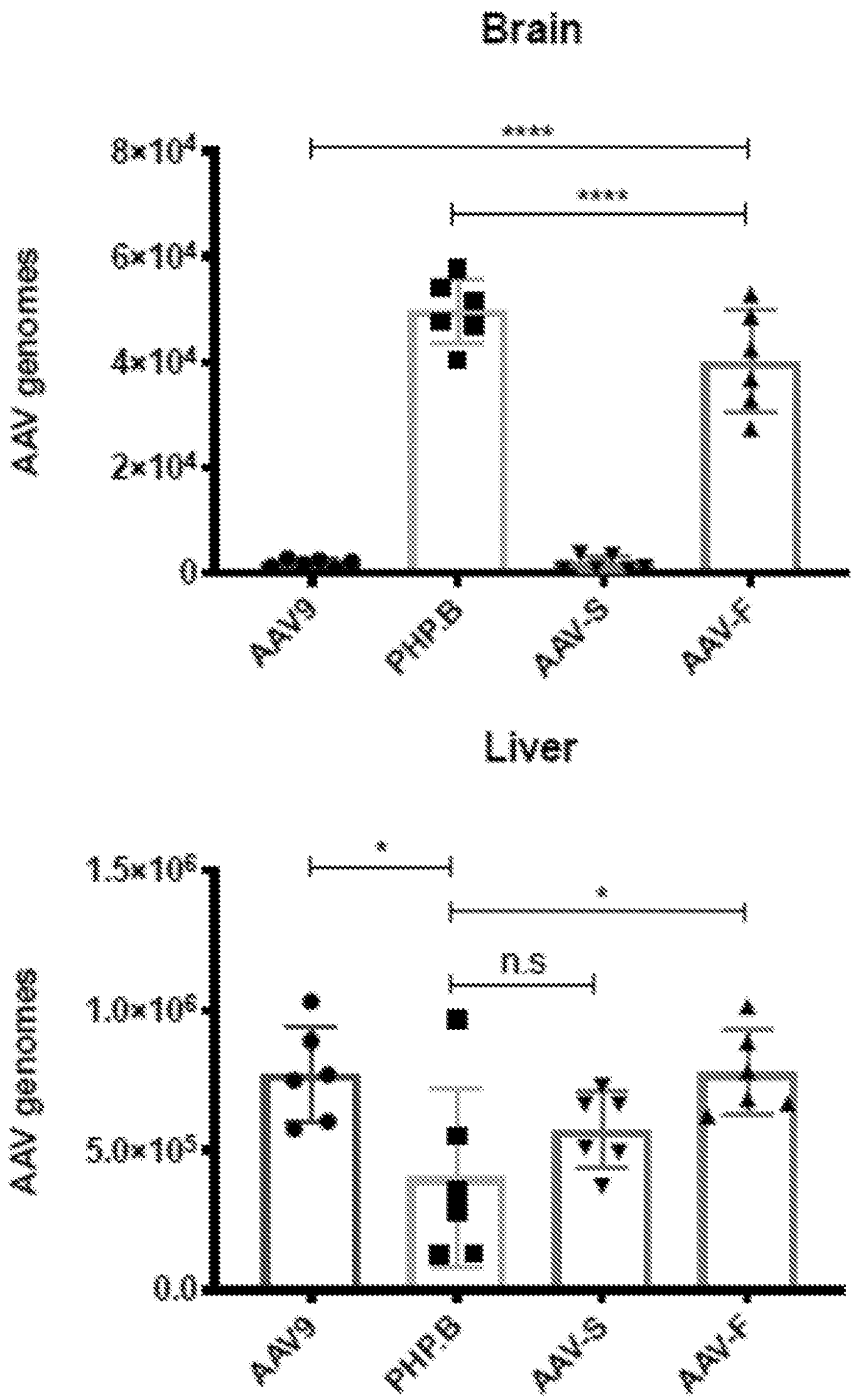

To better understand whether the high levels of GFP transgene expression in the brain with AAV-F corresponded to higher levels of AAV genomes in the brain, we isolated vector and murine genomic DNA from liver and brain and performed a qPCR on the $8\times10^{11}$ vg dosed mice. AAV-F displayed a 20-fold enhancement ($p<0.0001$) in AAV genomes in the brain compared to AAV9 (FIG. 4*d*). As reported, AAV9-PHP.B had a much higher (25-fold) amount of AAV genomes in the brain compared to AAV9, while AAV-S had a low level, similar to the GFP fluorescence data (FIG. 3). PHP.B showed expression levels in the liver that were slightly lower than AAV9 and AAV-F (although not AAV-S; FIG. 4*d*). AAV-F showed levels in the liver similar to AAV9, and AAV-S showed a lower, but non-significant trend downwards. We also examined the biodistribution of AAV-F compared to AAV9 in several other organs—skeletal muscle, heart, and spinal cord (FIG. 11). We observed no significant difference between the two vectors in muscle and heart (although an upward trend was seen with respect to AAV-F in the heart). As would be expected from expression in the brain, AAV-F showed significantly higher expression levels in the spinal cord compared to AAV9 ($p<0.05$, t-test).

Figure 4E:
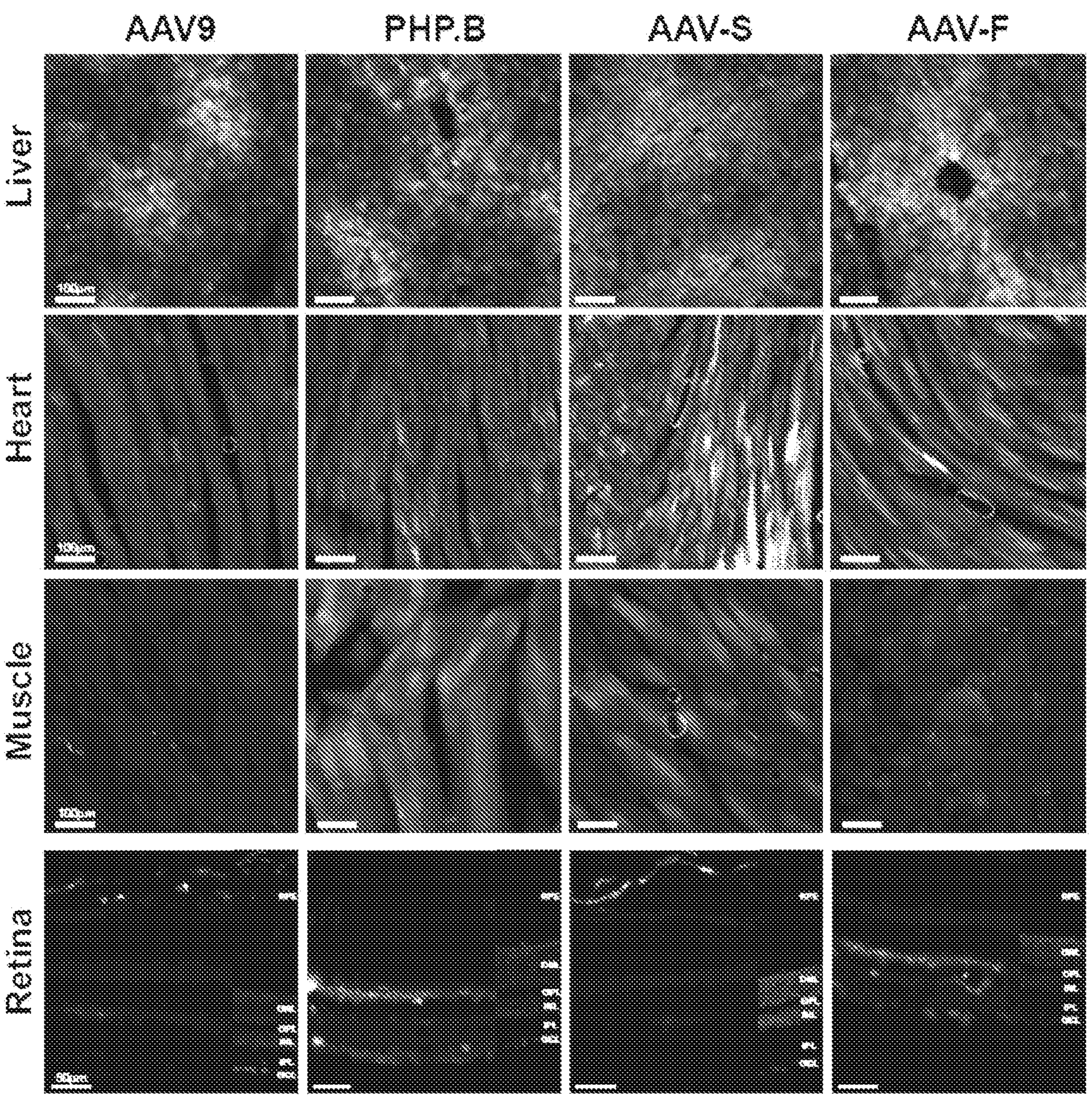

To investigate transgene expression in peripheral organs after systemic injection, we analyzed GFP fluorescence in the liver, heart, skeletal muscle, and retina (FIG. 4*e*). Not surprisingly, all vectors transduced liver efficiently. In the heart and skeletal muscle, AAV-S yielded higher numbers of bright GFP signal/section than AAV9 and AAV-F. All capsids mediated low transduction of the retina, as expected with intravenous delivery. Interestingly, while AAV-9 and AAV-S did not transduce the neuronal retina, consistent expression was observed in the retinal pigment epithelium (RPE). Both AAV9-PHP.B and AAV-F transduced multiple layers in the retina, most notably cells in the ganglion cell layer (GCL). GFP expression was also observed in the inner nuclear layer (INL), with substantial expression shown in the outer plexiform layer (OPL), which may reflect bipolar or inhibitory horizontal cell transduction.

Figure 5C:
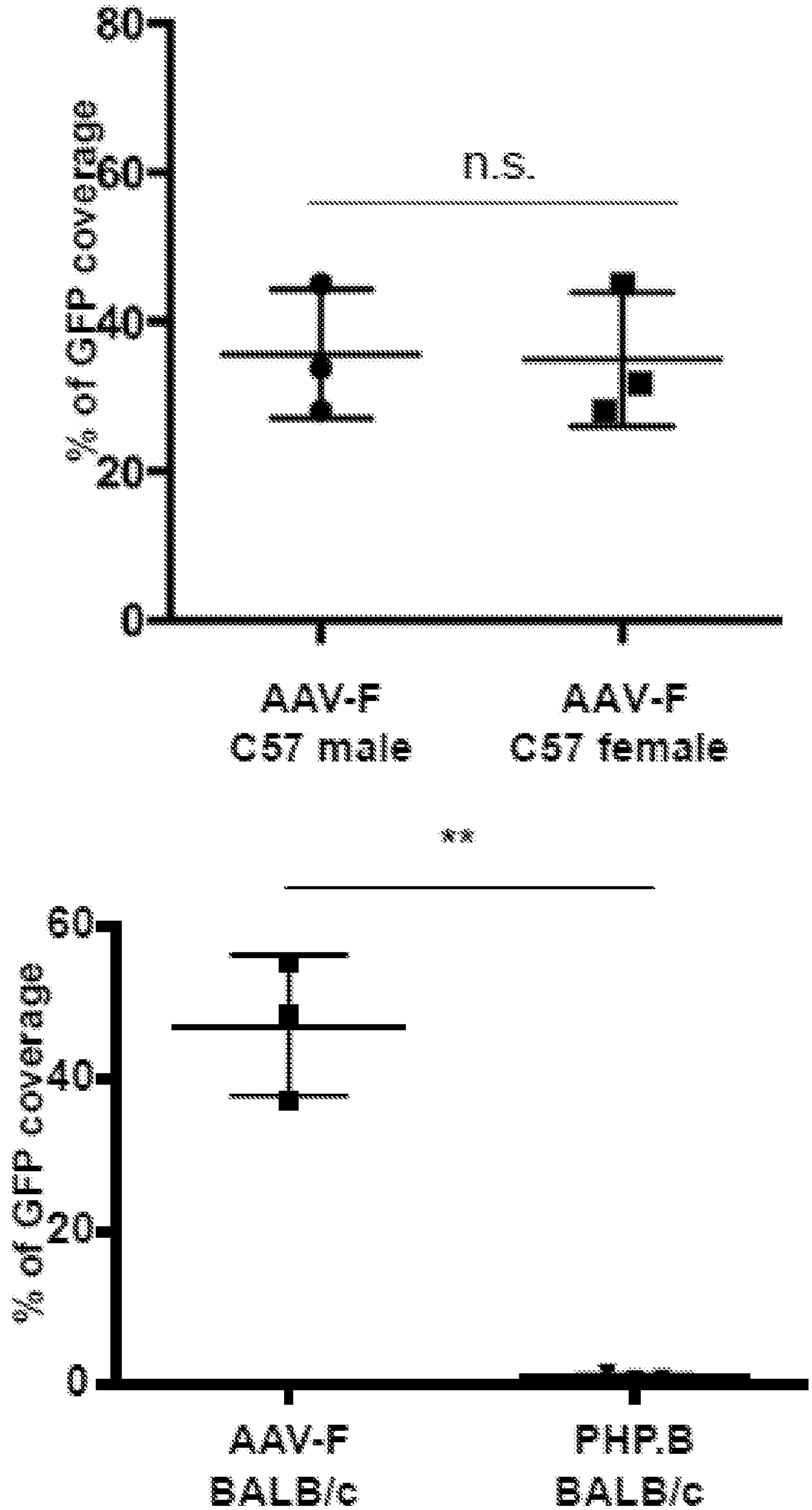

Since transduction by AAV vectors in mice can vary substantially between sex and mouse strain, we examined whether the most efficient capsid, AAV-F could efficiently transduce brain after systemic injection of female C57BL/6 as well as male BALB/c. Mice were injected with $1\times10^{11}$ *vg* ($4\times10^{12}$ vg/kg), and we observed robust and efficient transduction independent of strain or sex (FIG. 5*a-c*). These results contrasted with the lack of efficacy of AAV9-PHP.B at transducing the central nervous system after systemic delivery in the BALB/c strain, as previously reported (FIG. 5*b, c*.)[13, 14]

While iodixanol density gradient purification removes the majority of empty capsids, to examine if an excess of empty capsids in AAV-F could explain its increased biodistribution to the brain compared to AAV9, we performed transmission electron microscopy (TEM) on two separate preparations of AAV-F, and compared them to two independent preparations of AAV9. As seen in FIGS. 12A-E, we observed no significant difference in empty capsid levels between AAV-F and AAV9 (mean 4.63±1.99% vs. 5.2±2.18% empty capsids for AAV9 and AAV-F respectively, mean+SD, p=0.54, unpaired t-test).

Next, we tested whether AAV-F would have utility as a vector for CNS transduction via other routes of administration. We first tested AAV-S and AAV-F to mediate transgene expression in the brain after direct hippocampal injection of adult C57BL/6 mice. We found that both capsids achieve a widespread expression of GFP after direct injection, primarily in neurons (FIG. 13). Intrathecal injection of AAV vectors to transduce the spinal cord, has shown promise to treat this compartment. One drawback is limited spread of the vector to the brain after lumbar injection of vector. We compared AAV9 and AAV-F after bolus intrathecal injection of vector into the lumbar region of the spinal cord in adult C57BL/6 mice. Three weeks post injection, mice were killed and spinal cords and brains analyzed. Remarkably, AAV-F resulted in much more intense GFP expression throughout the spinal cord compared to AAV9, transducing both white and gray matter. Meanwhile AAV9 transduction was mainly restricted to the white matter. Strikingly, we also detected transduction of astrocytes and neurons in the brain of mice injected with AAV-F, but not AAV9 (FIG. 14).

Example 4. AAV-F Mediates Enhanced Transduction of Human Neurons

Figure 6A:
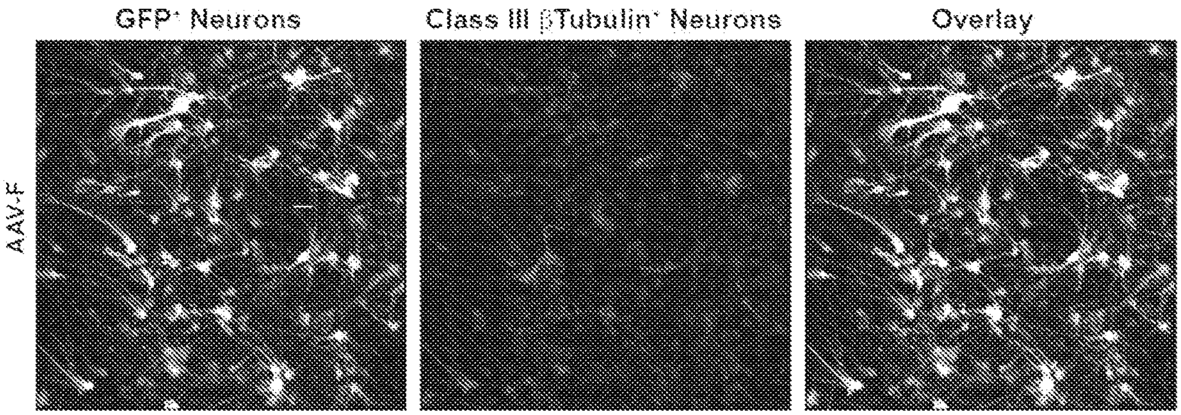
FIGS. 6A-B. AAV-F mediates higher transduction efficiency than AAV9 in human cortical neurons. a. GFP expression in fetal-derived primary human neurons, transduced by AAV-F. Neurons were co-labelled with an antibody to β-Tubulin to quantify transduction. b. Quantitation of transduction efficiency of human neurons by AAV9, AAV-S and AAV-F. *, $p<0.05$.
Figure 6B:
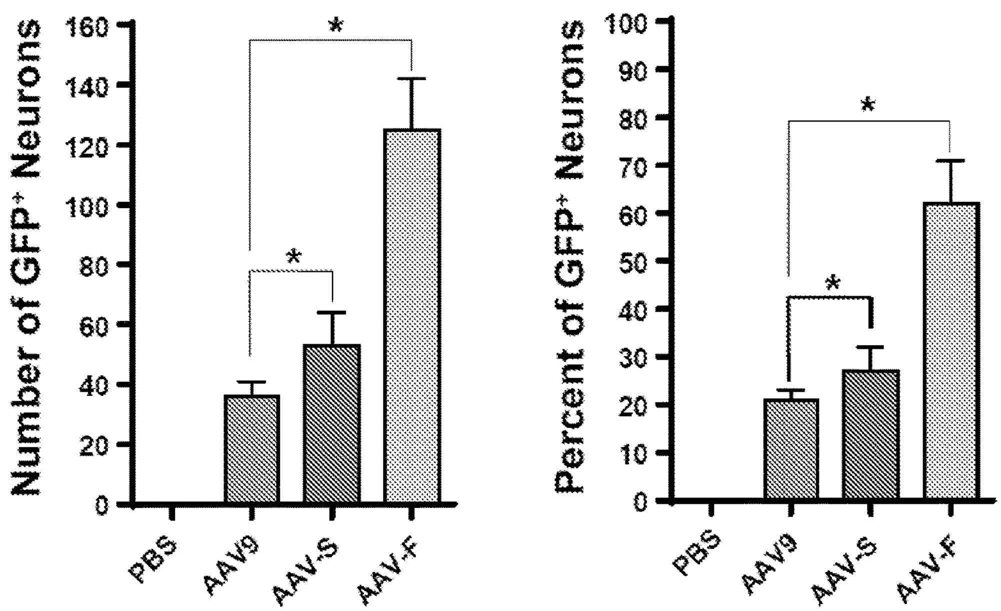

Since the selection was performed in mice, we analyzed if the robust transduction characteristics of AAV-F also translated to human cells. Primary human stem cell-derived neurons were transduced with equal doses of AAV9, AAV-S and AAV-F, all encoding GFP. One week later they were fixed, stained with Class III β Tubulin and analyzed for the percentage of GFP positive neurons. Remarkably, AAV-F transduced 62% of neurons, 3-fold higher than AAV9 ($p<0.05$) (FIG. 6*a, b*). AAV-S yielded a slight, yet statistically significant ($p<0.05$) increase in transduction efficiency over AAV9 (FIG. 6*a*).

Example 5. AAV-S Transduces the Inner Ear with High Efficiency

Recent years have seen the development of new AAV vectors, designed to target specific organs and cell types with high efficacy. Many of these utilize 7-mer peptide insertions that modify the transduction properties of a particular AAV serotype. However, these vectors can often be repurposed to transduce other tissues, including those that are difficult to treat, such as the inner ear. Transducing certain cell types in the inner ear—such as hair cells—remains a challenge, with many conventional AAV vectors failing to consistently target one class of hair cells, outer hair cells (OHCs).

As noted above, one (AAV-F) showed great promise and high CNS expression after systemic injection, whereas the other (AAV-S) did not. While systemically injected AAV-S did not cross the blood-brain barrier effectively, it transduced a variety of tissues including heart, liver, and muscle. After direct injection into the brain, AAV-S displayed high local transduction efficiency in neurons, even at relatively low doses. To assay its transduction properties in the inner ear, we produced AAV-S encoding a single-stranded expression cassette driving EGFP under the CBA promoter, and injected it in neonatal (P1) mice via the round window. We found that AAV-S transduces hair cells of the cochlea extremely well. Both inner and outer hair cells were transduced with efficiencies of up to 100% and 99% (FIGS. 15*a, b*) at the dose tested ($2\times10^{10}$ VG). We also observed significant transduction of the spiral limbus and spiral ganglion (FIGS. 15*c, d*). Overall, we show here that AAV-S can be used for genetic therapies of the inner ear.

Example 6. Using the iTransduce System for Selections in Non-Transgenic Adult Primates to Isolate Capsids that Transduce Fibrocytes Efficiently 2-3 rounds of selection for fibrocyte-targeting AAV capsids are performed in non-human primates, e.g., cynomolgus monkeys. To identify fibrocyte-selective, transduction-competent AAV capsid selection is performed by co-injecting the iTransduce AAV library along with AAV9-PHP.B which encodes a GJB2-floxed-STOP-tdTomato cassette (size fits inside AAV capsid). In NHP inner ear, AAV9-PHP.B-CBA-GFP transduces many cells of the cochlea including fibrocytes, HCs, and spiral ganglion neuron region. In this selection strategy (see FIG. 16A), tdTomato expression is restricted to fibrocytes under the GJB2 promoter, essentially creating an inner ear transgenic NHP. AAV capsids that enter fibrocytes and turn on tdTomato are flow sorted from dissociated cochlea and capsid DNA rescued for NGS and cloning to identify peptide sequences that allow AAV mediated expression in fibrocytes. Individual peptide enrichment is followed by deep-sequencing as described above to inform when to stop additional rounds of selection (likely when a particular peptide represents >25% of reads).

Alternatively or in addition, 2-3 rounds of selection for spinal cord cell targeting AAV capsids are performed in non-human primates, e.g., cynomolgus monkeys. To identify spinal cord-selective, transduction-competent AAV capsids, selection is performed by co-injecting the iTransduce AAV library along with AAV9 which encodes a CBA-floxed-STOP-mPlum cassette (size fits inside AAV capsid). In NHP spinal cord, AAV9-transduces cells including neurons and astrocytes. In this selection strategy (see FIG. 16B), AAV capsids that enter spinal cord cells and turn on mPlum fluorescence are flow sorted from dissociated spinal cord and capsid DNA rescued for NGS and cloning to identify peptide sequences that allow AAV mediated expression in cells of the spinal cord. Individual peptide enrichment is followed by deep-sequencing as described above to inform when to stop additional rounds of selection (likely when a particular peptide represents >25% of reads).

Once candidate capsids clones are identified, the capsids are vectorized as before, encoding a GFP cassette. Next, the capsids are tested for transduction of target cells after direct round window membrane (RMW) injection (e.g., as shown in 16A), or intrathecal injection (e.g., as shown in 16B).

REFERENCES

1. Mendell, J. R., S. Al-Zaidy, R. Shell, W. D. Arnold, L. R. Rodino-Klapac, T. W. Prior, L. Lowes, L. Alfano, K.

Berry, K. Church, J. T. Kissel, S. Nagendran, J. L'Italien, D. M. Sproule, C. Wells, J. A. Cardenas, M. D. Heitzer, A. Kaspar, S. Corcoran, L. Braun, S. Likhite, C. Miranda, K. Meyer, K. D. Foust, A. H. M. Burghes, and B. K. Kaspar, Single-Dose Gene-Replacement Therapy for Spinal Muscular Atrophy. N Engl J Med, 2017. 377(18): p. 1713-1722.

2. Manno, C. S., G. F. Pierce, V. R. Arruda, B. Glader, M. Ragni, J. J. Rasko, M. C. Ozelo, K. Hoots, P. Blatt, B. Konkle, M. Dake, R. Kaye, M. Razavi, A. Zajko, J. Zehnder, P. K. Rustagi, H. Nakai, A. Chew, D. Leonard, J. F. Wright, R. R. Lessard, J. M. Sommer, M. Tigges, D. Sabatino, A. Luk, H. Jiang, F. Mingozzi, L. Couto, H. C. Ertl, K. A. High, and M. A. Kay, Successful transduction of liver in hemophilia by AAV-Factor IX and limitations imposed by the host immune response. Nat Med, 2006. 12(3): p. 342-7.

3. Hinderer, C., N. Katz, E. L. Buza, C. Dyer, T. Goode, P. Bell, L. K. Richman, and J. M. Wilson, Severe Toxicity in Nonhuman Primates and Piglets Following High-Dose Intravenous Administration of an Adeno-Associated Virus Vector Expressing Human SMN. Hum Gene Ther, 2018. 29(3): p. 285-298.

4. Paulk, N. K., K. Pekrun, G. W. Charville, K. Maguire-Nguyen, M. N. Wosczyna, J. Xu, Y. Zhang, L. Lisowski, B. Yoo, J. G. Vilches-Moure, G. K. Lee, J. B. Shrager, T. A. Rando, and M. A. Kay, Bioengineered Viral Platform for Intramuscular Passive Vaccine Delivery to Human Skeletal Muscle. Mol Ther Methods Clin Dev, 2018. 10: p. 144-155.

5. Paulk, N. K., K. Pekrun, E. Zhu, S. Nygaard, B. Li, J. Xu, K. Chu, C. Leborgne, A. P. Dane, A. Haft, Y. Zhang, F. Zhang, C. Morton, M. B. Valentine, A. M. Davidoff, A. C. Nathwani, F. Mingozzi, M. Grompe, I. E. Alexander, L. Lisowski, and M. A. Kay, Bioengineered AAV Capsids with Combined High Human Liver Transduction In Vivo and Unique Humoral Seroreactivity. Mol Ther, 2018. 26(1): p. 289-303.

6. Gray, S. J., B. L. Blake, H. E. Criswell, S. C. Nicolson, R. J. Samulski, T. J. McCown, and W. Li, Directed evolution of a novel adeno-associated virus (AAV) vector that crosses the seizure-compromised blood-brain barrier (BBB). Mol Ther, 2010. 18(3): p. 570-8.

7. Tse, L. V., K. A. Klinc, V. J. Madigan, R. M. Castellanos Rivera, L. F. Wells, L. P. Havlik, J. K. Smith, M. Agbandje-McKenna, and A. Asokan, Structure-guided evolution of antigenically distinct adeno-associated virus variants for immune evasion. Proc Natl Acad Sci USA, 2017. 114(24): p. E4812-E4821.

8. Koerber, J. T., N. Maheshri, B. K. Kaspar, and D. V. Schaffer, Construction of diverse adeno-associated viral libraries for directed evolution of enhanced gene delivery vehicles. Nat Protoc, 2006. 1(2): p. 701-6.

9. Korbelin, J., T. Sieber, S. Michelfelder, L. Lunding, E. Spies, A. Hunger, M. Alawi, K. Rapti, D. Indenbirken, O. J. Muller, R. Pasqualini, W. Arap, J. A. Kleinschmidt, and M. Trepel, Pulmonary Targeting of Adeno-associated Viral Vectors by Next-generation Sequencing-guided Screening of Random Capsid Displayed Peptide Libraries. Mol Ther, 2016. 24(6): p. 1050-1061.

10. Sallach, J., G. Di Pasquale, F. Larcher, N. Niehoff, M. Rubsam, A. Huber, J. Chiorini, D. Almarza, S. A. Eming, H. Ulus, S. Nishimura, U. T. Hacker, M. Hallek, C. M. Niessen, and H. Buning, Tropism-modified AAV vectors overcome barriers to successful cutaneous therapy. Mol Ther, 2014. 22(5): p. 929-39.

11. Berry, G. E. and A. Asokan, Cellular transduction mechanisms of adeno-associated viral vectors. Curr Opin Virol, 2016. 21: p. 54-60.

12. Deverman, B. E., P. L. Pravdo, B. P. Simpson, S. R. Kumar, K. Y. Chan, A. Banerjee, W. L. Wu, B. Yang, N. Huber, S. P. Pasca, and V. Gradinaru, Cre-dependent selection yields AAV variants for widespread gene transfer to the adult brain. Nat Biotechnol, 2016. 34(2): p. 204-9.

13. Matsuzaki, Y., M. Tanaka, S. Hakoda, T. Masuda, R. Miyata, A. Konno, and H. Hirai, Neurotropic Properties of AAV-PHP.B Are Shared among Diverse Inbred Strains of Mice. Mol Ther, 2019. 27(4): p. 700-704.

14. Hordeaux, J., Q. Wang, N. Katz, E. L. Buza, P. Bell, and J. M. Wilson, The Neurotropic Properties of AAV-PHP.B Are Limited to C57BL/6J Mice. Mol Ther, 2018. 26(3): p. 664-668.

15. Nonnenmacher, M., H. van Bakel, R. J. Hajjar, and T. Weber, High capsid-genome correlation facilitates creation of AAV libraries for directed evolution. Mol Ther, 2015. 23(4): p. 675-82.

16. Hordeaux, J., Y. Yuan, P. M. Clark, Q. Wang, R. A. Martino, J. J. Sims, P. Bell, A. Raymond, W. L. Stanford, and J. M. Wilson, The GPI-Linked Protein LY6A Drives AAV-PHP.B Transport across the Blood-Brain Barrier. Mol Ther, 2019. 27(5): p. 912-921.

17. Igarashi, H., K. Koizumi, R. Kaneko, K. Ikeda, R. Egawa, Y. Yanagawa, S. Muramatsu, H. Onimaru, T. Ishizuka, and H. Yawo, A Novel Reporter Rat Strain That Conditionally Expresses the Bright Red Fluorescent Protein tdTomato. PLoS One, 2016. 11(5): p. e0155687.

18. Park, J. E., X. F. Zhang, S. H. Choi, J. Okahara, E. Sasaki, and A. C. Silva, Generation of transgenic marmosets expressing genetically encoded calcium indicators. Sci Rep, 2016. 6: p. 34931.

19. Sasaki, E., H. Suemizu, A. Shimada, K. Hanazawa, R. Oiwa, M. Kamioka, I. Tomioka, Y. Sotomaru, R. Hirakawa, T. Eto, S. Shiozawa, T. Maeda, M. Ito, R. Ito, C. Kito, C. Yagihashi, K. Kawai, H. Miyoshi, Y. Tanioka, N. Tamaoki, S. Habu, H. Okano, and T. Nomura, Generation of transgenic non-human primates with germline transmission. Nature, 2009. 459(7246): p. 523-7.

20. D'Costa, S., V. Blouin, F. Broucque, M. Penaud-Budloo, A. Francois, I. C. Perez, C. Le Bec, P. Moullier, R. O. Snyder, and E. Ayuso, Practical utilization of recombinant AAV vector reference standards: focus on vector genomes titration by free ITR qPCR. Mol Ther Methods Clin Dev, 2016. 5: p. 16019.

21. Aurnhammer, C., M. Haase, N. Muether, M. Hausl, C. Rauschhuber, I. Huber, H. Nitschko, U. Busch, A. Sing, A. Ehrhardt, and A. Baiker, Universal real-time PCR for the detection and quantification of adeno-associated virus serotype 2-derived inverted terminal repeat sequences. Hum Gene Ther Methods, 2012. 23(1): p. 18-28.

22. Gyorgy, B., E. J. Meijer, M. V. Ivanchenko, K. Tenneson, F. Emond, K. S. Hanlon, A. A. Indzhykulian, A. Volak, K. D. Karavitaki, P. I. Tamvakologos, M. Vezina, V. K. Berezovskii, R. T. Born, M. O'Brien, J. F. Lafond, Y. Arsenijevic, M. A. Kenna, C. A. Maguire, and D. P. Corey, Gene Transfer with AAV9-PHP.B Rescues Hearing in a Mouse Model of Usher Syndrome 3A and Transduces Hair Cells in a Non-human Primate. Mol Ther Methods Clin Dev, 2019. 13: p. 1-13.

23. Maguire, C. A., L. Balaj, S. Sivaraman, M. H. Crommentuijn, M. Ericsson, L. Mincheva-Nilsson, V. Baranov, D. Gianni, B. A. Tannous, M. Sena-Esteves, X. O.

Breakefield, and J. Skog, Microvesicle-associated AAV vector as a novel gene delivery system. Mol Ther, 2012. 20(5): p. 960-71.
24. Hudry, E., C. Martin, S. Gandhi, B. Gyorgy, D. I. Scheffer, D. Mu, S. F. Merkel, F. Mingozzi, Z. Fitzpatrick, H. Dimant, M. Masek, T. Ragan, S. Tan, A. R. Brisson, S. H. Ramirez, B. T. Hyman, and C. A. Maguire, Exosome-associated AAV vector as a robust and convenient neuroscience tool. Gene Ther, 2016. 23(4): p. 380-92.
25. Dashkoff, J., E. P. Lerner, N. Truong, J. A. Klickstein, Z. Fan, D. Mu, C. A. Maguire, B. T. Hyman, and E. Hudry, Tailored transgene expression to specific cell types in the central nervous system after peripheral injection with AAV9. Mol Ther Methods Clin Dev, 2016. 3: p. 16081.
26. Watters, A. K., S. Rom, J. D. Hill, M. K. Dematatis, Y. Zhou, S. F. Merkel, A. M. Andrews, J. Cena, R. Potula, A. Skuba, Y. J. Son, Y. Persidsky, and S. H. Ramirez, Identification and dynamic regulation of tight junction protein expression in human neural stem cells. Stem Cells Dev, 2015. 24(12): p. 1377-89.
27. Akil, O., Dyka, F., Calvet, C., Emptoz, A., Lahlou, G., Nouaille, S., De Monvel, J. B., Hardelin, J. P., Hauswirth, W. W., Avan, P., Petit, C., Safieddine, S., and Lustig, L. R. (2019). Dual AAV-mediated gene therapy restores hearing in a DFNB9 mouse model. *Proc. Natl. Acad. Sci. U.S.A* doi:10.1073/pnas.1817537116.
28. Al-Zaidy, S. A., Kolb, S. J., Lowes, L., Alfano, L. N., Shell, R., Church, K. R., Nagendran, S., Sproule, D. M., Feltner, D. E., Wells, C., Ogrinc, F., Menier, M., L'Italien, J., Arnold, W. D., Kissel, J. T., Kaspar, B. K., and Mendell, J. R. (2019). AVXS-101 (Onasemnogene Abeparvovec) for SMA1: Comparative Study with a Prospective Natural History Cohort. J. Neuromuscul. Dis. doi:10.3233/JND-190403.
29. Caron, N. S., Southwell, A. L., Brouwers, C. C., Cengio, L. D., Xie, Y., Black, H. F., Anderson, L. M., Ko, S., Zhu, X., van Deventer, S. J., Evers, M. M., Konstantinova, P., and Hayden, M. R. (2020). Potent and sustained huntingtin lowering via AAV5 encoding miRNA preserves striatal volume and cognitive function in a humanized mouse model of Huntington disease. *Nucleic Acids Res*. doi:10.1093/nar/gkz976.
30. Cehajic-Kapetanovic, J., Xue, K., Martinez-Fernandez de la Camara, C., Nanda, A., Davies, A., Wood, L. J., Salvetti, A. P., Fischer, M. D., Aylward, J. W., Barnard, A. R., Jolly, J. K., Luo, E., Lujan, B. J., Ong, T., Girach, A., Black, G. C. M., Gregori, N. Z., Davis, J. L., Rosa, P. R., Lotery, A. J., Lam, B. L., Stanga, P. E., and MacLaren, R. E. (2020). Initial results from a first-in-human gene therapy trial on X-linked retinitis pigmentosa caused by mutations in RPGR. *Nat. Med*. doi:10.1038/s41591-020-0763-1.
31. Christine, C. W., Bankiewicz, K. S., Van Laar, A. D., Richardson, R. M., Ravina, B., Kells, A. P., Boot, B., Martin, A. J., Nutt, J., Thompson, M. E., and Larson, P. S. (2019). Magnetic resonance imaging-guided phase 1 trial of putaminal AADC gene therapy for Parkinson's disease. *Ann. Neurol*. doi:10.1002/ana.25450.
32. Duan, D. (2018). Systemic AAV Micro-dystrophin Gene Therapy for Duchenne Muscular Dystrophy. *Mol. Ther*. doi:10.1016/j.ymthe.2018.07.011.
33. Eichler, F., Duncan, C., Musolino, P. L., Orchard, P. J., De Oliveira, S., Thrasher, A. J., Armant, M., Dansereau, C., Lund, T. C., Miller, W. P., Raymond, G. V., Sankar, R., Shah, A. J., Sevin, C., Gaspar, H. B., Gissen, P., Amartino, H., Bratkovic, D., Smith, N. J. C., Paker, A. M., Shamir, E., O'Meara, T., Davidson, D., Aubourg, P., and Williams, D. A. (2017). Hematopoietic stem-cell gene therapy for cerebral adrenoleukodystrophy. *N. Engl. J. Med*. doi:10.1056/NEJMoa1700554.
34. Gong, Y., Mu, D., Prabhakar, S., Moser, A., Musolino, P., Ren, J. Q., Breakefield, X. O., Maguire, C. A., and Eichler, F. S. (2015). Adenoassociated virus serotype 9-mediated gene therapy for X-linked adrenoleukodystrophy. *Mol. Ther*. doi:10.1038/mt.2015.6.
35. Griciuc, A., Serrano-Pozo, A., Parrado, A. R., Lesinski, A. N., Asselin, C. N., Mullin, K., Hooli, B., Choi, S. H., Hyman, B. T., and Tanzi, R. E. (2013). Alzheimer's disease risk gene cd33 inhibits microglial uptake of amyloid beta. *Neuron*. doi:10.1016/j.neuron.2013.04.014.
36. Gyorgy, B., Meijer, E. J., Ivanchenko, M. V., Tenneson, K., Emond, F., Hanlon, K. S., Indzhykulian, A. A., Volak, A., Karavitaki, K. D., Tamvakologos, P. I., Vezina, M., Berezovskii, V. K., Born, R. T., O'Brien, M., Lafond, J. F., Arsenijevic, Y., Kenna, M. A., Maguire, C. A., and Corey, D. P. (2019). Gene Transfer with AAV9-PHP.B Rescues Hearing in a Mouse Model of Usher Syndrome 3A and Transduces Hair Cells in a Non-human Primate. *Mol. Ther.—Methods Clin. Dev*. doi:10.1016/j.omtm.2018.11.003.
37. Hughes, M. P., Smith, D. A., Morris, L., Fletcher, C., Colaco, A., Huebecker, M., Tordo, J., Palomar, N., Massaro, G., Henckaerts, E., Waddington, S. N., Platt, F. M., and Rahim, A. A. (2018). AAV9 intracerebroventricular gene therapy improves lifespan, locomotor function and pathology in a mouse model of Niemann-Pick type C1 disease. *Hum. Mol. Genet*. doi:10.1093/hmg/ddy212.
38. Isgrig, K., Shteamer, J. W., Belyantseva, I. A., Drummond, M. C., Fitzgerald, T. S., Vijayakumar, S., Jones, S. M., Griffith, A. J., Friedman, T. B., Cunningham, L. L., and Chien, W. W. (2017). Gene Therapy Restores Balance and Auditory Functions in a Mouse Model of Usher Syndrome. *Mol. Ther*. doi:10.1016/j.ymthe.2017.01.007.
39. Keskin, S., Brouwers, C. C., Sogorb-Gonzalez, M., Martier, R., Depla, J. A., Vallès, A., van Deventer, S. J., Konstantinova, P., and Evers, M. M. (2019). AAV5-miHTT Lowers Huntingtin mRNA and Protein without Off-Target Effects in Patient-Derived Neuronal Cultures and Astrocytes. *Mol. Ther.—Methods Clin. Dev*. doi:10.1016/j.omtm.2019.09.010.
40. Leone, P., Shera, D., McPhee, S. W. J., Francis, J. S., Kolodny, E. H., Bilaniuk, L. T., Wang, D. J., Assadi, M., Goldfarb, O., Goldman, H. W., Freese, A., Young, D., During, M. J., Samulski, R. J., and Janson, C. G. (2012). Long-term follow-up after gene therapy for canavan disease. *Sci. Transl. Med*. doi:10.1126/scitranslmed.3003454.
41. Lopes, V. S., and Williams, D. S. (2015). Gene therapy for the retinal degeneration of usher syndrome caused by mutations in MYO7A. *Cold Spring Harb. Perspect. Med*. doi:10.1101/cshperspect.a017319.
42. Maguire, A. M., Russell, S., Wellman, J. A., Chung, D. C., Yu, Z. F., Tillman, A., Wittes, J., Pappas, J., Elci, O., Marshall, K. A., McCague, S., Reichert, H., Davis, M., Simonelli, F., Leroy, B. P., Wright, J. F., High, K. A., and Bennett, J. (2019). Efficacy, Safety, and Durability of Voretigene Neparvovec-rzyl in RPE65 Mutation-Associated Inherited Retinal Dystrophy: Results of Phase 1 and 3 Trials. *Ophthalmology*. doi:10.1016/j.ophtha.2019.06.017.
43. Millington-Ward, S., Chadderton, N., O'Reilly, M., Palfi, A., Goldmann, T., Kilty, C., Humphries, M., Wolfrum, U., Bennett, J., Humphries, P., Kenna, P. F., and Farrar, G. J. (2011). Suppression and Replacement Gene Therapy for Autosomal Dominant Disease in a Murine Model of Dominant Retinitis Pigmentosa. *Mol. Ther.* 19, 642-649. doi:10.1038/mt.2010.293.

44. Mookherjee, S., Hiriyanna, S., Kaneshiro, K., Li, Y., Li, W., Qian, H., Li, T., Colosi, P., Swaroop, A., Wu, Z., Li, L., and Khanna, H. (2015). Long-term rescue of cone photoreceptor degeneration in retinitis pigmentosa 2 (RP2)-knockout mice by gene replacement therapy. *Hum. Mol. Genet.* doi: 10.1093/hmg/ddv354.
45. Nathwani, A. C. (2019). Gene therapy for hemophilia. *Hematol.* (*United States*). doi:10.1182/hematology.2019000007.
46. Nist-Lund, C. A., Pan, B., Patterson, A., Asai, Y., Chen, T., Zhou, W., Zhu, H., Romero, S., Resnik, J., Polley, D. B., Géléoc, G. S., and Holt, J. R. (2019). Improved TMC1 gene therapy restores hearing and balance in mice with genetic inner ear disorders. *Nat. Commun.* doi:10.1038/s41467-018-08264-w.
47. Remes, A., Franz, M., Zaradzki, M., Borowski, C., Frey, N., Karck, M., Kallenbach, K., Müller, O. J., Wagner, A. H., and Arif, R. (2020). AAV-mediated TIMP-1 overexpression in aortic tissue reduces the severity of allograft vasculopathy in mice. *J. Hear. Lung Transplant.* doi: 10.1016/j.healun.2020.01.1338.
48. Tan, F., Chu, C., Qi, J., Li, W., You, D., Li, K., Chen, X., Zhao, W., Cheng, C., Liu, X., Qiao, Y., Su, B., He, S., Zhong, C., Li, H., Chai, R., and Zhong, G. (2019). AAV-ie enables safe and efficient gene transfer to inner ear cells. *Nat. Commun.* doi:10.1038/s41467-019-11687-8.
49. Wan, X., Pei, H., Zhao, M., Yang, S., Hu, W., He, H., Ma, S., Zhang, G., Dong, X., Chen, C., Wang, D., and Li, B. (2016). Efficacy and Safety of rAAV2-ND4 Treatment for Leber's Hereditary Optic Neuropathy. *Sci. Rep.* 6, 1-10. doi:10.1038/srep21587.
50. Yang, S., Ma, S.-Q., Wan, X., He, H., Pei, H., Zhao, M.-J., Chen, C., Wang, D.-W., Dong, X.-Y., Yuan, J.-J., and Li, B. (2016). Long-term outcomes of gene therapy for the treatment of Leber's hereditary optic neuropathy. *EBioMedicine* 10, 258-268. doi:10.1016/j.ebiom.2016.07.002.
51. Yu, W., Mookherjee, S., Chaitankar, V., Hiriyanna, S., Kim, J. W., Brooks, M., Ataeijannati, Y., Sun, X., Dong, L., Li, T., Swaroop, A., and Wu, Z. (2017). Nrl knockdown by AAV-delivered CRISPR/Cas9 prevents retinal degeneration in mice. *Nat. Commun.* doi:10.1038/ncomms14716.
52. Zhang, W., Kim, S. M., Wang, W., Cai, C., Feng, Y., Kong, W., and Lin, X. (2018). Cochlear Gene Therapy for Sensorineural Hearing Loss: Current Status and Major Remaining Hurdles for Translational Success. Front. *Mol. Neurosci.* doi:10.3389/fnmol.2018.00221.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An adeno-associated vector (AAV) capsid protein comprising an amino acid sequence that comprises at least five contiguous amino acids from STTLYSP (SEQ ID NO: 1) or FVVGQSY (SEQ ID NO:2), wherein the contiguous amino acids are inserted between residues 588 and 589 of SEQ ID NO: 6.

2. The AAV capsid protein of claim 1, comprising an amino acid sequence that comprises at least six contiguous amino acids from STTLYSP (SEQ ID NO: 1) or FVVGQSY (SEQ ID NO: 2).

* * * * *

SEQUENCE LISTING

```
<160> NUMBER OF SEQ ID NOS: 149

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ser Thr Thr Leu Tyr Ser Pro
1               5


<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Phe Val Val Gly Gln Ser Tyr
1               5


<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3
```

```
Phe Gln Pro Cys Pro
1               5


<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Pro Ser Tyr Leu Thr Thr Ser
1               5


<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Tyr Ser Gln Gly Val Val Phe
1               5


<210> SEQ ID NO 6
<211> LENGTH: 736
<212> TYPE: PRT
<213> ORGANISM: Adeno-associated virus 9

<400> SEQUENCE: 6

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205
```

-continued

```
Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
```

-continued 625 630 635 640

Lys His Pro Pro Pro Gln Ile Leu Ile Lys Asn Thr Pro Val Pro Ala
645 650 655

Asp Pro Pro Thr Ala Phe Asn Lys Asp Lys Leu Asn Ser Phe Ile Thr
660 665 670

Gln Tyr Ser Thr Gly Gln Val Ser Val Glu Ile Glu Trp Glu Leu Gln
675 680 685

Lys Glu Asn Ser Lys Arg Trp Asn Pro Glu Ile Gln Tyr Thr Ser Asn
690 695 700

Tyr Tyr Lys Ser Asn Asn Val Glu Phe Ala Val Asn Thr Glu Gly Val
705 710 715 720

Tyr Ser Glu Pro Arg Pro Ile Gly Thr Arg Tyr Leu Thr Arg Asn Leu
725 730 735

<210> SEQ ID NO 7
<211> LENGTH: 743
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 7

Met Ala Ala Asp Gly Tyr Leu Pro Asp Trp Leu Glu Asp Asn Leu Ser
1 5 10 15

Glu Gly Ile Arg Glu Trp Trp Ala Leu Lys Pro Gly Ala Pro Gln Pro
20 25 30

Lys Ala Asn Gln Gln His Gln Asp Asn Ala Arg Gly Leu Val Leu Pro
35 40 45

Gly Tyr Lys Tyr Leu Gly Pro Gly Asn Gly Leu Asp Lys Gly Glu Pro
50 55 60

Val Asn Ala Ala Asp Ala Ala Ala Leu Glu His Asp Lys Ala Tyr Asp
65 70 75 80

Gln Gln Leu Lys Ala Gly Asp Asn Pro Tyr Leu Lys Tyr Asn His Ala
85 90 95

Asp Ala Glu Phe Gln Glu Arg Leu Lys Glu Asp Thr Ser Phe Gly Gly
100 105 110

Asn Leu Gly Arg Ala Val Phe Gln Ala Lys Lys Arg Leu Leu Glu Pro
115 120 125

Leu Gly Leu Val Glu Glu Ala Ala Lys Thr Ala Pro Gly Lys Lys Arg
130 135 140

Pro Val Glu Gln Ser Pro Gln Glu Pro Asp Ser Ser Ala Gly Ile Gly
145 150 155 160

Lys Ser Gly Ala Gln Pro Ala Lys Lys Arg Leu Asn Phe Gly Gln Thr
165 170 175

Gly Asp Thr Glu Ser Val Pro Asp Pro Gln Pro Ile Gly Glu Pro Pro
180 185 190

Ala Ala Pro Ser Gly Val Gly Ser Leu Thr Met Ala Ser Gly Gly Gly
195 200 205

Ala Pro Val Ala Asp Asn Asn Glu Gly Ala Asp Gly Val Gly Ser Ser
210 215 220

Ser Gly Asn Trp His Cys Asp Ser Gln Trp Leu Gly Asp Arg Val Ile
225 230 235 240

Thr Thr Ser Thr Arg Thr Trp Ala Leu Pro Thr Tyr Asn Asn His Leu
245 250 255

```
Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Phe Val Val Gly
            580                 585                 590

Gln Ser Tyr Ala Gln Ala Gln Thr Gly Trp Val Gln Asn Gln Gly Ile
        595                 600                 605

Leu Pro Gly Met Val Trp Gln Asp Arg Asp Val Tyr Leu Gln Gly Pro
    610                 615                 620

Ile Trp Ala Lys Ile Pro His Thr Asp Gly Asn Phe His Pro Ser Pro
625                 630                 635                 640

Leu Met Gly Gly Phe Gly Met Lys His Pro Pro Pro Gln Ile Leu Ile
                645                 650                 655

Lys Asn Thr Pro Val Pro Ala Asp Pro Pro Thr Ala Phe Asn Lys Asp
            660                 665                 670

Lys Leu Asn Ser Phe Ile Thr Gln Tyr Ser Thr Gly Gln Val Ser Val
```

-continued

```
        675                 680                 685

Glu Ile Glu Trp Glu Leu Gln Lys Glu Asn Ser Lys Arg Trp Asn Pro
    690                 695                 700

Glu Ile Gln Tyr Thr Ser Asn Tyr Tyr Lys Ser Asn Asn Val Glu Phe
705                 710                 715                 720

Ala Val Asn Thr Glu Gly Val Tyr Ser Glu Pro Arg Pro Ile Gly Thr
                725                 730                 735

Arg Tyr Leu Thr Arg Asn Leu
            740


<210> SEQ ID NO 8
<211> LENGTH: 2229
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8

atggctgccg atggttatct tccagattgg ctcgaggaca accttagtga aggaattcgc     60

gagtggtggg ctttgaaacc tggagcccct caacccaagg caaatcaaca acatcaagac    120

aacgctcgag gtcttgtgct tccgggttac aaataccttg gacccggcaa cggactcgac    180

aagggggagc cggtcaacgc agcagacgcg gcggccctcg agcacgacaa ggcctacgac    240

cagcagctca aggccggaga caacccgtac ctcaagtaca accacgccga cgccgagttc    300

caggagcggc tcaaagaaga tacgtctttt gggggcaacc tcgggcgagc agtcttccag    360

gccaaaaaga ggcttcttga acctcttggt ctggttgagg aagcggctaa gacggctcct    420

ggaaagaaga ggcctgtaga gcagtctcct caggaaccgg actcctccgc gggtattggc    480

aaatcgggtg cacagcccgc taaaaagaga ctcaatttcg gtcagactgg cgacacagag    540

tcagtcccag accctcaacc aatcggagaa cctcccgcag ccccctcagg tgtgggatct    600

cttacaatgg cttcaggtgg tggcgcacca gtggcagaca ataacgaagg tgccgatgga    660

gtgggtagtt cctcgggaaa ttggcattgc gattcccaat ggctggggga cagagtcatc    720

accaccagca cccgaacctg ggccctgccc acctacaaca atcacctcta caagcaaatc    780

tccaacagca catctggagg atcttcaaat gacaacgcct acttcggcta cagcaccccc    840

tgggggtatt ttgacttcaa cagattccac tgccacttct caccacgtga ctggcagcga    900

ctcatcaaca acaactgggg attccggcct aagcgactca acttcaagct cttcaacatt    960

caggtcaaag aggttacgga caacaatgga gtcaagacca tcgccaataa ccttaccagc   1020

acggtccagg tcttcacgga ctcagactat cagctcccgt acgtgctcgg gtcggctcac   1080

gagggctgcc tcccgccgtt cccagcggac gttttcatga ttcctcagta cgggtatctg   1140

acgcttaatg atggaagcca ggccgtgggt cgttcgtcct tttactgcct ggaatatttc   1200

ccgtcgcaaa tgctaagaac gggtaacaac ttccagttca gctacgagtt tgagaacgta   1260

cctttccata gcagctacgc tcacagccaa agcctggacc gactaatgaa tccactcatc   1320

gaccaatact tgtactatct ctcaaagact attaacggtt ctggacagaa tcaacaaacg   1380

ctaaaattca gtgtggccgg acccagcaac atggctgtcc agggaagaaa ctacatacct   1440

ggacccagct accgacaaca acgtgtctca accactgtga ctcaaaacaa caacagcgaa   1500

tttgcttggc ctggagcttc ttcttgggct ctcaatggac gtaatagctt gatgaatcct   1560

ggacctgcta tggccagcca caaagaagga gaggaccgtt tctttccttt gtctggatct   1620
```

-continued

```
ttaatttttg gcaaacaagg aactggaaga gacaacgtgg atgcggacaa agtcatgata   1680

accaacgaag aagaaattaa aactactaac ccggtagcaa cggagtccta tggacaagtg   1740

gccacaaacc accagagtgc ccaatttgtt gttggtcaga gttatgcaca ggcgcagacc   1800

ggctgggttc aaaaccaagg aatacttccg ggtatggttt ggcaggacag agatgtgtac   1860

ctgcaaggac ccatttgggc caaaattcct cacacggacg gcaactttca cccttctccg   1920

ctgatgggag ggtttggaat gaagcacccg cctcctcaga tcctcatcaa aaacacacct   1980

gtacctgcgg atcctccaac ggccttcaac aaggacaagc tgaactcttt catcacccag   2040

tattctactg gccaagtcag cgtggagatc gagtgggagc tgcagaagga aaacagcaag   2100

cgctggaacc cggagatcca gtacacttcc aactattaca agtctaataa tgttgaattt   2160

gctgttaata ctgaaggtgt atatagtgaa ccccgcccca ttggcaccag atacctgact   2220

cgtaatctg                                                           2229


<210> SEQ ID NO 9
<211> LENGTH: 743
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
```

-continued

```
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ser Thr Thr Leu
            580                 585                 590

Tyr Ser Pro Ala Gln Ala Gln Thr Gly Trp Val Gln Asn Gln Gly Ile
        595                 600                 605

Leu Pro Gly Met Val Trp Gln Asp Arg Asp Val Tyr Leu Gln Gly Pro
    610                 615                 620

Ile Trp Ala Lys Ile Pro His Thr Asp Gly Asn Phe His Pro Ser Pro
625                 630                 635                 640

Leu Met Gly Gly Phe Gly Met Lys His Pro Pro Pro Gln Ile Leu Ile
                645                 650                 655

Lys Asn Thr Pro Val Pro Ala Asp Pro Pro Thr Ala Phe Asn Lys Asp
            660                 665                 670
```

-continued

```
Lys Leu Asn Ser Phe Ile Thr Gln Tyr Ser Thr Gly Gln Val Ser Val
        675                 680                 685

Glu Ile Glu Trp Glu Leu Gln Lys Glu Asn Ser Lys Arg Trp Asn Pro
    690                 695                 700

Glu Ile Gln Tyr Thr Ser Asn Tyr Tyr Lys Ser Asn Asn Val Glu Phe
705                 710                 715                 720

Ala Val Asn Thr Glu Gly Val Tyr Ser Glu Pro Arg Pro Ile Gly Thr
                725                 730                 735

Arg Tyr Leu Thr Arg Asn Leu
            740


<210> SEQ ID NO 10
<211> LENGTH: 2229
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10

atggctgccg atggttatct tccagattgg ctcgaggaca accttagtga aggaattcgc     60

gagtggtggg ctttgaaacc tggagcccct caacccaagg caaatcaaca acatcaagac    120

aacgctcgag gtcttgtgct tccgggttac aaataccttg gacccggcaa cggactcgac    180

aagggggagc cggtcaacgc agcagacgcg gcggccctcg agcacgacaa ggcctacgac    240

cagcagctca aggccggaga caacccgtac ctcaagtaca accacgccga cgccgagttc    300

caggagcggc tcaaagaaga tacgtctttt gggggcaacc tcgggcgagc agtcttccag    360

gccaaaaaga ggcttcttga acctcttggt ctggttgagg aagcggctaa gacggctcct    420

ggaaagaaga ggcctgtaga gcagtctcct caggaaccgg actcctccgc gggtattggc    480

aaatcgggtg cacagcccgc taaaaagaga ctcaatttcg gtcagactgg cgacacagag    540

tcagtcccag accctcaacc aatcggagaa cctcccgcag ccccctcagg tgtgggatct    600

cttacaatgg cttcaggtgg tggcgcacca gtggcagaca ataacgaagg tgccgatgga    660

gtgggtagtt cctcgggaaa ttggcattgc gattcccaat ggctgggggga cagagtcatc    720

accaccagca cccgaacctg ggccctgccc acctacaaca atcacctcta caagcaaatc    780

tccaacagca catctggagg atcttcaaat gacaacgcct acttcggcta cagcaccccc    840

tgggggtatt ttgacttcaa cagattccac tgccacttct caccacgtga ctggcagcga    900

ctcatcaaca acaactgggg attccggcct aagcgactca acttcaagct cttcaacatt    960

caggtcaaag aggttacgga caacaatgga gtcaagacca tcgccaataa ccttaccagc   1020

acggtccagg tcttcacgga ctcagactat cagctcccgt acgtgctcgg gtcggctcac   1080

gagggctgcc tcccgccgtt cccagcggac gttttcatga ttcctcagta cgggtatctg   1140

acgcttaatg atggaagcca ggccgtgggt cgttcgtcct tttactgcct ggaatatttc   1200

ccgtcgcaaa tgctaagaac gggtaacaac ttccagttca gctacgagtt tgagaacgta   1260

cctttccata gcagctacgc tcacagccaa agcctggacc gactaatgaa tccactcatc   1320

gaccaatact tgtactatct ctcaaagact attaacggtt ctggacagaa tcaacaaacg   1380

ctaaaattca gtgtggccgg acccagcaac atggctgtcc agggaagaaa ctacatacct   1440

ggacccagct accgacaaca acgtgtctca accactgtga ctcaaaacaa caacagcgaa   1500

tttgcttggc ctggagcttc ttcttgggct ctcaatggac gtaatagctt gatgaatcct   1560
```

-continued

```
ggacctgcta tggccagcca caaagaagga gaggaccgtt tctttccttt gtctggatct   1620

ttaatttttg gcaaacaagg aactggaaga gacaacgtgg atgcggacaa agtcatgata   1680

accaacgaag aagaaattaa aactactaac ccggtagcaa cggagtccta tggacaagtg   1740

gccacaaacc accagagtgc ccaatctact acgctttata gtcctgcaca ggcgcagacc   1800

ggctgggttc aaaaccaagg aatacttccg ggtatggttt ggcaggacag agatgtgtac   1860

ctgcaaggac ccatttgggc caaaattcct cacacggacg gcaactttca cccttctccg   1920

ctgatgggag ggtttggaat gaagcacccg cctcctcaga tcctcatcaa aaacacacct   1980

gtacctgcgg atcctccaac ggccttcaac aaggacaagc tgaactcttt catcacccag   2040

tattctactg gccaagtcag cgtggagatc gagtgggagc tgcagaagga aaacagcaag   2100

cgctggaacc cggagatcca gtacacttcc aactattaca agtctaataa tgttgaattt   2160

gctgttaata ctgaaggtgt atatagtgaa ccccgcccca ttggcaccag atacctgact   2220

cgtaatctg                                                           2229
```

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 11

```
gtactatctc tctagaacta ttaacggttc                                      30
```

<210> SEQ ID NO 12
<211> LENGTH: 84
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (41)..(41)
<223> OTHER INFORMATION: a, c, t, g, unknown or other
<220> FEATURE:
<221> NAME/KEY: modified_base
<222> LOCATION: (43)..(44)
<223> OTHER INFORMATION: a, c, t, g, unknown or other
<220> FEATURE:
<221> NAME/KEY: modified_base
<222> LOCATION: (46)..(47)
<223> OTHER INFORMATION: a, c, t, g, unknown or other
<220> FEATURE:
<221> NAME/KEY: modified_base
<222> LOCATION: (49)..(50)
<223> OTHER INFORMATION: a, c, t, g, unknown or other
<220> FEATURE:
<221> NAME/KEY: modified_base
<222> LOCATION: (52)..(53)
<223> OTHER INFORMATION: a, c, t, g, unknown or other
<220> FEATURE:
<221> NAME/KEY: modified_base
<222> LOCATION: (55)..(56)
<223> OTHER INFORMATION: a, c, t, g, unknown or other
<220> FEATURE:
<221> NAME/KEY: modified_base
<222> LOCATION: (58)..(59)
<223> OTHER INFORMATION: a, c, t, g, unknown or other
<220> FEATURE:
<221> NAME/KEY: modified_base
<222> LOCATION: (61)..(62)
<223> OTHER INFORMATION: a, c, t, g, unknown or other

<400> SEQUENCE: 12
gtattccttg gttttgaacc caaccggtct gcgcctgtgc nmnnmnnmnn mnnmnnmnnm 60
nnttgggcac tctggtggtt tgtg 84

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 13
aatcctggac ctgctatggc 20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 14
tgccaaacca tacccggaag 20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 15
agctaccgac aacaacgtgt 20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
agaagggtga aagttgccgt 20

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 17
cagcctcgtc ttactgagct t 21

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 18

Gln Pro Arg Leu Thr Glu Leu
1 5

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 19
agtcatttta gtaattctat g 21

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 20

Ser His Phe Ser Asn Ser Met
1 5

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 21
ccgccttcta cggggaatcc t 21

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 22

Pro Pro Ser Thr Gly Asn Pro
1 5

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 23
aatagtcttg gggtgatgga t 21

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 24

Asn Ser Leu Gly Val Met Asp
1 5

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 25
cctcctatgg ctacgcctca g 21

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 26

Pro Pro Met Ala Thr Pro Gln
1 5

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 27
ccgcatactc gggctgagcc t 21

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 28

Pro His Thr Arg Ala Glu Pro
1 5

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 29
gtgaatcaga ctaattattc t 21

<210> SEQ ID NO 30
<211> LENGTH: 7
<212> TYPE: PRT
<213> ORGANISM: Artificial Sequence -continued

```
<220> FEATURE:
<223> OTHER INFORMATION: Description of Artificial Sequence: Synthetic
      peptide

<400> SEQUENCE: 30

Val Asn Gln Thr Asn Tyr Ser
1               5


<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31

catgcgccga ggctggttca g                                               21


<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

His Ala Pro Arg Leu Val Gln
1               5


<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33

tggagtaagg agtcgaatca t                                               21


<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Trp Ser Lys Glu Ser Asn His
1               5


<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35

actactgctg gtccgactga g                                               21


<210> SEQ ID NO 36
<211> LENGTH: 7
```

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 36

Thr Thr Ala Gly Pro Thr Glu
1 5

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 37
tcgtggccgc agtcgccttc g 21

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 38

Ser Trp Pro Gln Ser Pro Ser
1 5

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 39
acttgtgctg ttccggatcg g 21

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 40

Thr Cys Ala Val Pro Asp Arg
1 5

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 41
cctcgtgcgg agcctcggac g 21

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 42

Pro Arg Ala Glu Pro Arg Thr
1 5

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 43
cctactgcgg gtgtgtatct g 21

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 44

Pro Thr Ala Gly Val Tyr Leu
1 5

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 45
cagttgagta atacgacgtt g 21

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 46

Gln Leu Ser Asn Thr Thr Leu
1 5

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 47
cggatggata tggctgtgag g 21

-continued

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 48

Arg Met Asp Met Ala Val Arg
1 5

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 49
cggccgccgc ctgcgactcc t 21

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 50

Arg Pro Pro Pro Ala Thr Pro
1 5

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 51
cagtatctgt ttcatatttt t 21

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 52

Gln Tyr Leu Phe His Ile Phe
1 5

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 53
ggtgctggga ctcttacttc t 21

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 54

Gly Ala Gly Thr Leu Thr Ser
1 5

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 55
cctctttcgc gtgttgcttt g 21

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 56

Pro Leu Ser Arg Val Ala Leu
1 5

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 57
actactgcta agacgactgg g 21

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 58

Thr Thr Ala Lys Thr Thr Gly
1 5

<210> SEQ ID NO 59
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 59
tcgctgccgg ctactcatgt g 21

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 60

Ser Leu Pro Ala Thr His Val
1 5

<210> SEQ ID NO 61
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 61
agtgagaagg tgattcggag t 21

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 62

Ser Glu Lys Val Ile Arg Ser
1 5

<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 63
aagtcgacta tgcggaagcc g 21

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 64

Lys Ser Thr Met Arg Lys Pro
1 5

<210> SEQ ID NO 65
<211> LENGTH: 21
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 65

gtgtcgaagc agaatacgac t                                               21


<210> SEQ ID NO 66
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Val Ser Lys Gln Asn Thr Thr
1               5


<210> SEQ ID NO 67
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67

gctgatatga cggggcctac t                                               21


<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ala Asp Met Thr Gly Pro Thr
1               5


<210> SEQ ID NO 69
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69

cctactcgtg cgactcctat t                                               21


<210> SEQ ID NO 70
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Pro Thr Arg Ala Thr Pro Ile
1               5


<210> SEQ ID NO 71
<211> LENGTH: 21
<212> TYPE: DNA
```

<213> ORGANISM: Artificial Sequence
<220> FEATURE:
<223> OTHER INFORMATION: Description of Artificial Sequence: Synthetic
oligonucleotide

<400> SEQUENCE: 71
tcttggcctg ggctgttgct g 21

<210> SEQ ID NO 72
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 72

Ser Trp Pro Gly Leu Leu Leu
1 5

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 73
tggaggctgg agcagttgaa g 21

<210> SEQ ID NO 74
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 74

Trp Arg Leu Glu Gln Leu Lys
1 5

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 75
cttccgagtt ctccggtttt t 21

<210> SEQ ID NO 76
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 76

Leu Pro Ser Ser Pro Val Phe
1 5

<210> SEQ ID NO 77

<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 77
cctcagcggc atcagaatga t 21

<210> SEQ ID NO 78
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 78

Pro Gln Arg His Gln Asn Asp
1 5

<210> SEQ ID NO 79
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 79
tcgattccgt ttcggtatcc g 21

<210> SEQ ID NO 80
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 80

Ser Ile Pro Phe Arg Tyr Pro
1 5

<210> SEQ ID NO 81
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 81
cctgatggtc cgcaggctct g 21

<210> SEQ ID NO 82
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 82

Pro Asp Gly Pro Gln Ala Leu
1 5

<210> SEQ ID NO 83
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 83
tcgactacgt ggaagtctga t 21

<210> SEQ ID NO 84
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 84

Ser Thr Thr Trp Lys Ser Asp
1 5

<210> SEQ ID NO 85
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 85
ttgcagaaga tggctgttcc g 21

<210> SEQ ID NO 86
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 86

Leu Gln Lys Met Ala Val Pro
1 5

<210> SEQ ID NO 87
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 87
acggggtgta agtgttcgca g 21

<210> SEQ ID NO 88
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 88

Thr Gly Cys Lys Cys Ser Gln 1 5

<210> SEQ ID NO 89
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 89
catctgcctg ttatgaatga g 21

<210> SEQ ID NO 90
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 90

His Leu Pro Val Met Asn Glu
1 5

<210> SEQ ID NO 91
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 91
gtttcgttga attatactgc t 21

<210> SEQ ID NO 92
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 92

Val Ser Leu Asn Tyr Thr Ala
1 5

<210> SEQ ID NO 93
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 93
cctcctcctc ctccgcctgt g 21

<210> SEQ ID NO 94
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 94

Pro Pro Pro Pro Pro Pro Val
1               5

<210> SEQ ID NO 95
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
agttctactg ctagtcgtcg t 21

<210> SEQ ID NO 96
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Ser Ser Thr Ala Ser Arg Arg
1               5

<210> SEQ ID NO 97
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
ctgcttgtga cgtgtccgga t 21

<210> SEQ ID NO 98
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Leu Leu Val Thr Cys Pro Asp
1               5

<210> SEQ ID NO 99
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
tcgttgctgc gttatgctcc g 21

<210> SEQ ID NO 100
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Ser Leu Leu Arg Tyr Ala Pro
1 5

<210> SEQ ID NO 101
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 101
cagccgctgc gtccgaatct g 21

<210> SEQ ID NO 102
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 102

Gln Pro Leu Arg Pro Asn Leu
1 5

<210> SEQ ID NO 103
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 103
gctttggata ctcatcattg g 21

<210> SEQ ID NO 104
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 104

Ala Leu Asp Thr His His Trp
1 5

<210> SEQ ID NO 105
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 105
cggcctactc gtctttctcc g 21

<210> SEQ ID NO 106
<211> LENGTH: 7
<212> TYPE: PRT
<213> ORGANISM: Artificial Sequence
<220> FEATURE:

<223> OTHER INFORMATION: Description of Artificial Sequence: Synthetic
peptide

<400> SEQUENCE: 106

Arg Pro Thr Arg Leu Ser Pro
1 5

<210> SEQ ID NO 107
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 107
gatgcttggt cggcttctat t 21

<210> SEQ ID NO 108
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 108

Asp Ala Trp Ser Ala Ser Ile
1 5

<210> SEQ ID NO 109
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 109
tataagtgtt ggccgaggag t 21

<210> SEQ ID NO 110
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 110

Tyr Lys Cys Trp Pro Arg Ser
1 5

<210> SEQ ID NO 111
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 111
aagtatctga ctaatctttc t 21

<210> SEQ ID NO 112
<211> LENGTH: 7
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 112

Lys Tyr Leu Thr Asn Leu Ser
1               5


<210> SEQ ID NO 113
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113

tcgcggcctc cgccgtctct g                                                21


<210> SEQ ID NO 114
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Ser Arg Pro Pro Pro Ser Leu
1               5


<210> SEQ ID NO 115
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115

taggcgccga ttctttagtt g                                                21


<210> SEQ ID NO 116
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116

atgcctcctt ctcctccggg t                                                21


<210> SEQ ID NO 117
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Met Pro Pro Ser Pro Pro Gly
1               5


<210> SEQ ID NO 118
```

<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 118
ccgtttcctc agatgctttt t 21

<210> SEQ ID NO 119
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 119

Pro Phe Pro Gln Met Leu Phe
1 5

<210> SEQ ID NO 120
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 120
cctcaggcgt ctcatgttaa t 21

<210> SEQ ID NO 121
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 121

Pro Gln Ala Ser His Val Asn
1 5

<210> SEQ ID NO 122
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 122
gagtattgtt cttagattcc t 21

<210> SEQ ID NO 123
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 123

Glu Tyr Cys Ser
1

<210> SEQ ID NO 124
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 124
tcgtagaatt tgcgggtgtt g 21

<210> SEQ ID NO 125
<211> LENGTH: 1
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 125

Ser
1

<210> SEQ ID NO 126
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 126
tattatcatt cgctgtcgtc g 21

<210> SEQ ID NO 127
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 127

Tyr Tyr His Ser Leu Ser Ser
1 5

<210> SEQ ID NO 128
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 128
aagcattctc agcggcggaa t 21

<210> SEQ ID NO 129
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 129

Lys His Ser Gln Arg Arg Asn 1 5

<210> SEQ ID NO 130
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 130
tagactaatg tgtggattaa t 21

<210> SEQ ID NO 131
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 131
actaagacgc ctgagcatta g 21

<210> SEQ ID NO 132
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 132

Thr Lys Thr Pro Glu His
1 5

<210> SEQ ID NO 133
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 133
gggccggagg ggccgcgtct g 21

<210> SEQ ID NO 134
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 134

Gly Pro Glu Gly Pro Arg Leu
1 5

<210> SEQ ID NO 135
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 135

```
tgtacttcta atctgcatgg g                                             21


<210> SEQ ID NO 136
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Cys Thr Ser Asn Leu His Gly
1               5


<210> SEQ ID NO 137
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137

gttattactc atctgactga t                                             21


<210> SEQ ID NO 138
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Val Ile Thr His Leu Thr Asp
1               5


<210> SEQ ID NO 139
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139

gattctaatc attttggtcc g                                             21


<210> SEQ ID NO 140
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Asp Ser Asn His Phe Gly Pro
1               5


<210> SEQ ID NO 141
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 141
ccgagtcagc agacttagat g 21

<210> SEQ ID NO 142
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 142

Pro Ser Gln Gln Thr
1 5

<210> SEQ ID NO 143
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 143
tttgttgctg attgggagcc t 21

<210> SEQ ID NO 144
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 144

Phe Val Ala Asp Trp Glu Pro
1 5

<210> SEQ ID NO 145
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 145
ctgatgcaga ctaatattac g 21

<210> SEQ ID NO 146
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 146

Leu Met Gln Thr Asn Ile Thr
1 5

<210> SEQ ID NO 147
<211> LENGTH: 21
<212> TYPE: DNA
<213> ORGANISM: Artificial Sequence
<220> FEATURE:

-continued

```
<223> OTHER INFORMATION: Description of Artificial Sequence: Synthetic
      oligonucleotide

<400> SEQUENCE: 147

ctggtggttc ctaatcgtga t                                          21


<210> SEQ ID NO 148
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Leu Val Val Pro Asn Arg Asp
1               5


<210> SEQ ID NO 149
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Thr Leu Ala Val Pro Phe Lys
1               5
```